United States Patent
Kreischer

(10) Patent No.: US 10,927,054 B2
(45) Date of Patent: *Feb. 23, 2021

(54) ETHYLENE OLIGOMERIZATION/TRIMERIZATION/TETRAMERIZATION REACTOR

(71) Applicant: Chevron Phillips Chemical Company LP, The Woodlands, TX (US)

(72) Inventor: Bruce E. Kreischer, Kingwood, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/676,309

(22) Filed: Nov. 6, 2019

(65) Prior Publication Data

US 2020/0071243 A1 Mar. 5, 2020

Related U.S. Application Data

(63) Continuation of application No. 14/858,526, filed on Sep. 18, 2015, now Pat. No. 10,519,077, and a (Continued)

(51) Int. Cl.
*C07C 2/08* (2006.01)
*C07C 2/32* (2006.01)
(Continued)

(52) U.S. Cl.
CPC ............... *C07C 2/32* (2013.01); *B01J 4/004* (2013.01); *B01J 4/02* (2013.01); *B01J 8/22* (2013.01);
(Continued)

(58) Field of Classification Search
None
See application file for complete search history.

(56) References Cited

U.S. PATENT DOCUMENTS

| 3,441,631 A | 4/1969 | Fernald et al. |
| 3,444,263 A | 5/1969 | Fernald et al. |

(Continued)

FOREIGN PATENT DOCUMENTS

| CA | 985294 | 3/1976 |
| EP | 0177999 A1 | 4/1986 |

(Continued)

OTHER PUBLICATIONS

International Search Report and Written Opinion, PCT/US2016/051501, dated Jun. 13, 2017, 8 pages.

(Continued)

*Primary Examiner* — Philip Y Louie
(74) *Attorney, Agent, or Firm* — Conley Rose, P.C.; Monte R. Rhodes; Rodney Carroll

(57) ABSTRACT

A process includes periodically or continuously introducing an olefin monomer and periodically or continuously introducing a catalyst system or catalyst system components into a reaction mixture within a reaction system, oligomerizing the olefin monomer within the reaction mixture to form an oligomer product, and periodically or continuously discharging a reaction system effluent comprising the oligomer product from the reaction system. The reaction system includes a total reaction mixture volume and a heat exchanged portion of the reaction system comprising a heat exchanged reaction mixture volume and a total heat exchanged surface area providing indirect contact between the reaction mixture and a heat exchange medium. A ratio of the total heat exchanged surface area to the total reaction mixture volume within the reaction system is in a range from 0.75 in$^{-1}$ to 5 in$^{-1}$, and an oligomer product discharge rate from the reaction system is between 1.0 (lb)(hr$^{-1}$)(gal$^{-1}$) to 6.0 (lb)(hr$^{-1}$)(gal$^{-1}$).

13 Claims, 8 Drawing Sheets

Related U.S. Application Data continuation of application No. 14/858,588, filed on Sep. 18, 2015, now Pat. No. 10,513,473.

(51) Int. Cl.
| | | |
|---|---|---|
| *C07C 2/88* | (2006.01) | |
| *C07C 2/30* | (2006.01) | |
| *B01J 8/22* | (2006.01) | |
| *B01J 19/18* | (2006.01) | |
| *B01J 4/00* | (2006.01) | |
| *B01J 4/02* | (2006.01) | |

(52) U.S. Cl.
CPC ........... *B01J 8/222* (2013.01); *B01J 19/1806* (2013.01); *B01J 19/1818* (2013.01); *B01J 19/1825* (2013.01); *B01J 19/1856* (2013.01); *B01J 19/1862* (2013.01); *B01J 19/1881* (2013.01); *C07C 2/30* (2013.01); *C07C 2/88* (2013.01); *B01J 2208/00044* (2013.01); *B01J 2208/00141* (2013.01); *B01J 2208/00176* (2013.01); *B01J 2208/00212* (2013.01); *B01J 2208/00265* (2013.01); *B01J 2208/00274* (2013.01); *B01J 2208/00283* (2013.01); *B01J 2208/00911* (2013.01); *B01J 2219/0011* (2013.01); *B01J 2219/00056* (2013.01); *B01J 2219/00083* (2013.01); *B01J 2219/00094* (2013.01); *B01J 2219/00108* (2013.01); *B01J 2219/00195* (2013.01); *B01J 2219/00211* (2013.01); *B01J 2219/00229* (2013.01); *B01J 2219/00238* (2013.01); *C07C 2523/26* (2013.01); *C07C 2523/755* (2013.01); *C07C 2527/135* (2013.01); *C07C 2531/12* (2013.01); *C07C 2531/14* (2013.01); *C07C 2531/24* (2013.01)

(56) References Cited

U.S. PATENT DOCUMENTS

| | | |
|---|---|---|
| 3,444,264 A | 5/1969 | Fernald et al. |
| 3,477,813 A | 11/1969 | Fernald et al. |
| 3,478,124 A | 11/1969 | Fernald et al. |
| 3,482,200 A | 12/1969 | Hamilton |
| 3,502,741 A | 3/1970 | Fernald et al. |
| 3,510,539 A | 5/1970 | Fernald et al. |
| 3,531,253 A | 9/1970 | Fernald et al. |
| 3,562,348 A | 2/1971 | Jenkins |
| 3,636,091 A | 1/1972 | Mason et al. |
| 3,641,191 A | 2/1972 | Fernald et al. |
| 3,644,563 A | 2/1972 | Bauer et al. |
| 3,647,915 A | 5/1972 | Bauer et al. |
| 3,676,523 A | 7/1972 | Mason |
| 3,686,159 A | 8/1972 | Bauer et al. |
| 3,686,351 A | 8/1972 | Mason |
| 3,702,345 A | 11/1972 | Fernald et al. |
| 3,737,475 A | 6/1973 | Mason |
| 3,825,615 A | 7/1974 | Lutz |
| 4,020,121 A | 4/1977 | Kister et al. |
| 4,022,839 A | 5/1977 | Beuther et al. |
| 4,229,607 A | 10/1980 | Gum et al. |
| 4,260,844 A | 4/1981 | O'Donnell et al. |
| 4,284,837 A | 8/1981 | Lutz |
| 4,361,714 A | 11/1982 | Langer et al. |
| 4,377,499 A | 3/1983 | O'Donnell et al. |
| 4,377,720 A | 3/1983 | Langer |
| 4,396,788 A | 8/1983 | Langer, Jr. |
| 4,409,414 A | 10/1983 | Langer, Jr. |
| 4,410,750 A | 10/1983 | Langer, Jr. |
| 4,429,177 A | 1/1984 | Morganson et al. |
| 4,434,312 A | 2/1984 | Langer, Jr. |
| 4,434,313 A | 2/1984 | Langer, Jr. |
| 4,442,309 A | 4/1984 | Langer, Jr. |
| 4,472,522 A | 9/1984 | Singleton |
| 4,472,525 A | 9/1984 | Singleton |
| 4,486,615 A | 12/1984 | Langer, Jr. |
| 4,503,279 A | 3/1985 | Singleton |
| 4,503,280 A | 3/1985 | Singleton |
| 4,528,416 A | 7/1985 | Lutz |
| 4,783,573 A | 11/1988 | Shiraki et al. |
| 4,855,525 A | 8/1989 | Young et al. |
| 4,886,933 A | 12/1989 | Shiraki et al. |
| 4,966,874 A | 10/1990 | Young et al. |
| 5,198,563 A | 3/1993 | Reagen et al. |
| 5,260,500 A | 11/1993 | Shiraki et al. |
| 5,288,823 A | 2/1994 | Reagen |
| 5,331,104 A | 7/1994 | Reagen et al. |
| 5,340,785 A | 8/1994 | Reagen et al. |
| 5,345,022 A | 9/1994 | Hedrich et al. |
| 5,360,879 A | 11/1994 | Reagen et al. |
| 5,376,612 A | 12/1994 | Reagen et al. |
| 5,382,738 A | 1/1995 | Reagen et al. |
| 5,399,539 A | 3/1995 | Reagen et al. |
| 5,438,027 A | 8/1995 | Reagen et al. |
| 5,470,926 A | 11/1995 | Reagen et al. |
| 5,510,556 A | 4/1996 | Hedrich et al. |
| 5,523,507 A | 6/1996 | Reagen et al. |
| 5,543,375 A | 8/1996 | Lashier et al. |
| 5,557,027 A | 9/1996 | Kemp |
| 5,563,312 A | 10/1996 | Knudsen et al. |
| 5,689,028 A | 11/1997 | Lashier et al. |
| 5,750,816 A | 5/1998 | Araki et al. |
| 5,763,723 A | 6/1998 | Reagen et al. |
| 5,814,575 A | 9/1998 | Reagen et al. |
| 5,856,257 A | 1/1999 | Freeman et al. |
| 5,856,612 A | 1/1999 | Araki et al. |
| 5,859,303 A | 1/1999 | Lashier |
| 5,910,619 A | 6/1999 | Urata et al. |
| 5,955,555 A | 9/1999 | Bennett |
| 6,103,946 A | 8/2000 | Brookhart, III et al. |
| 6,133,495 A | 10/2000 | Urata et al. |
| 6,291,733 B1 | 9/2001 | Small et al. |
| 6,376,731 B1 | 4/2002 | Evans et al. |
| 6,380,451 B1 | 4/2002 | Kreischer et al. |
| 6,451,939 B1 | 9/2002 | Britovsek et al. |
| 6,455,648 B1 | 9/2002 | Freeman et al. |
| 6,455,660 B1 | 9/2002 | Clutton et al. |
| 6,458,739 B1 | 10/2002 | Kimberley et al. |
| 6,472,341 B1 | 10/2002 | Kimberley et al. |
| 6,489,497 B1 | 12/2002 | Brookhart, III et al. |
| 6,545,108 B1 | 4/2003 | Moody et al. |
| 6,559,091 B1 | 5/2003 | Moody et al. |
| 6,576,721 B2 | 6/2003 | Kobayashi et al. |
| 6,657,026 B1 | 12/2003 | Kimberley et al. |
| 6,683,187 B2 | 1/2004 | De Boer et al. |
| 6,710,006 B2 | 3/2004 | De Boer et al. |
| 6,825,148 B2 | 11/2004 | Brown et al. |
| 6,911,505 B2 | 6/2005 | Small |
| 6,911,506 B2 | 6/2005 | Small et al. |
| 7,001,964 B2 | 2/2006 | Small |
| 7,045,632 B2 | 5/2006 | Small |
| 7,049,442 B2 | 5/2006 | De Boer et al. |
| 7,056,997 B2 | 6/2006 | Small et al. |
| 7,129,304 B1 | 10/2006 | Small et al. |
| 7,157,612 B2 | 1/2007 | Ewert et al. |
| 7,169,961 B2 | 1/2007 | Kobayashi et al. |
| 7,223,893 B2 | 5/2007 | Small et al. |
| 7,268,096 B2 | 9/2007 | Small et al. |
| 7,271,121 B2 | 9/2007 | Small et al. |
| 7,285,607 B2 | 10/2007 | Blann et al. |
| 7,291,685 B2 | 11/2007 | Kobayashi et al. |
| 7,297,832 B2 | 11/2007 | Blann et al. |
| 7,323,524 B2 | 1/2008 | Blann et al. |
| 7,378,537 B2 | 5/2008 | Small et al. |
| 7,384,886 B2 | 6/2008 | Knudsen et al. |
| 7,396,970 B1 | 7/2008 | Battiste |
| 7,456,284 B2 | 11/2008 | Small |
| 7,476,775 B2 | 1/2009 | Kreischer |
| 7,511,183 B2 | 3/2009 | Blann et al. |
| 7,525,009 B2 | 4/2009 | Blann et al. |
| 7,566,679 B2 | 7/2009 | Bölt et al. |
| 7,683,149 B2 | 3/2010 | Ionkin et al. |

(56) References Cited

U.S. PATENT DOCUMENTS

| | | |
|---|---|---|
| 7,718,838 B2 | 5/2010 | Woodard et al. |
| 7,727,926 B2 | 6/2010 | Small et al. |
| 7,728,160 B2 | 6/2010 | Small et al. |
| 7,728,161 B2 | 6/2010 | Small et al. |
| 7,820,581 B2 | 10/2010 | Knudsen et al. |
| 7,829,749 B2 | 11/2010 | Gao et al. |
| 7,897,826 B2 | 3/2011 | Fritz et al. |
| 7,902,415 B2 | 3/2011 | Small |
| 7,906,681 B2 | 3/2011 | Gao et al. |
| 7,910,670 B2 | 3/2011 | Knudsen et al. |
| 7,964,763 B2 | 6/2011 | Dixon et al. |
| 7,977,269 B2 | 7/2011 | Small et al. |
| 7,994,363 B2 | 8/2011 | Gao et al. |
| 7,994,376 B2 | 8/2011 | Small et al. |
| 8,049,052 B2 | 11/2011 | Kreischer et al. |
| 8,076,523 B2 | 12/2011 | Bollmann et al. |
| 8,134,038 B2 | 3/2012 | McGuinness et al. |
| 8,252,955 B2 | 8/2012 | Gao et al. |
| 8,252,956 B2 | 8/2012 | Gao et al. |
| 8,268,941 B2 | 9/2012 | Kleingeld et al. |
| 8,269,055 B2 | 9/2012 | Fritz et al. |
| 8,329,608 B2 | 12/2012 | Knudsen et al. |
| 8,334,420 B2 | 12/2012 | Small et al. |
| 8,344,198 B2 | 1/2013 | Ewert et al. |
| 8,367,786 B2 | 2/2013 | Dixon et al. |
| 8,461,406 B2 | 6/2013 | Overett et al. |
| 8,471,085 B2 | 6/2013 | Sydora |
| 8,680,003 B2 | 3/2014 | Sydora et al. |
| 2003/0153798 A1 | 8/2003 | Kobayashi et al. |
| 2009/0216057 A1 | 8/2009 | Fritz et al. |
| 2009/0306312 A1 | 12/2009 | Fritz et al. |
| 2009/0306442 A1 | 12/2009 | Pretorius et al. |
| 2010/0036185 A1 | 2/2010 | Yokoyama et al. |
| 2010/0113257 A1 | 5/2010 | Kreischer et al. |
| 2010/0113851 A1 | 5/2010 | Kreischer et al. |
| 2010/0113852 A1 | 5/2010 | Sydora |
| 2010/0191029 A1 | 7/2010 | Fritz et al. |
| 2010/0292423 A1 | 11/2010 | Aliyev et al. |
| 2010/0331503 A1 | 12/2010 | Emoto et al. |
| 2011/0046429 A1 | 2/2011 | Aliyev et al. |
| 2011/0054130 A1 | 3/2011 | Aliyev et al. |
| 2011/0054233 A1 | 3/2011 | Mousa et al. |
| 2011/0257350 A1 | 10/2011 | Jaber et al. |
| 2011/0282016 A1 | 11/2011 | Carter et al. |
| 2012/0041241 A1 | 2/2012 | Ewart et al. |
| 2012/0088933 A1 | 4/2012 | Carter et al. |
| 2012/0101321 A1 | 4/2012 | Brown et al. |
| 2012/0142989 A1 | 6/2012 | Jaber et al. |
| 2012/0184692 A1 | 7/2012 | Fritz et al. |
| 2012/0199467 A1 | 8/2012 | Gildenhuys et al. |
| 2012/0271087 A1 | 10/2012 | Brown et al. |
| 2012/0302809 A1 | 11/2012 | Citron |
| 2012/0316303 A1 | 12/2012 | Hanton et al. |
| 2013/0150605 A1 | 6/2013 | Sydora et al. |
| 2013/0150642 A1 | 6/2013 | Sydora et al. |
| 2013/0172651 A1 | 7/2013 | Small |
| 2013/0331629 A1 | 12/2013 | Sydora et al. |

FOREIGN PATENT DOCUMENTS

| | | |
|---|---|---|
| EP | 0320571 A2 | 6/1989 |
| EP | 0444505 A2 | 9/1991 |
| EP | 0608447 B2 | 8/1994 |
| EP | 0706983 A1 | 4/1996 |
| EP | 1229020 A1 | 8/2002 |
| EP | 1749807 A1 | 2/2007 |
| EP | 1752434 A1 | 2/2007 |
| EP | 1780189 A1 | 5/2007 |
| EP | 2258674 A1 | 12/2010 |
| GB | 1186609 | 4/1970 |
| WO | 9102707 A1 | 3/1991 |
| WO | 2013013300 A1 | 1/2013 |
| WO | 2015094207 A1 | 6/2015 |

OTHER PUBLICATIONS

Freitas, E. R., et al., "Shell's Higher Olefins Process," Chemical Engineering Progress, Jan. 1979, pp. 73-76 plus 1 page publishing information, vol. 75, Issue 1, AIChE.

Keim, Wilhelm, Oligomerization of Ethylene to α-Olefins: Discovery and Development of the Shell Higher Olefin Process (SHOP), Angewandte Chemie International Edition, 2013, pp. 12492-12496, vol. 52, Wiley-VCH Verlag GmbH & Co. KGaA, Weinheim.

McNaught, Alan D., et al., "Compendium of Chemical Terminology," IUPAC Recommendations, Second edition, 1997, Wiley-Blackwell.

Peuckert, Marcell, et al., "A New Nickel Complex for the Oligomerization of Ethylene," Organometallics, 1983, pp. 594-597, vol. 2, No. 5, American Chemical Society.

Shiraki, Yasushi, et al., "Synthesis of α-Olefin by Oligomerization of Ethylene (Part 2) Study of the Mechanism of By-product Formation," Sekiyu Gakkaishi,1999, pp. 235-245, vol. 42, No. 4.

Shiraki, Yasushi, et al., "Synthesis of α-Olefin by Oligomerization of Ethylene (Part 3) Development of Three Components Catalyst Consisting of Zirconiumtetrachloride, Ethylaluminumsesquichloride and Triethylaluminum," Sekiyu Gakkaishi, 2000, pp. 328-338, vol. 43, No. 5.

Shiraki, Yasushi, et al., "Synthesis of α-Olefin by Oligomerization of Ethylene (Part 4) Effects of Solvent and Additional Component as Ligand," Sekiyu Gakkaishi, 2001, pp. 25-35, vol. 44, No. 1.

Shiraki, Yasushi, et al., "Synthesis of α-Olefin by Oligomerization of Ethylene (Part 5) Post-treatment of Catalysts," Sekiyu Gakkaishi, 2001, pp. 109-119, vol. 44, No. 2.

Yamada, Tadashi, et al., "Development of α-Olefin Production Catalyst and Its Process," Sekiyu Gakkaishi, 1994, pp. 337-346, vol. 37, No. 4.

"Engineering Essentials: Heat Exchangers," Hydraulics & Pneumatics, Jan. 1, 2012, pp. 1-7.

Sinclair, "Stainless Steel Heating & Cooling Vessels," Feb. 1, 2001. pp. 1-4.

Foreign Communication from a related application—Chinese Office Action Translation, CN Patent Application No. 201680054291.X, dated Sep. 1, 2020, 20 pages.

Zhou, Lili, et al., "Pharmaceutical Equipment and Workshop Design 2nd. Edition," Jan. 31, 2011, p. 337, China Medical Science Press, Translation, 4 pages.

Hou, Wenshun, "Introduction to Chemical Design," Nov. 30, 1999, p. 2514, Chemical Industry Press, Translation, 5 pages.

ETHYLENE OLIGOMERIZATION/TRIMERIZATION/TETRAMERIZATION REACTOR

CROSS-REFERENCE TO RELATED APPLICATIONS

This application is a continuation of and claims priority to U.S. patent application Ser. No. 14/858,526 filed on Sep. 18, 2015, published as U.S. Patent Application Publication No. 2017/0081257 A1, and Ser. No. 14/858,588 filed on Sep. 18, 2015, published as U.S. Patent Application Publication No. 2017/0081256 A1, both entitled "Design of an Ethylene Oligomerization/Trimerization/Tetramerization Reactor," and each of which is incorporated herein by reference in its entirety.

FIELD OF THE INVENTION

The present disclosure relates to processes for producing an olefin oligomer. More particularly, the present disclosure relates to improved processes for oligomerizing olefins.

BACKGROUND OF THE INVENTION

Reaction systems are used in a variety of industrial chemical processes, for example oligomerization and/or polymerization of olefins (commonly known as alkenes) to produce oligomers and/or polymers, respectively. For example, aluminum, nickel, zirconium, and iron based catalyst systems for the synthesis of $C_4$ to $C_{30+}$ alpha olefins from ethylene and chromium based catalyst systems for the selective synthesis of 1-hexene from ethylene constitute commercially significant processes for the preparation of alpha olefins. Many applications exist for alpha olefins, including employment as intermediates in the manufacture of detergents, as more environmentally friendly replacements where refined oils might otherwise be used, as monomers or comonomers in the production of polyolefins (e.g., polyethylene), and as intermediates for many other types of products. Demand for alpha olefins continues to rise, and alpha olefin producers seek adequate capacity to meet demand, for example via improved reaction systems and methods of making and using same.

SUMMARY OF THE INVENTION

In an embodiment, a process comprises periodically or continuously introducing an olefin monomer and periodically or continuously introducing a catalyst system or catalyst system components into a reaction mixture within a reaction system, oligomerizing the olefin monomer within the reaction mixture to form an oligomer product, and periodically or continuously discharging a reaction system effluent comprising the oligomer product from the reaction system. The reaction system comprises: a total reaction mixture volume within the reaction system; and a heat exchanged portion of the reaction system comprising a heat exchanged reaction mixture volume and a total heat exchanged surface area providing indirect thermal contact between the reaction mixture and a heat exchange medium. A ratio of the total heat exchanged surface area to the total reaction mixture volume within the reaction system is in a range from 0.75 $in^{-1}$ to 5 $in^{-1}$, and wherein an oligomer product discharge rate from the reaction system is between 1.0 $(lb)(hr^{-1})(gal^{-1})$ to 6.0 $(lb)(hr^{-1})(gal^{-1})$. The process can also include periodically or continuously introducing a reaction solvent into the reaction mixture within the reaction system. A ratio of the total reaction system heat exchanged surface area to the total reaction mixture volume within the reaction system can be in a range from a minimum value described by the equation [0.64*(oligomer product discharge rate from the reaction system)]−1.16 to a maximum value described by the equation [0.64*(oligomer product discharge rate from the reaction system)]+0.76. A ratio of the heat exchanged reaction mixture volume to the total reaction mixture volume within the reaction system can be in a range from 0.70 to 1.0. The reaction system can also include a non-heat exchanged portion of the reaction system comprising a non-heat exchanged reaction mixture volume and a total non-heat exchanged surface area that does not provide heat exchange between the reaction mixture and the heat exchange medium, and an average temperature of the reaction mixture within the non-heat exchanged portion of the reaction system can be within 0.61% of an average temperature of the reaction mixture within the heat exchanged portion of the reaction system. The reaction system can also include a non-heat exchanged portion of the reaction system comprising a non-heat exchanged reaction mixture volume and a total non-heat exchanged surface area that does not provide heat exchange between the reaction mixture and the heat exchange medium, and an average temperature of the heat exchange medium can be within 9.3% of the average temperature of the reaction mixture within the heat exchanged portion of the reaction system. The reaction system can comprise a reactor selected from the group consisting of a continuous stirred tank reactor (CSTR), a plug flow reactor, or any combinations thereof. The reaction system can comprise a continuous stirred tank reactor, and the heat exchange medium can be in indirect contact with the reaction mixture within a jacket around at least a portion of the outer wall of the continuous stirred tank reactor, within internal heat exchange coils, or any combination thereof. The reaction system can comprise one or more plug flow reactors, and the heat exchange medium can be in indirect contact with the reaction mixture through a wall of at least a portion of at least one plug flow reactor. The reaction system can comprise a reaction mixture path comprising the reactor, and the reaction mixture can be recycled through the reactor and a ratio of a volumetric reaction mixture recycle flow rate to a volumetric discharge rate of the reaction system effluent is between 8 and 60. The olefin monomer can consist essentially of ethylene. The catalyst system can comprise chromium, a heteroatomic ligand, and a metal alkyl compound. The catalyst system can comprise an organometallic compound consisting essentially of a trialkylaluminum compound. The reaction mixture can comprise the catalyst system, and the catalyst system can comprises a) a nickel compound and a bidentate organophosphine having at least one tertiary organophosphorus group or b) a complex of a nickel compound and a bidentate organophosphine having at least one tertiary organophosphorus group. The reaction mixture can comprise the catalyst system, and the catalyst system can comprise, a) a zirconium halide, hydrocarbyloxide, or carboxylate, and an metal alkyl compound, or b) a zirconium halide, alkoxide, or carboxylate, a Lewis base, and a metal alkyl compound. The reaction mixture can comprise the catalyst system, and the catalyst system can comprise: a) a transition metal complex comprising a transition metal compound complexed to an α-diimine compound and a metal alkyl compound, b) a transition metal complex comprising a transition metal compound complexed to a pyridine 2,6-bisimine compound and a metal alkyl compound, c) a transition metal compound, a pyridine 2,6-bisimine compound, and a metal alkyl compound, or d) any combination thereof.

In an embodiment, a reaction system for oligomerizing an olefin monomer comprises one or more reaction system inlets configured to periodically or continuously introduce an olefin monomer, a catalyst system or catalyst system components, or any combination thereof to a reaction mixture within the reaction system, one or more reaction system reaction mixture outlets configured to periodically or continuously discharge a reaction system effluent comprising an oligomer product from the reaction system, a total reaction mixture volume within the reaction system, a heat exchanged portion of the reaction system comprising a heat exchanged reaction mixture volume, and a total heat exchanged surface area providing indirect thermal contact between the reaction mixture and a heat exchange medium. A ratio of the total heat exchanged surface area to the total reaction mixture volume within the reaction system is in a range from 0.75 in$^{-1}$ to 5 in$^{-1}$, and an oligomer product discharge rate from the reaction system is between 1.0 lb/hr/gal to 6.0 lb/hr/gal. A ratio of the total reaction system heat exchanged surface area to the total reaction mixture volume within the reaction system can be in a range from a minimum value described by the equation [0.64*(oligomer product discharge rate from the reaction system)]−1.16 to a maximum value described by the equation [0.64*(oligomer product discharge rate from the reaction system)]+0.76. A ratio of the heat exchanged reaction mixture volume to the total reaction mixture volume within the reaction system can be in a range from 0.70 to 1.0. The reaction system can also include a non-heat exchanged portion of the reaction system comprising a non-heat exchanged reaction mixture volume and a total non-heat exchanged surface area that does not providing heat exchange between the reaction mixture and the heat exchange medium, and an average temperature of the reaction mixture within the non-heat exchanged portion of the reaction system can be within 0.61% of an average temperature of the reaction mixture within the heat exchanged portion of the reaction system. The reaction system can also include a non-heat exchanged portion of the reaction system comprising a non-heat exchanged reaction mixture volume and a total non-heat exchanged surface area that does not providing heat exchange between the reaction mixture and the heat exchange medium, and an average temperature of the heat exchange medium can be within 9.3% of the average temperature of the reaction mixture within the heat exchanged portion of the reaction system. The reaction system can comprise a reactor selected from the group consisting of a continuous stirred tank reactor (CSTR), a plug flow reactor, or any combinations thereof. The reaction system can comprise one or more plug flow reactors and the heat exchange medium has indirect contact with the reaction mixture through a wall of at least a portion of at least one plug flow reactor.

In an embodiment, a process comprises periodically or continuously introducing an olefin monomer and periodically or continuously introducing a catalyst system or catalyst system components into a reaction mixture within a reaction system, oligomerizing the olefin monomer within the reaction mixture to form an oligomer product, and periodically or continuously discharging a reaction system effluent comprising the oligomer product from the reaction system. The reaction system comprises: a total reaction mixture volume within the reaction system, and a heat exchanged portion of the reaction system comprising a heat exchanged reaction mixture volume and a total heat exchanged surface area providing indirect thermal contact between the reaction mixture and a heat exchange medium. A ratio of the heat exchanged reaction mixture volume to the total reaction mixture volume within the reaction system is in a range from 0.7 to 1, and the reaction mixture passing through the heat exchanged portion of the reaction system has a Reynolds number of greater than 2×10$^5$.

BRIEF DESCRIPTION OF THE DRAWINGS

The patent application subject matter can be understood by reference to the following description taken in conjunction with the accompanying drawings, in which like reference numerals identify like elements, and in which.

Figure 1:
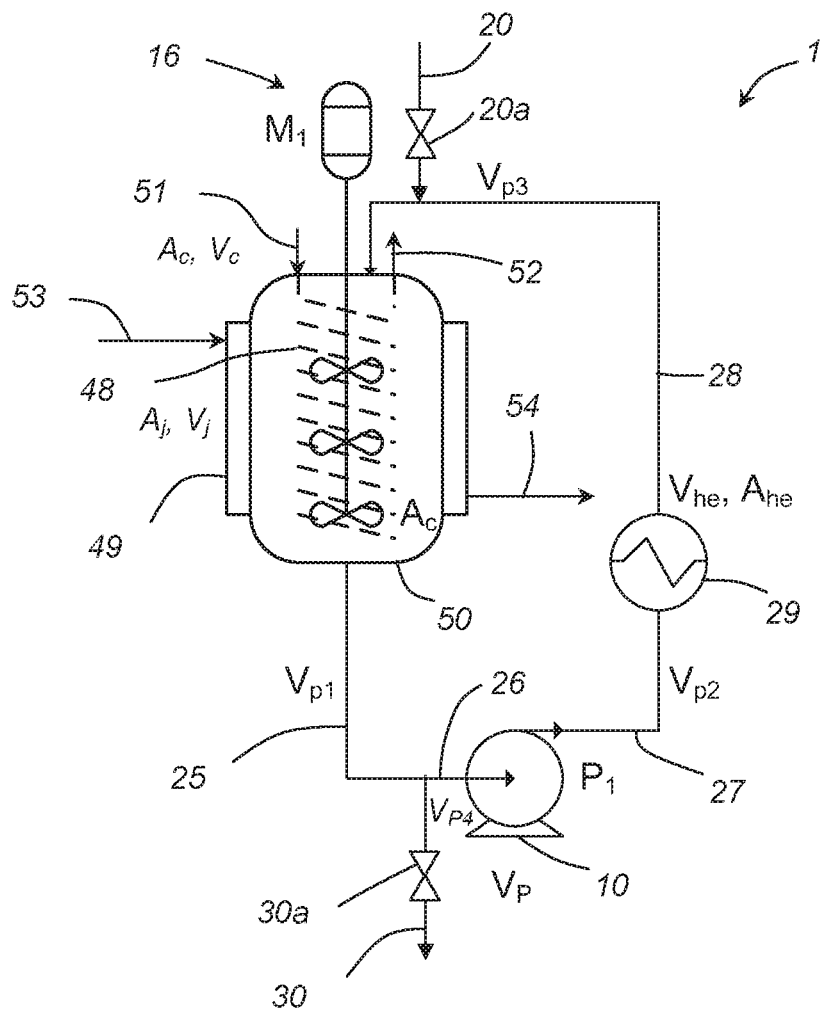
FIG. 1 illustrates an embodiment of all or a portion of an oligomerization reaction process.

While the patent application subject matter is susceptible to various modifications and alternative forms, the drawings illustrate specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope of the invention as defined by the appended claims.

DETAILED DESCRIPTION

Illustrative embodiments of the subject matter claimed below will now be disclosed. In the interest of clarity, not all features of an actual implementation are described in this specification. It can be appreciated that in the development of any such actual embodiment, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and embodiments of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

Regarding claim transitional terms or phrases, the transitional term "comprising", which is synonymous with "including," "containing," "having" or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of material A. When a claim includes different features and/or feature classes (for example, a method step, feedstock features, and/or product features, among other possibilities), the transitional terms comprising, consisting essentially of, and consisting of apply only to the feature class that is utilized and it is possible to have different transitional terms or phrases utilized with different features within a claim. For example a method can comprise several recited steps (and other non-recited steps) but utilize a catalyst system preparation consisting of specific steps but utilize a catalyst system comprising recited components and other non-recited components.

Within this specification, use of "comprising" or an equivalent expression contemplates the use of the phrase "consisting essentially of," "consists essentially of," or equivalent expressions as alternative embodiments to the open-ended expression. Additionally, use of "comprising" or an equivalent expression or use of "consisting essentially of" in the specification contemplates the use of the phrase "consisting of," "consists of," or equivalent expressions as an alternative to the open-ended expression or middle ground expression, respectively. For example, "comprising" should be understood to include "consisting essentially of," and "consisting of" as alternative embodiments for the aspect, features, and/or elements presented in the specification unless specifically indicated otherwise.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reactor system" refers to any portion of equipment in which a desired reaction occurs, including but not limited to, a reactor, associated piping, associated pumps, and any other associated equipment. It should be noted that in some cases a "reactor" can also be a "reactor system." For example, in some instances a polyethylene loop reactor can be considered a reactor system. The terms "reactor" and "reactor system" can be qualified to refer to more specific "reactors" and "reactor systems" by use of additional qualifying terms. For example, the use of the term "oligomerization reactor" and "oligomerization reactor system" indicates that the desired reaction within the reactor and/or reactor system is an oligomerization.

Within this specification, term "reaction system" refers to the portion of a process, the associated equipment and associated process lines where all the necessary reaction components and reaction conditions are present such that the reaction can occur at a desired rate. That is to say that the reaction system begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction system). For example, in terms of an ethylene oligomerization process, the reaction system begins at the point where sufficient ethylene and active catalyst system is present under the sufficient reaction conditions to maintain oligomer product production at the desired rate and the reaction system ends at a point where either the catalyst system is deactivated, sufficient ethylene is not present to sustain oligomer product production, or other reaction conditions are not sufficient to maintain the oligomer product production or the desired oligomer product production rate. Within this specification the "reaction system" can comprise one or more reactor systems, one or more reactors, and associated equipment where all the necessary reaction components and reaction conditions are present such that the reaction can occur at a desired rate. The term "reaction system" can be qualified to refer to more specific "reaction systems" by use of additional qualifying terms. For example, the use of the term "oligomerization reaction system" indicates that the desired reaction within the "reaction system" is an oligomerization.

The term "reaction process" refers to the equipment of a reaction process including the equipment of the reaction system and the equipment and associated process line(s) which can bring the necessary component(s) into and out of the reaction system. The term "reaction process" can be qualified to refer to more specific "reaction processes" by use of additional qualifying terms. For example, the use of the term "oligomerization reaction process" indicates that the "reaction process" relates to an oligomerization.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group can be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. For example, alkamonoenes, alkadienes, and alkatrienes refer to a linear or branched acyclic hydrocarbon olefins having only one carbon-carbon double bond (acyclic having a general formula of $C_{11}H_{2n}$), only two carbon-carbon double bonds (acyclic having a general formula of $C_{n1}H_{2n-2}$), and only three carbon-carbon double bonds (acyclic having a general formula of $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction system effluent," and it derivatives (e.g., oligomerization reaction system effluent, trimerization reaction system effluent, tetramerization reaction system effluent, or trimerization and tetramerization reaction system effluent) generally refers to all the material which exits the reaction system through a reaction system outlet/discharge which discharges a reaction mixture and can include reaction system feed(s) (e.g., olefin, catalyst system or catalyst system components, and/or solvent), and/or reaction product (e.g., oligomer product including oligomers and non-oligomers, trimerization product including trimer and non-trimer, tetramerization product including tetramer and non-tetramer, or trimerization and tetramerization product including trimer and tetramer and non-trimer and tetramer). The term "reaction system effluent" and its derivatives can be qualified to refer to certain portions by use of additional qualifying terms. For example, while reaction system effluent refers to all material which exits the reaction system through the reaction system outlet/discharge, a reaction system oligomer product effluent refers to only the oligomer product within the reaction system effluent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example a reference to a phenyl group comprising a substituent at the 4 position refers to a phenyl group having a non-hydrogen substituent group at the 4 position and hydrogen or any non-hydrogen group at the 2, 3, 5, and 6 positions.

Processes and/or, methods described herein can utilize steps, features, and compounds which are independently described herein. The process and/or methods described herein may or may not utilize step identifiers (e.g., 1), 2), etc., a), b), etc., i), ii), etc., or first, second etc., among others), features (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes and/or methods described herein can have multiple steps, features (e.g. reagent ratios, formation conditions, among other considerations), and/or multiple compounds and/or composition using no descriptor or sometimes having the same general identifier. Consequently, it should be noted that the processes and/or methods described herein can be modified to use an appropriate step or feature identifier (e.g., 1), 2), etc., a), b), etc., i), ii), etc., or first, second etc., among others), feature identifier features (e.g., 1), 2), etc., a), b), etc., i), ii), etc., or first, second etc., among others), and/or compound identifier (e.g., first, second, etc.) regardless of step, feature, and/or compound identifier utilized in the a particular aspect and/or embodiment described herein and that step or feature identifiers can be added and/or modified to indicate individual different steps/features/compounds utilized within the process and/or methods without detracting from the general disclosure.

Processes of forming oligomers are described herein. Such processes generally comprise contacting an olefin and a catalyst system to form an oligomerization product at oligomerization conditions. As used herein, the term "oligomerization" and its derivatives, refers to processes which produce a mixture of products containing at least 70 weight percent products containing from 2 to 30 monomer units. Similarly, as used herein, an "oligomer" is a product that contains from 2 to 30 monomer units while an "oligomerization product" includes all products made by the "oligomerization" process including the "oligomers" and products which are not "oligomers" (e.g., products which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units. Further the terms "oligomerization product" and "oligomer product" can be used interchangeably.

As used herein the term "trimerization," and it derivatives, refers to a process which produces a mixture of products containing at least 70 weight percent products containing three and only three monomer units. As used herein a "trimer" is a product which contains three and only three monomer units while a "trimerization product" includes all products made by the trimerization process including trimer and product which are not trimer (e.g. dimers or tetramers). Generally, an olefin trimerization reduces the number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" can include $C_6$, $C_8$, $C_{10}$, and $C_{12}$ products. In another example, a "trimer" of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule. In an example, a "trimerization" process using ethylene as the monomer produces a mixture of products containing at least 70 weight percent hexene(s).

The term "tetramerization," and its derivatives, refers to a process which produces a mixture of products containing at least 70 weight percent products containing four and only four monomer units. As used herein a "tetramer" is a product which contains four and only four monomer units while a "tetramerization product" includes all products made by the tetramerization process including tetramer and product which are not tetramer (e.g. dimers or trimer). Generally, an olefin tetramerization reduces the number of olefinic bonds, i.e., carbon-carbon double bonds, by three when considering the number of olefin bonds in the monomer units and the number of olefin bonds in the tetramer. It should be noted that the monomer units in the "tetramer" or "tetramerization product" do not have be the same. For example, a "tetramer" of a "tetramerization" process using ethylene and butene as monomers can contain ethylene and/or butene monomer units. In an example, a "tetramer" of a "tetramerization" process using ethylene as the monomer can contain ethylene monomer units. It should also be noted that a single molecule can contain two monomer units. For example, dienes such as 1,3-butadiene and 1,4-pentadiene have two monomer units within one molecule. In an example, a "tetramerization" process using ethylene as the monomer produces a mixture of products containing at least 70 weight percent octene(s).

The term "trimerization and tetramerization," and it derivatives, refers to a process which produces a mixture of products containing at least 70 weight percent products containing three and/or four and only three and/or four monomer units. As used herein a "trimerization and tetramerization product" includes all products made by the "trimerization and tetramerization" process including trimer, tetramer, and products which are not trimer or tetramer (e.g. dimers). In an example, a "trimerization and tetramerization" process using ethylene as the monomer produces a mixture of products containing at least 70 weight percent hexene(s) and/or octene(s).

The olefin and the catalyst system are generally contacted with one another within a reaction system. The reaction system can be referred to as an oligomerization, trimerization, tetramerization, or trimerization and tetramerization reaction system depending upon the catalyst system utilized and the products obtained. The reactor can be referred to as an oligomerization, trimerization, tetramerization, or trimerization or tetramerization reactor depending upon the catalyst system utilized and the products obtained. The reaction system effluent can be referred to as an oligomerization, trimerization, tetramerization, or trimerization or tetramerization reaction system effluent depending upon the catalyst system utilized and the products obtained. The reaction mixture can be referred to as an oligomerization, trimerization, tetramerization, or trimerization or tetramerization mixture depending upon the catalyst system utilized and the products obtained.

In an embodiment the reactor, reactor system, or reaction system can be operated in a batch or continuous manner. In some embodiments, the reactor, reactor system, or reaction system can be operated in a batch manner. In some embodiments, the reactor system, reactor system, or reaction system can be operated in a semi-continuous manner, or alternatively, a continuous manner.

Generally, the reaction system can comprise one or more reactors, one or more discharge locations, and one or more feed lines for one or more feeds. For example, the reaction system can comprise from one to six reactors, from one to four reactors, from one to three reactors, or from one to two reactors. In specific embodiments, the reaction system can comprise a single reactor, two reactors, three reactors or four reactors, for example. When the reaction system has more than one reactor, the reactors can be in series or parallel and can be connected using one or more process lines, depending upon the desired design. In an embodiment, the reaction system can further comprise a motive device (e.g., a pump), one or more process lines from the motive device to the reactor(s) (in terms of process flow) and one or more process lines from the reactor(s) to the motive device (in relation to process flow).

In an embodiment, the oligomerization, trimerization, tetramerization, or tetramerization and trimerization can be operated in a continuous manner (i.e., can be a continuous process) carried out in one or more reactors. In some embodiments, the reaction system for the oligomerization, trimerization, tetramerization, or tetramerization and trimerization of the continuous reaction system independently can comprise a stirred tank reactor, a plug flow reactor, or any other type of reactor; alternatively, a stirred tank reactor, a plug flow reactor, or any combination thereof; alternatively, a stirred tank reactor; or alternatively, a plug flow reactor. In an embodiment, the stirred tank reactor of the continuous reaction system can be a continuous stirred tank reactor. In an embodiment, the continuous reaction system, can comprise one or more continuous stirred tank reactors, plug flow reactors, or any combination thereof; alternatively, one or more continuous stirred tank reactors; alternatively, one or more plug flow reactors; alternatively, one continuous stirred tank reactor; alternatively, one plug flow reactor; alternatively, more than one continuous stirred tank reactor; or alternatively, more than one plug flow reactor. In another embodiment, the reaction system can comprise one or more loop reactors. In some embodiments, where the reaction system comprises more than one reactor, the reactors (any reactor described herein, e.g., a continuous stirred tank reactor, a plug flow reactor, or any combination thereof; or alternatively, a loop reactor) the reactors can be in series, in parallel, or any combination thereof; alternatively, in series; or alternatively, in parallel. In some embodiments, any reactor of the reaction system can have indirect contact between a heat exchange medium (as described herein) and the reaction mixture wherein the heat exchange medium has indirect contact with the reaction mixture through a wall of at least a portion of the reactor. In some embodiments, any continuous stirred tank reactor of the reaction system can have indirect contact between a heat exchange medium (as described herein) and the reaction mixture wherein the heat exchange medium has indirect contact with the reaction mixture through a jacket around at least a portion of the outer wall of the continuous stirred tank reactor, within internal heat exchange coils, or any combination thereof. In some embodiments, any plug flow reactor of the reaction system can have indirect contact between a heat exchange medium (as described herein) and the reaction mixture wherein the heat exchange medium has indirect contact with the reaction mixture through a wall of the plug flow reactor. In other embodiments, the reaction system can comprise one or more plug flow reactors and the heat exchange medium has indirect contact with the reaction mixture through a wall of at least a portion of at least one plug flow reactor. In other embodiments, the continuous reaction system can comprise different types of reactors in combination, and in various arrangements.

In an embodiment, the reaction system can have only one discharge from the reaction system. In some embodiments, the reaction system can have more than one discharge, or only one discharge per reactor in the reaction system, or more discharges than reactors in the reaction system, for example. Generally, the reaction system discharge can be located anywhere along the reaction system. In an embodiment, the reaction system discharge(s) can be located on a reaction system process line, or a reactor inlet, or a reactor outlet. When the reaction system discharge(s) is located on a process line, the discharge(s) can be located on a process line from a reactor, on a process line from a reactor to the motive device (in relation to process flow), on a process recycle line from the motive device to a reactor (in terms of process flow), or any combination thereof, or on a process line from a reactor, or on any process line from a reactor to the motive device, or on a process recycle line from the motive device to a reactor(s), for example. In some embodiments, the reaction system discharge can be located at point within the reaction system where the reaction mixture is well mixed (e.g., within a short distance after a motive device and/or a reactor outlet). When the reaction system has more than one reactor connected in series, a reaction system discharge can be located on a process line exiting the final reactor in the series, or a reaction system discharge(s) can be located on a process line(s) connecting two reactors operating in recycle. When the reaction system is operated in recycle and the reaction system has more than one reactor connected in parallel, a reaction system discharge(s) can be located on a process line(s) prior to a point where the reaction mixture from the one or more parallel reactors is combined, or on a process line after a point where the reaction mixture from at least two parallel reactors is combined, or on a process line after a point where the reaction mixture from all the parallel reactors is combined. When the reaction system is operated in recycle and the reaction system can have more than one reactor connected in parallel, a reaction system discharge(s) can be located on a process line(s) after the motive device (in relation to process flow) but prior to a point where the reaction mixture is split to go to the one or more parallel reactors, or on one or more of the process lines after the motive device and after a point where the reaction mixture is split to go to the one or more parallel reactors, or on each process line after the motive device and after a point where the reaction mixture is split to go to the one or more parallel reactors.

In an embodiment, the reaction system can have a single feed line per distinctive feed to the reaction system. In some embodiments, the reaction system can have more than one feed line per distinctive feed to the reaction system, or a single feed line per distinctive feed to the reaction system per reactor, or more feed lines per distinctive feed to the reaction system per reactor, for example. Generally, the feed line(s) can be placed anywhere along the reaction system. In an embodiment, the reaction system feed line(s) can be located on a reaction system process line, or a reactor inlet, or a reactor outlet (e.g., when the reaction system has two reactors operating in series or the reaction system is operated in recycle). When the reaction system feed line(s) is located on a process line, the feed line(s) can be located on a process line from the motive device to a reactor (in terms of process flow), on a process line from the reactor to the motive device (in relation to process flow), or any combination thereof, or on a process line from the motive device to a reactor, or on a process line from a reactor to the motive device. When the reaction system has more than one reactor connected in series, a reaction system feed line(s) can be located on a process line(s) connecting two reactors. When the reaction system is operated in recycle and the reaction system has more than one reactor connected in parallel, a reaction system feed(s) can be located on a process line(s) prior to a point where the reaction mixture from the one or more parallel reactors is combined, or on a process line after a point where the reaction mixture from at least two parallel reactors are combined, or on a process line after a point where the reaction mixture from all the parallel reactors are combined. When the reaction system has more than one reactor connected in parallel, a reaction system feed(s) can be located on a process line(s) after the motive device (in relation to process flow) but prior to a point where the reaction mixture is split to go to the one or more parallel reactors, or on one or more of the process lines after the motive device and after a point where the reaction mixture is split to go to the one or more parallel reactors, or on each process line after the motive device and after a point where the reaction mixture is split to go to the one or more parallel reactors.

FIG. 1 illustrates an embodiment of reaction process 1 in accordance with the present disclosure including all or a portion of a reaction system and its associated feed inlets, effluent outlets, and other equipment. Specifically FIG. 1 shows a view of a reaction process 1 having a single oligomerization reactor 50. As can be seen, reaction process 1 has feed inlet 20 (which represents one or more feed lines of reaction process 1) to feed one or more reaction components through valve or motive device 20*a* (operating on mass or volume control) to a reaction mixture. As the reaction mixture (described in more detail herein) flows through the reaction loop including oligomerization reactor 50, motive device 10, and process lines 25, 26, 27, and 28, and optional heat exchanger 29 (among other reaction process components) within reaction process 1, reaction product (described in more detail herein) can be produced. Effluent can exit the reaction loop through valve or motive device 30*a* (operating on mass control, volume control, or pressure control) into process line 30. Lines 51 and 52 of oligomerization reactor 50 represent optional heat exchange medium inflow and heat exchange medium outflow lines for optional heat exchange medium to flow through internal heat exchange coils within reactor 50 on lines separate from process lines containing the reaction mixture. Lines 53 and 54 of reactor 50 represent optional heat exchange medium inflow and heat exchange medium outflow lines for optional heat exchange medium to flow through an external heat exchange jacket around all or a portion of oligomerization reactor 50. Additional optional feed lines (not shown) can feed reaction components to process line 25, process line 26, process line 27, and/or reactor 50, among other places. The reaction process 1 can additionally comprise any equipment associated with the reactor, one or more control devices (e.g., a PID controller), measurement instruments (e.g., thermocouples, transducers, and flow meters), alternative inlets, outlet lines, etc.

As provided in reaction process 1, the motive device, such as pump 10, can circulate the reaction mixture through a reaction loop. The pump 10 can be any type of pump, e.g., an in-line axial flow pump with a pump impeller. The impeller can, during operation, create a turbulent mixing zone within a fluid medium circulating through reaction process 1 such that sufficient contact between different reaction components within the reaction mixture occurs. The impeller can be driven by a motor or other motive force.

The reaction mixture in the reaction loop including reactor 50, motive device 10, and process lines 25, 26, 27, and 28 can continuously or periodically receive one or more reaction components through one or more inlets located along the reaction loop. For example, reaction process 1 provides for the introduction of the reaction mixture components via inlet line 20. As noted herein, the reaction system of reaction process 1 includes the portion of the process where all the necessary reaction components and reaction conditions are present such that the reaction can occur at a desired rate. Thus, the reaction system of reaction process 1 can include, at a minimum, the oligomerization reactor 50 (with or without internal and/or external heat exchange components), motive device 10, process lines 25, 26, 27, and 28, and optional heat exchanger 29. Depending upon the particular set-up, a portion of process line 30 after process valve 30a can also constitute part of the reaction system if the all the necessary reaction components and reaction conditions are present such that the reaction can occur at a desired rate in the portion of process line 30.

As shown in the embodiment of FIG. 1, the oligomerization reactor 50 can be a continuous stirred tank reactor (CSTR). In some embodiments, the oligomerization reactor can be a stirred tank reactor (e.g. a continuous stirred tank reactor, among others), a plug flow reactor, or any combination thereof; alternatively, a stirred tank reactor; or alternatively, a plug flow reactor. In other embodiments, the continuous reaction system can comprise different types of reactors in combination, and in various arrangements. When multiple oligomerization reactors are present, as described in more detail herein, each of the reactors can be the same or different types of reactors. In some embodiments, a CSTR can be configured to provide a mixed flow within the reactor. In an embodiment, a CSTR can include a mechanical agitator 16 to stir and/or create turbulent flow within the oligomerization reactor 50. Other suitable agitators which can be used in place of, or in conjunction with the mechanical agitator can include internal baffles, gas sparging, or any combination thereof. In general, the reaction mixture flowing through the reaction process 1 having any of the types of reactor described herein can be agitated or stirred by any means which can create turbulent flow through all or a portion of the reactor system as described herein. In some embodiments, the reaction mixture can be circulated through the reactor using a motive device. In other embodiments, the reaction mixture can be circulated through the reactor system and agitated or stirred using a motive device.

As the reaction mixture flows within reaction process 1, an oligomer product is produced. Reference to the "total reaction mixture volume" ($V_r$) is used herein to refer to the volume of the reaction mixture within the reaction system of reaction process 1. The reaction mixture generally refers to one or more phases in which the reaction within the reaction system of reaction process 1 is occurring. If the reaction system of reaction process 1 is completely full of the reaction mixture, the total reaction mixture volume can be the same as the volume of the reaction system of the reaction process 1. In some embodiments, portions of the reactor system can comprise a different phase or composition and/or one or more volumes or regions that do not include all the necessary components for reaction to occur. As a result, the total reaction mixture volume can be less than the volume of the reaction system of reaction process 1. For example, when the reaction mixture is in the liquid phase, the volume of a gas phase present within the oligomerization reactor 50 can be subtracted from the volume of the reaction system of the reaction process 1 when determining the total reaction mixture volume.

In order to control the temperature of the reaction mixture within the reaction process 1, various heat exchange surfaces can be used. The heat exchange within the reaction process 1 can allow a heat exchange medium to indirectly contact the reaction mixture to exchange heat between the heat exchange medium and the reaction mixture. Indirect contact refers to contact through a conductive material such as the wall of the reactor or heat exchanger without any direct contact or mixing between the two fluids. In an embodiment, one or more external heat exchange jackets 49 can be used with the oligomerization reactor 50. The jackets 49 can be configured to receive a heat exchange fluid through heat exchange medium inflow line 53 and pass the heat exchange fluid out of the jacket 49 through heat exchange medium outflow line 54. In some embodiments, the heat exchange fluid can comprise a liquid(s), a vapor(s), or combinations thereof. Generally, the heat exchange fluid can be any fluid capable of maintaining the desired reaction mixture (e.g., oligomerization mixture) temperature through heat exchange. Non-limiting examples of heat exchange fluid(s) can include those comprising water, glycol, or combinations thereof. In embodiments, the heat exchange medium inflow line 53 and heat exchange medium outflow line 54 can have flanges to connect to inlet and outlet piping.

The heat exchange fluid can be circulated through an annulus between the jacket 49 and the outer surface of the oligomerization reactor 50, for example. The circulation of the heat exchange fluid can remove heat produced by the reaction or add heat to maintain the reaction through the reactor wall. The heat exchange fluid can be circulated to an external heat exchange system before returning to the annular region in a heat exchange cycle. The jacket 49 may only cover a portion of the oligomerization reactor 50 and the intermediate regions may not be subject to heat transfer via jacket 49. In an embodiment, at least 10%, at least 20%, at least 30%, at least 40%, at least 50%, or at least 60% of the outer surface of the oligomerization reactor 50 can be subject to heat exchange.

Additional heat exchange surfaces can also be present in the reaction system of reaction process 1. As shown in FIG. 1, an internal heat exchange coil 48 can be used to supply or remove heat from within the oligomerization reactor 50. The heat exchange coil 48 can be supplied with a heat exchange fluid, for example, using a heat exchange fluid inlet line 51 and a heat exchange fluid outlet line 52.

One or more additional heat exchange structures including heat exchangers using heat exchange fluid and/or other process streams can be used to further control the temperature of the reaction mixture within the reaction system or reaction process 1. As shown in FIG. 1, a heat exchanger 29 can be used within the reaction loop to further control the temperature of the reaction mixture. For example, heat exchanger 29 can be used to control the temperature of the reaction mixture in process line 27 to produce a reaction mixture in line 28 having a changed temperature as compared to process line 27. The heat exchanger can provide heating or cooling using an external fluid including a heat exchange fluid and/or other process streams.

Figure 2:
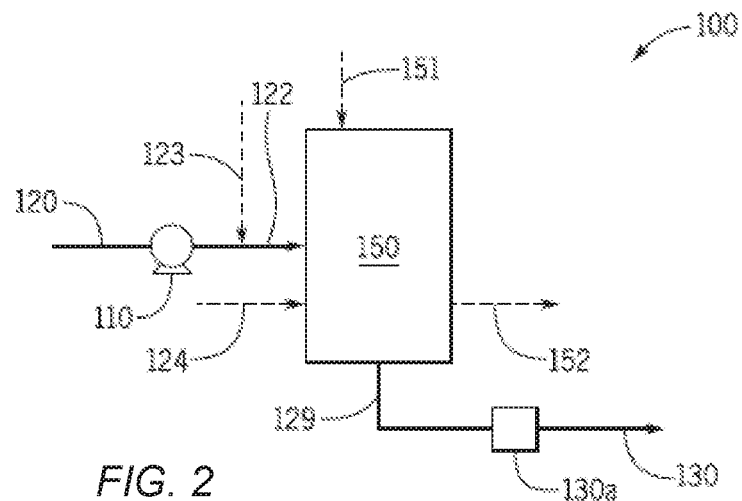
FIG. 2 illustrates an alternative embodiment of all or a portion of an oligomerization reaction process.

FIG. 2 illustrates an embodiment of reaction process 100 in accordance with the present disclosure including all or a portion of a reaction system and its associated feed inlets, effluent outlets, and other equipment. Specifically, FIG. 2 shows a view of a reaction process 100 having a single reactor 150. As can be seen, reaction process 100 has feed inlet 120 (which represents one or more feed lines of the reaction process 100) to feed one or more reaction components though feed valve or motive device 110 and through process line 122 into reactor 150. As a reaction mixture (described in more detail herein) flows within portions of reaction process 100 (including reactor 150, motive device 130a, and process line 129, among other reaction process 100 components), reaction product (described in more detail herein) is produced. Reactor effluent can exit reactor 150 via process line 129 through process valve or pump 130a into process line 130. Lines 151 and 152 represent heat exchange medium inflow and heat exchange medium outflow lines for optional heat exchange medium to flow through reactor 150 on lines separate from process lines containing the reaction mixture. Lines 123 and 124 show optional additional feed lines to feed reaction components to process lines or reactor 150, among other places.

Figure 3:
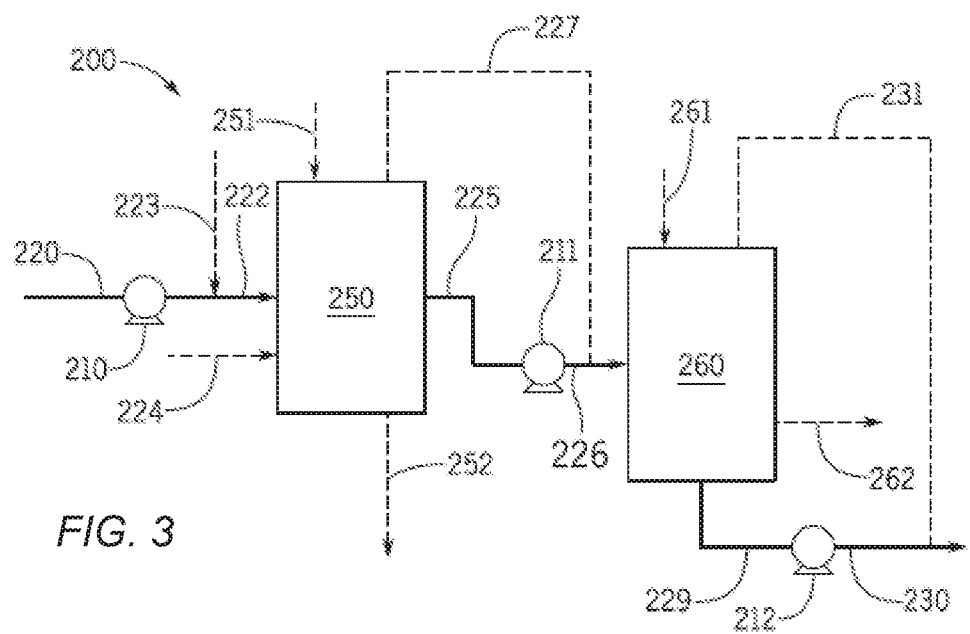
FIG. 3 illustrates an alternative embodiment of all or a portion of an oligomerization reactor system having two optional recycle loops.

FIG. 3 illustrates another embodiment of reaction process 200 in accordance with the present disclosure including all or a portion of a reaction system and its associated feed inlets, effluent outlets, and other equipment. Specifically, FIG. 3 shows a view of reaction process 200 having two reactors 250 and 260 connected in series. As can be seen, reaction process 200 has feed inlet 220 (which represents one or more feed lines of reaction process 200) to feed one or more reaction components through valve or motive device 210 and through process line 222 to reactor 250. As a reaction mixture (described in more detail herein) flows within reaction process 200 (including reactors 250 and 260, motive devices/valves 211 and 212, and process lines 225, 226, and 229, among other reaction process 200 components), reaction product (described in more detail herein) is produced. Reactor effluent can exit reactor 260 via process line 229 through process valve or pump 212 into process line 230. Lines 251 and 252 of reactor 250, and lines 261 and 262 of reactor 260 represent heat exchange medium inflow lines and heat exchange medium outflow lines for optional heat exchange medium to flow through reactors 250 and 260, respectively, on lines separate from process lines containing the reaction mixture. Lines 223 and 224 show optional additional feed lines to feed reaction components to process line 222 or reactor 250, respectively. Additional optional feed lines (not shown) can feed reaction components to process lines 225 and/or 226, and/or reactors 250 and/or 260, among other places. Optional process lines 227 and 231 represent process lines which can be utilized to recycle a portion of the reaction mixture through reactors 250 and 260 (respectively). The reaction mixture within optional process lines 227 and 231 can optionally be subjected to heat exchange using various heat exchange equipment (not shown) which can keep the reaction mixture separate from the heat exchange fluid medium.

Figure 4:
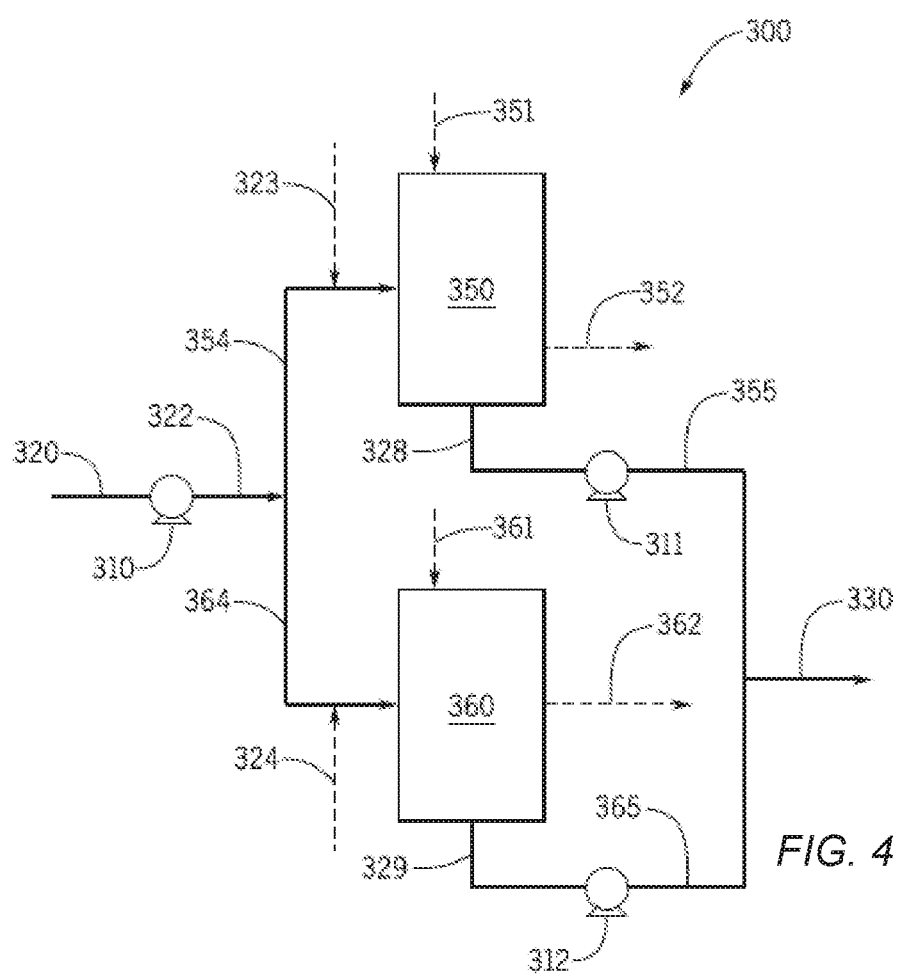
FIG. 4 illustrates an alternative embodiment of all or a portion of an oligomerization reaction process.

FIG. 4 shows a further embodiment of reaction process 300 in accordance with the present disclosure including all or a portion of a reaction system and its associated feed inlets, effluent outlets, and other equipment. Specifically, FIG. 4 shows a view of reaction process 300 having two reactors 350 and 360 connected in parallel. As can be seen, reaction process 300 has feed inlet 320 (which represents one or more feed lines of reaction process 300) to feed one or more reaction components through valve or motive device 310 and process line 322 to reactors 350 and 360 through process lines 354 and 364 (respectively). As a reaction mixture (described in more detail herein) flows within reaction process 300 (including reactors 350 and 360, motive devices/valves 311 and 312, and process lines 328, 329, 355, and 365, among other reaction process 300 components), reaction product (described in more detail herein) is produced. Reactor effluent can exit reactors 350 and 360 via process lines 328 and 329 (respectively) though valves or motive devices 311 and 312 (respectively) into process lines 355 and 365 (respectively) and can be combined into process line 330. Lines 351 and 352 of reactor 350, and lines 361 and 362 of reactor 360 represent heat exchange medium inflow lines and heat exchange medium outflow lines for optional heat exchange medium to flow through reactors 350 and 360, respectively, on lines separate from process lines containing the reaction mixture. Process lines 323 and 324 show optional additional feed lines to feed reaction components to the process lines 354 and 364 (respectively). Additional optional feed lines (not shown) can feed reaction components to process line 322, reactor 350, and/or reactor 360, among other places.

Figure 5:
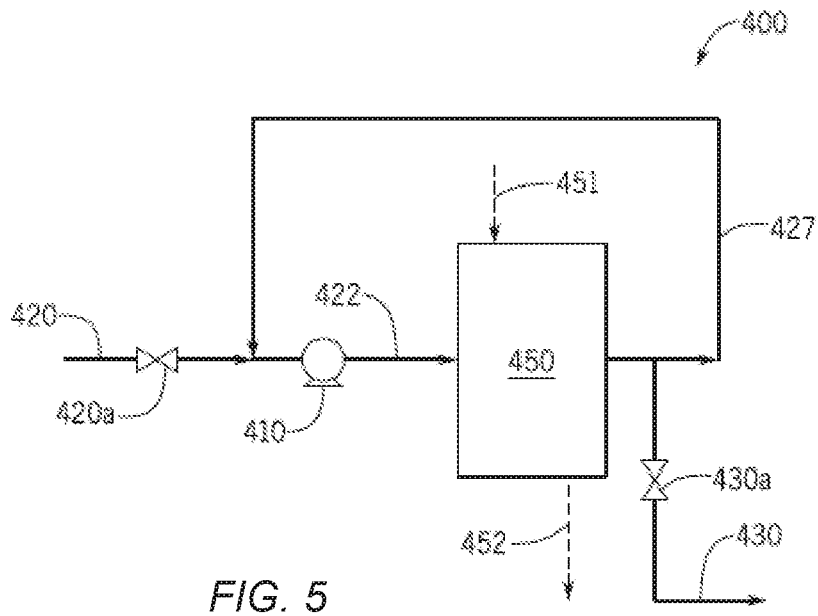
FIG. 5 illustrates an alternative embodiment of all or a portion of an oligomerization reaction process having a recycle loop.

FIG. 5 illustrates an embodiment of reaction process 400 in accordance with the present disclosure including all or a portion of a reaction system and its associated feed inlets, effluent outlets, and other equipment. Specifically FIG. 5 shows a view of a reaction process 400 having a single oligomerization reactor 450. As can be seen, reaction process 400 has feed inlet 420 (which represents one or more feed lines of reaction process 400) to feed one or more reaction components through valve or motive device 420a (operating on mass or volume control) to a reaction mixture. As the reaction mixture (described in more detail herein) flows through the loop including reactor 450, motive device 410, and process lines 422 and 427 (among other reaction process components) within reaction process 400, reaction product (described in more detail below) can be produced. Effluent can exit the loop through valve or motive device 430a (operating on mass control, volume control, or pressure control) into process line 430. Lines 451 and 452 of reactor 450 represent heat exchange medium inflow and heat exchange medium outflow lines for optional heat exchange medium to flow through reactor 450 on lines separate from process lines containing the reaction mixture (when included). Additional optional feed lines (not shown) can feed reaction components through a valve or a motive device (operating on mass or volume control) to process line 422, process line 427, and/or reactor 450, among other places, in place of or in addition to feed inlet 420.

Figure 6:
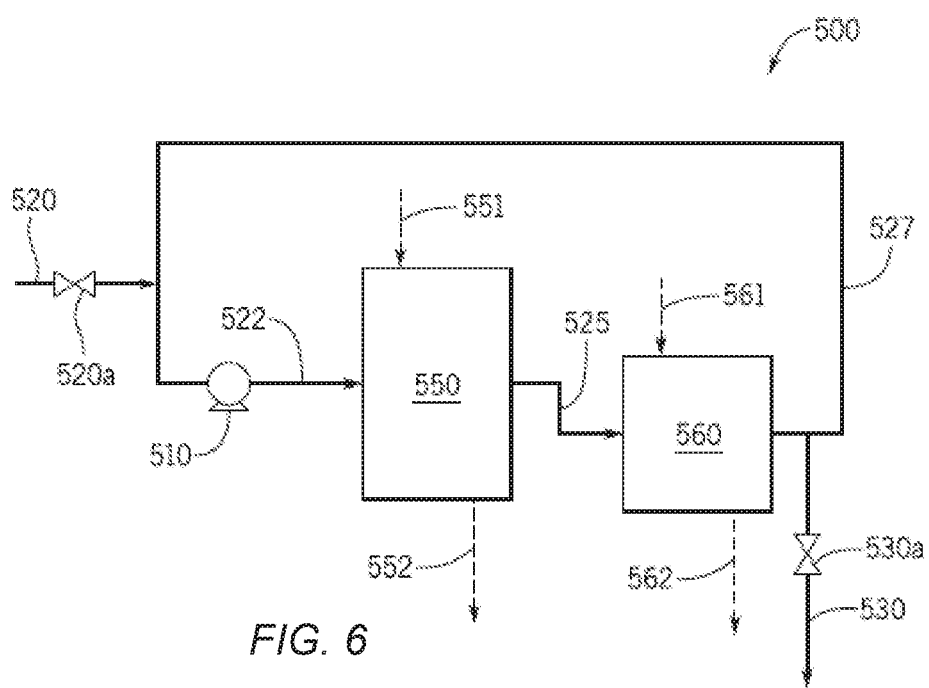
FIG. 6 illustrates an alternative embodiment of all or a portion of an oligomerization reaction process having a recycle loop.

FIG. 6 illustrates an embodiment of reaction process 500 in accordance with the present disclosure including all or a portion of a reaction system and its associated feed inlets, effluent outlets, and other equipment. Specifically, FIG. 6 shows a view of reaction process 500 having two reactors 550 and 560 connected in series. As can be seen, reaction process 500 has feed inlet 520 (which represents one or more feed lines of reaction process 500) to feed one or more reaction components through valve or pump 520a (operating on mass or volume control) to a reaction mixture. As the reaction mixture (described in more detail herein) flows through a loop including reactors 550 and 560, motive device 510, and process lines 522, 525 and 527 (among other reaction process components) within reaction process 500, reaction product (described in more detail herein) can be produced. Effluent can exit the loop through valve or motive device 530a (operating on mass control, volume control, or pressure control) into process line 530. Lines 551 and 552 of reactor 550, and lines 561 and 562 of reactor 560 represent heat exchange medium inflow lines and heat exchange medium outflow lines for optional heat exchange medium to flow through reactors 550 and 560, respectively, on lines separate from process lines containing the reaction mixture. Additional optional feed lines (not shown) can feed reaction components through a valve or a motive device (operating on mass or volume control) to process line 522, process line 525, process line 527, reactor 550, and/or reactor 560, among other places, in place of or in addition to feed inlet 520.

Figure 7:
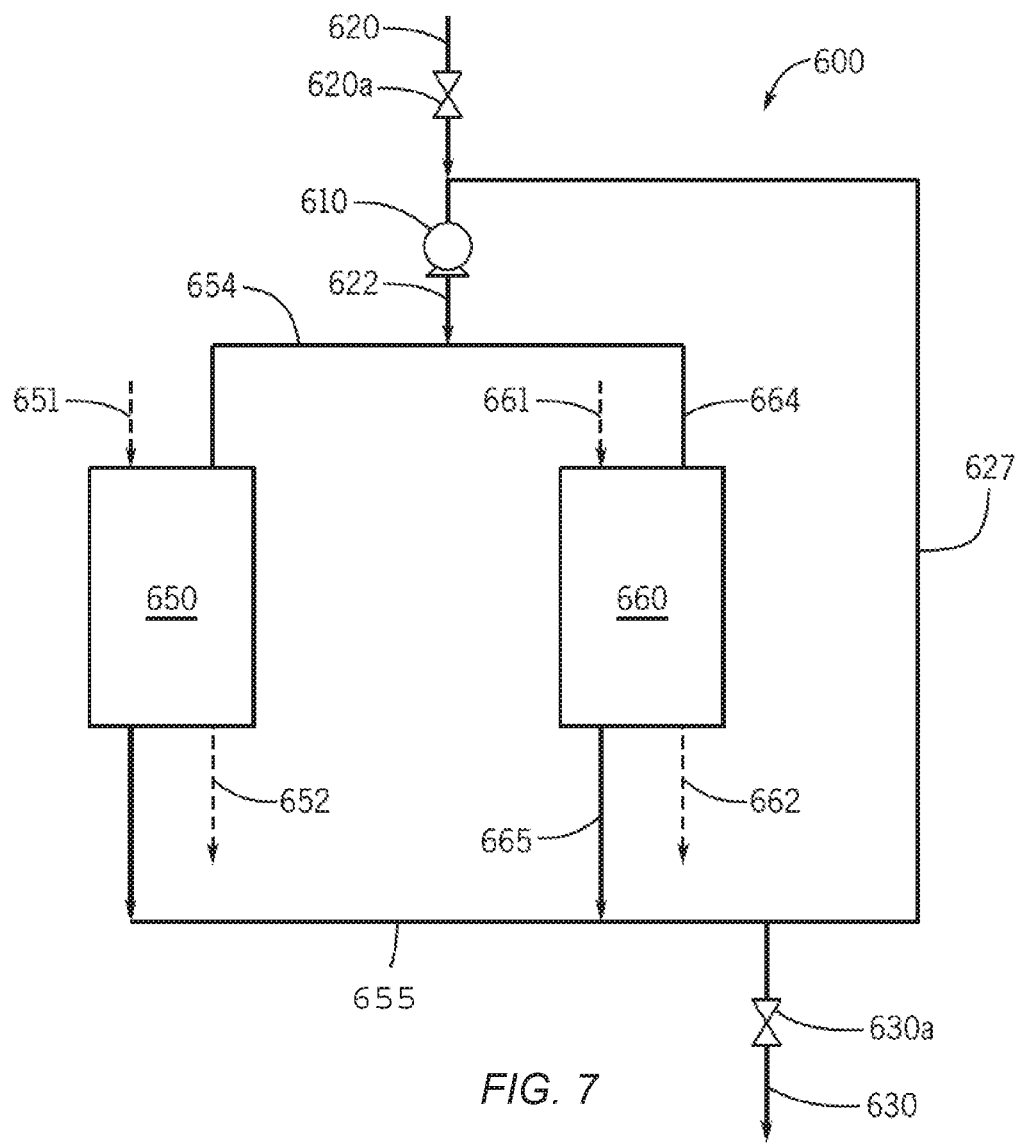
FIG. 7 illustrates an alternative embodiment of all or a portion of an oligomerization reaction process having a recycle loop.

FIG. 7 shows an embodiment of reaction process 600 in accordance with the present disclosure including all or a portion of a reaction system and its associated feed inlets, effluent outlets, and other equipment. Specifically, FIG. 7 shows a view of reaction process 600 having two reactors 650 and 660 connected in parallel. As can be seen, reaction process 600 has feed inlet 620 (which represents one or more feed lines of reaction process 600) to feed one or more reaction components through a valve or motive device 620a (operating on mass or volume control) to a reaction mixture. As the reaction mixture (described in more detail herein) flows through a loop including reactors 650 and 660, motive device 610, and process lines 622, 654, 664, 655, 665, and 627 (among other reaction process components) within reaction process 600, reaction product (described in more detail herein) can be produced. Effluent can exit the loop through valve or motive device 630a (operating on mass control, volume control, or pressure control) into process line 630. Lines 651 and 652 of reactor 650, and lines 661 and 662 of reactor 660 represent heat exchange medium inflow lines and heat exchange medium outflow lines for optional heat exchange medium to flow through reactors 650 and 660, respectively, on lines separate from process lines containing the reaction mixture. Additional optional feed lines (not shown) can feed reaction components through a valve or a motive device (operating on mass or volume control) to process line 622, process line 654, process line 664, process line 627, reactor 650, and/or reactor 660, among other places, in place of or in addition to feed inlet 620.

Generally, reaction processes utilizing a reactor in accordance with the present disclosure (e.g., reaction processes 1, 100, 200, 300, 400, 500, and 600, described herein, among other reaction process designs), circulates a reaction mixture within or through reactors and process lines using a motive device to produce a reaction product. Feeds to the reaction process can be introduced (either continuously or semi-continuously) through one or more feed inlets while effluent can be removed using one or more discharges. In embodiments utilizing a heat exchange medium for controlling the temperature of the reaction mixture (e.g., for removing heat produced by the reaction, or to add heat to the reaction), at least a portion of a reaction process (e.g., all or a portion of the reactors) can have a heat exchange configuration. In such embodiments, a heat exchange medium can be provided via one or more heat exchange medium inflow lines and removed via one or more heat exchange medium outflow lines which keep the reaction mixture separate from the heat exchange fluid medium.

The reaction mixture flowing through the reactor(s) can be agitated or stirred by any means which can create turbulent flow through all or a portion of the reaction system. For example the reaction mixture flowing through the reaction system can be agitated or stirred by: 1) the introduction of an inert gas (e.g., nitrogen purge) in a manner that can cause agitation, 2) introducing one or more reaction mixture feeds to the reaction system in a manner that can cause agitation, 3) removing effluent from the reaction system in a manner that can cause agitation, 4) by mechanical or magnetic stirring according to methods known in the art with the aid of this disclosure, 5) by using a motive device to circulate the reaction mixture through the reaction system, or 6) combinations thereof. In some embodiments, the reaction mixture can be circulated through the reactor or reaction system using a motive device. In other embodiments, the reaction mixture can be circulated through the reactor or reaction system and agitated or stirred using a motive device.

A feed device (e.g., motive device or valve 20a of FIG. 1, motive device or valve 110 of FIG. 2, motive device or valve 210 of FIG. 3, motive device or valve 310 of FIG. 4, motive device or valve 420a of FIG. 5, motive device or valve 520a of FIG. 6, or motive device or valve 620a of FIG. 7, in addition to other feed devices that are not shown), can continuously (alternatively, intermittently) provide reaction components of the reaction mixture to the reaction system (including one or more of the reactors, e.g., reactor 50 of FIG. 1, reactor 150 of FIG. 2, reactors 250 and 260 of FIG. 3, reactors 350 and 360 of FIG. 4, reactor 450 of FIG. 5, reactors 550 and 560 of FIG. 6, or reactors 650 and 660 of FIG. 7, among other reaction system components). A motive device (e.g., motive device 10 of FIG. 1, motive device 410 of FIG. 5, motive device 510 of FIG. 6, or motive device 610 of FIG. 7), can continuously (alternatively, intermittently) circulate the reaction mixture through the loop (including one or more of the reactors, e.g., reactor 50 of FIG. 1, reactor 450 of FIG. 5, reactors 550 and 560 of FIG. 6, or reactors 650 and 660 of FIG. 7, among other reaction system components). While reaction processes 1, 100, 200, 300, 400, 500, and 600 as shown in FIGS. 1 to 7 show one or two reactors, it is contemplated any number of reactors (e.g., 1, 2, 3, 4, 5, 6, 7, 8, 9, 10, or greater) can be used for one or more of the embodiments disclosed herein.

The reaction mixture comprising the reaction product can be withdrawn from the reactor or loop for further processing (e.g., catalyst system deactivation and isolation of the reaction product, among other processing steps). For example, reaction mixture can be withdrawn from reactor 150 of FIG. 2, reactor 260 of FIG. 3, or reactors 350 and 360 of FIG. 4) or loop (e.g., loop including reactor 50 of FIG. 1, loop including reactor 450 of FIG. 5, loop including reactors 550 and 560 of FIG. 6, or loop including reactors 650 and 660 of FIG. 7) through a reactor outlet valve or motive device (e.g., reactor outlet valve or motive device 130a of FIG. 2, reactor outlet valve or motive device 212 of FIG. 3, or reactor outlet valves or motive devices 311 and 312 of FIG. 4) or a loop outlet valve or pump (e.g., loop valve or motive device 30a of FIG. 1, loop valve or motive device 430a of FIG. 5, loop valve or motive device 530a of FIG. 6, or loop valve or motive device 630a of FIG. 7). The reactor outlet valve or pump, or loop outlet valve or motive device can semi-continuously, or alternatively continuously, remove a portion of the reaction mixture from the reactor or loop (e.g., a valve can be moved or actuated between a closed position and an open position so that a portion of the reaction mixture flows through the valve and into reactor or loop discharge line).

At least a portion of the components of the reaction mixture can react (e.g., via one or more reaction processes) to form a reaction product. The compositional identity of the reaction mixture can vary as the reaction mixture travels through the reaction system. As reaction proceeds, reactants can be consumed, reaction components can be fed to the reaction system, a portion of the reaction mixture can be removed from the reactor or loop, and/or reaction products can be formed. In embodiments, the reaction mixture can comprise a liquid phase, a vapor phase, or combinations thereof. In some embodiments, the reaction mixture can be homogenous or heterogeneous. In other embodiments, the reaction mixture can have one liquid phase or more than one liquid phase.

The reactors disclosed herein (e.g., reactor 50 of FIG. 1, reactor 150 of FIG. 2, reactors 250 and 260 of FIG. 3, reactors 350 and 360 of FIG. 4, reactor 450 of FIG. 5, reactors 550 and 560 of FIG. 6, reactors 650 and 660 of FIG. 7) can be utilized in a continuous or semi-continuous process comprising continuously or semi-continuously introducing one or more feeds to the reaction system (e.g., via feed inlet 20 of FIG. 1, feed inlet 120 of FIG. 2, feed inlet 220 of FIG. 3, feed inlet 320 of FIG. 4, feed inlet 420 of FIG. 5, feed inlet 520 of FIG. 6, feed inlet 620 of FIG. 7, in addition to other feed inlets that are not shown), flowing the reaction mixture through the reactor(s) (and other reaction system elements), and continuous or semi-continuously removing the reaction mixture from the reactor (e.g., via loop discharge valve or motive device 30a of FIG. 1, process line 129 of FIG. 2, process line 229 of FIG. 3, process lines 328 and 329 of FIG. 4, loop discharge valve or motive device 430a of FIG. 5, loop discharge valve or motive device 530a of FIG. 6, loop discharge valve or motive device 630a of FIG. 7) as described herein. Alternatively, a batch loop process can also be employed comprising circulating the reaction mixture through the reactor(s) (e.g., reactor 50 of FIG. 1, reactor 450 of FIG. 5, reactors 550 and 560 of FIG. 6, reactors 650 and 660 of FIG. 7) until the reaction is complete (which is not necessarily the point at which one or more reagents are completely consumed), and then removing the contents (e.g., reaction mixture) from the reactor(s).

FIGS. 2-7 include optional heat exchange medium inflow and optional heat exchange medium outflow lines for optional heat exchange medium to flow through the respective reactor (e.g., process lines 151 and 152 for reactor 150, process lines 251 and 252 for reactor 250, process lines 261 and 262 for reactor 260, process lines 351 and 352 for reactor 350, process lines 361 and 362 for reactor 360, process lines 451 and 452 for reactor 450, process lines 551 and 552 for reactor 550, process lines 561 and 562 for reactor 560, process lines 651 and 652 for reactor 650, and process lines 661 and 662 for reactor 660) can be considered analogous or equivalent to the heat exchange medium inflow line 51 and heat exchange medium outflow line 52, respectively, for the internal heat exchange coils 48 in FIG. 1. However, the optional heat exchange medium inflow line and heat exchange medium outflow line for the reactors in FIGS. 2-7 can be heat exchange medium inflow lines and heat exchange medium outflow lines for internal heat exchange coils, heat exchange medium inflow lines and heat exchange medium outflow lines for an external heat exchange around the reactors, heat exchange medium inflow lines and heat exchange medium outflow lines for any other type of reactor design which allows for heat exchange between a reaction mixture and a heat exchange medium via indirect contact, which refers to contact through a conductive material. It should also be noted that while FIGS. 2-7 do not show a separate heat exchanger similar to heat exchange 29 in FIG. 1, the use of one or more heat exchangers similar to heat exchange 29 of FIG. 1 on one or more process lines in any reaction process 100, 200, 300, 400, 500, and/or 600 of FIG. 2-7 is contemplated by the present disclosure.

The reaction process described herein can be carried out at any suitable conditions. The temperature of the reaction mixture of any process described herein can be controlled during the operation of the reaction system. The heat exchange surfaces within the reaction system can be used to maintain a desired temperature range. As noted herein, the heat exchange with the reaction mixture occurs across a heat exchange surface, and the heat transfer rate can depend on the relative temperature difference between the heat exchange fluid and the reaction mixture. As used herein, the "heat exchanged surface area" refers to the process side surface area within a heat exchanged section of the reaction system in contact with the reaction mixture. In an embodiment, the heat exchanged surface area for a portion of the oligomerization reactor subject to heat exchange can be provided through an external jacket (e.g., external jacket 49 of FIG. 1). $A_j$, refers to the surface area of the interior surface of the oligomerization reactor in contact with the reaction mixture (e.g., the process side surface area), where the interior surface of the reactor corresponds to an exterior surface of the oligomerization reactor in contact with the heat exchange medium. When an internal heat exchange device (e.g., the heat exchange coils 48 of FIG. 1) is used, the heat exchanged surface area, $A_c$, includes the exterior surface area of the internal heat exchange device in contact with the reaction mixture. When a separate heat exchange device (e.g., the heat exchanger 29 of FIG. 1) is used, the heat exchanged surface area, $A_{he}$, includes the exterior surface area of the internal heat exchange device in contact with the reaction mixture. The total heat exchanged surface area, $A_{het}$, includes the total of the heat exchanged surface areas in all of the heat exchanged sections within the reaction system. For example, in the embodiment illustrated in FIG. 1, the total heat exchanged surface area ($A_{het}$), includes the interior surface area of the oligomerization reactor 50 corresponding to the area within the jacket 49 in contact with the reaction mixture (A), the exterior surface area of the heat exchange coils 48 in contact with the reaction mixture (At), and the interior surface area of the process lines within the heat exchanger 29 in contact with the reaction mixture ($A_{he}$).

The volume of the reaction mixture within the heat exchanged sections can be referred to as the "heat exchanged reaction mixture volume." This volume is defined as the volume of the reaction mixture within the heat exchanged sections. For a cylindrical portion of the reactor system, the heat exchanged reaction mixture volume includes the interior volume of the cylinder having theoretical end planes at the location at which the heat exchanged surface area ends. The total volume of the reaction mixture within the heat exchanged portion of the reaction system, $A_{het}$, includes all of the volume of the reaction mixture subjected to heat exchange in the reaction system. For example, in the embodiment illustrated in FIG. 1, the total volume of the reaction mixture within the heat exchanged sections of the reaction system, $V_{het}$, can include, the volume of the reaction mixture heat exchanged via an oligomerization reactor jacket (e.g., external jacket 49 of FIG. 1), $V_j$, the volume of the reaction mixture heat exchanged via heat exchange coils within an oligomerization reactor (e.g., internal coils 48 of FIG. 1), $V_c$, and/or the volume of the reaction mixture within the process lines of a heat exchanger (e.g., heat exchanger 29 of FIG. 1), $V_{he}$. It should be noted that all or a portion of the heat exchange portion of an oligomerization reactor can be heat exchanged with more than one heat exchange device. For example all or a portion of the heat exchanged volume of the reaction mixture within an oligomerization reactor can be heat exchanged by an external oligomerization reactor jacket and internal heat exchange coils. In this scenario, the volume of the heat exchanged reaction mixture which is heat exchanged by multiple heat exchange volumes is to be only counted once in the determination of the heat exchange volume of the reaction mixture. Additionally, the heat exchanged reaction mixture volume may not include any portion of the heat exchanged volume that does not comprise the reaction mixture.

The reaction system can have a ratio of the heat exchanged reaction mixture volume, $V_{her}$, to the total reaction mixture volume selected to maintain a desired temperature and/or temperature profile of the reaction mixture within the reaction system. In an embodiment, the minimum ratio of the heat exchanged reaction mixture volume, $V_{her}$, to the total reaction mixture volume, $V_r$, can be greater than or equal to 0.7, greater than or equal to 0.75, or greater than or equal to 0.8. In an embodiment, the maximum ratio of the heat exchanged reaction mixture volume to the total reaction mixture volume can be less than or equal to 1.0, less than or equal to 0.975, less than or equal to 0.95, less than or equal to 0.925, or less than or equal to 0.9. In an embodiment, the ratio of the heat exchanged reaction mixture volume, $V_{her}$, to the total reaction mixture volume, $V_r$, can range from any minimum ratio of the heat exchanged reaction mixture volume, $V_{her}$, to the total reaction mixture volume, $V_r$, described herein to any maximum ratio of the heat exchanged reaction mixture volume, $V_{her}$, to the total reaction mixture volume, $V_r$, described herein. In some embodiments, suitable ranges for the ratio of the heat exchanged reaction mixture volume, $V_{her}$, to the total reaction mixture volume, $V_r$, can include, but are not limited to, from 0.7 to 1.0, from 0.75 to 1, from 0.8 to 1, from 0.75 to 0.975, from 0.75 to 0.95, from 0.8 to 0.975, from 0.8 to 0.95, or from 0.8 to 0.925. Other suitable ranges for the ratio of the heat exchanged reaction mixture volume, $V_{her}$, to the total reaction mixture volume, $V_r$, are readily apparent from the present disclosure.

The heat exchanged surface area and/or the heat exchanged reaction mixture volume does not include the surface area or volume, respectively, of any portion of the reactor system that is not subject to heat exchange (e.g., that is not subject to heat exchange with a heat exchange medium). While some amount of heat exchange can be expected in the remaining portions due to heat loss or gain through the walls of the reactor, motive device, and/or process lines, such heat loss or gain is generally minimal and negligible relative to the heat loss or gain within the heat exchanged sections. These portions of the reactor can be referred to herein as non-heat exchanged sections. As with the heat exchanged surface area, the "non-heat exchanged surface area" refers to the process side surface area within a non-heat exchanged section of the reaction system in contact with the reaction mixture. The total non-heat exchanged surface area includes the total of the non-heat exchanged surface areas in all of the non-heat exchanged sections within the reactor system.

The volume of the reaction mixture within the non-heat exchanged sections can be referred to as the "non-heat exchanged reaction mixture volume." This volume is defined as the volume of the reaction mixture within the non-heat exchanged sections. The non-heat exchanged reaction mixture volume does not include any portion of the non-heat exchanged volume that does not comprise the reaction mixture.

The reaction within the reaction system can be carried out while controlling the temperature differences between the temperature of the reaction mixture in the heat exchanged sections, the temperature of the reaction mixture in the non-heat exchanged sections, and the temperature of the heat exchange fluid or medium. When the reaction mixture flows through the reaction system, it is believed that the fluid flow can create sufficient turbulence to create a relatively uniform temperature profile of the reaction mixture across the flow path. In an embodiment, the average temperature of the reaction mixture within any portion of the reaction system refers to the bulk temperature of the reaction mixture at a given location. The reaction temperature of the reaction mixture can be measured at any point along the flow path of the reaction system.

In some embodiments, the reaction temperature can be reported as an average of the temperature measurements measured at any point along the reaction system. An average temperature of the reaction mixture within the non-heat exchanged portion of the reaction system refers to the average of one or more temperatures taken along the flow path of the reaction mixture in the non-heat exchanged section of the reaction system. Similarly, an average temperature of the reaction mixture within the heat exchanged portion of the reaction system refers to the average of one or more temperatures taken along the flow path of the reaction mixture in the heat exchanged section of the reaction system.

In an embodiment, the average temperature of the reaction mixture within a non-heat exchanged section of the reaction system can be within 0.61%, within 0.53%, within 0.46%, within 0.38%, within 0.31%, within 0.27%, within 0.24%, or within 0.21% of the average temperature of the reaction mixture within a heat exchanged section of the reaction system. The percentage values refer to a comparison of the temperatures on an absolute temperature scale (i.e., K or ° R). Further, the reference to a non-heat exchanged section and/or a heat exchanged section can refer to any non-heat exchanged section and/or a heat exchanged section in the reaction system.

The temperature difference between the reaction mixture within a heat exchanged section and the heat exchange medium within the same heat exchanged section can also be controlled to limit the temperature differentials between the reaction mixture and heat exchange medium that are in indirect contact through a conductive material such as the wall of the reactor or heat exchanger without any direct contact or mixing between the two fluids in the heat exchanged sections (or in other words the temperature differential between the heat exchange fluid and the reaction mixture). The average temperature of the heat exchange medium in a heat exchanged section refers to the average temperature of the heat exchange medium within the heat exchanger. In an embodiment, the average temperature of the heat exchange medium within a heat exchanged section can be within 9.3%, within 7.6%, within 6.1%, within 5.3%, or within 4.6% of the average temperature of the reaction mixture in the heat exchanged section of the reactor system. The percentage values refer to a comparison of the temperatures on an absolute temperature scale (i.e., K or ° R).

During operation, the components fed to the reaction mixture (e.g., an olefin monomer, a catalyst system, catalyst system components, and/or solvent/diluent, among other potential components as described in more detail herein) can be periodically or continuously introduced into the reaction system. At least a portion of the components fed to the reaction mixture can react (e.g., via one or more reaction processes) to form a reaction product. The compositional identity of the reaction mixture can vary as the reaction mixture travels through the reaction system, as reactants are consumed, as reaction components are fed to the reaction system, as reaction mixture is continuously or periodically removed from the reaction system, and/or as reaction products are formed. In some embodiments, the reaction mixture can comprise a liquid phase, a vapor phase, a solid phase, or combinations thereof; alternatively, a liquid phase, and a vapor phase; or alternatively, a solid phase, and a liquid phase. In some embodiments, the reaction mixture can be homogenous or heterogeneous; alternatively, homogeneous; or alternatively heterogeneous. In other embodiments, the liquid phase of the reaction mixture can have one liquid phase or more than one liquid phase; alternatively, one liquid phase; or alternatively more than one liquid phase.

As the reaction process proceeds, the reaction mixture can flow through the reaction system. The reaction mixture flow can be turbulent in one or more portions of the reaction system such as the heat exchanged section(s). The turbulent flow can be characterized by a Reynolds number within each section of the reaction system. In an embodiment, the reaction mixture flowing through a heat exchanged section can have a minimum Reynolds number of at least $1 \times 10^5$, $2 \times 10^5$, $3 \times 10^5$, or $4 \times 10^5$. In some embodiments, the maximum Reynolds number can be less than or equal to $3 \times 10^6$, $2 \times 10^6$, or $1 \times 10^6$. In an embodiment, the Reynolds number can range from any minimum Reynolds number described herein to any maximum Reynolds number described herein. In some embodiments, suitable ranges for the Reynolds number can include, but are not limited to, from $1 \times 10^5$ to $3 \times 10^6$, $1 \times 10^5$ to $2 \times 10^6$, $2 \times 10^5$ to $3 \times 10^6$, $2 \times 10^5$ to $2 \times 10^6$, $3 \times 10^5$ to $2 \times 10^6$, $3 \times 10^5$ to $1 \times 10^6$, $4 \times 10^5$ to $2 \times 10^6$, or $4 \times 10^5$ to $1 \times 10^6$. Other suitable ranges for the Reynolds number are readily apparent from the present disclosure. The reaction mixture flowing through a non-heat exchange portion of the reaction system can have a flow characterized by a similar Reynolds number range or the flow can be more turbulent (e.g., having a higher Reynolds number) or can be less turbulent (e.g., having a lower Reynolds number).

The effluent removal rate from the reaction system can be characterized by a reaction product discharge rate (e.g., an oligomerization product, trimerization product, tetramerization product, or a trimerization and tetramerization product). In an embodiment, the reaction product discharge rate can be expressed as amount of reaction product per unit of time discharged from the reaction system per reaction mixture volume of the reaction system. The reaction product discharge rate can be expressed in units of pounds of reaction product per hour discharged from the reaction system per gallon reaction mixture volume of the reaction system ("(lb)(hr$^{-1}$)(gal$^{-1}$)", which can also be expressed as "lb/hr/gal"). The reaction product discharge rate can be affected by selecting the various operating parameters including the rate of removal of the reaction mixture, the operating conditions, and the residence time of the reaction mixture within the reactor system.

In an embodiment, the reaction system(s) described herein can have an minimum reaction product (e.g., an oligomerization product, trimerization product, tetramerization product, or a trimerization and tetramerization product) discharge rate from the reaction system of at least 1.0 (lb)(hr$^{-1}$)(gal$^{-1}$), 1.5 (lb)(hr$^{-1}$)(gal$^{-1}$), 2 (lb)(hr$^{-1}$)(gal$^{-1}$), 2.25 (lb)(hr$^{-1}$)(gal$^{-1}$), or 2.5 (lb)(hr$^{-1}$)(gal$^{-1}$). In some embodiments, the reaction system(s) described herein can have a reaction product (e.g., an oligomerization product, trimerization product, tetramerization product, or a trimerization and tetramerization product) discharge rate from the reaction system that is less than or equal to 6 (lb)(hr$^{-1}$)(gal$^{-1}$), 5.5 (lb)(hr$^{-1}$)(gal$^{-1}$), 5.0 (lb)(hr$^{-1}$)(gal$^{-1}$), 4.75 (lb)(hr$^{-1}$)(gal$^{-1}$), or 4.5 (lb)(hr$^{-1}$)(gal$^{-1}$). In an embodiment, the reaction product (e.g., an oligomerization product, trimerization product, tetramerization product, or a trimerization and tetramerization product) discharge rate from the reaction system can range from any minimum reaction product (e.g., an oligomerization product, trimerization product, tetramerization product, or a trimerization and tetramerization product) discharge rate from the reaction system described herein to any maximum reaction product (e.g., an oligomerization product, trimerization product, tetramerization product, or a trimerization and tetramerization product) discharge rate from the reaction system described herein. In some embodiments, suitable ranges for the reaction product (e.g., an oligomerization product, trimerization product, tetramerization product, or a trimerization and tetramerization product) discharge rate from the reaction system can include, but are not limited to, from 1.0 (lb)(hr$^{-1}$)(gal$^{-1}$) to 6.0 (lb)(hr$^{-1}$)(gal$^{-1}$), from 1.5 (lb)(hr$^{-1}$)(gal$^{-1}$) to 5.5 (lb)(hr$^{-1}$)(gal$^{-1}$), from 2.0 (lb)(hr$^{-1}$)(gal$^{-1}$) to 5.0 (lb)(hr$^{-1}$)(gal$^{-1}$), from 2.25 (lb)(hr$^{-1}$)(gal$^{-1}$) to 4.75 (lb)(hr$^{-1}$)(gal$^{-1}$), or from 2.5 (lb)(hr$^{-1}$)(gal$^{-1}$) to 4.5 (lb)(hr$^{-1}$)(gal$^{-1}$). Other suitable ranges for the reaction product (e.g., an oligomerization product, trimerization product, tetramerization product, or a trimerization and tetramerization product) discharge rate from the reaction system are readily apparent from the present disclosure.

In some embodiments, the reaction system can include a line to pass fluid through a reaction loop (e.g., a reaction loop including reactor 50 of FIG. 1, reactor 250 of FIG. 3, reactor 260 of FIG. 3, reactor 450 of FIG. 5, reactors 550 and 560 of FIG. 6, or reactors 650 and 660 of FIG. 7). The fluid flowing through the reaction loop can be characterized by a volumetric reaction mixture recycle flow rate, which can include the volumetric flow rate of the reaction mixture passing through one or more reaction loops. In an embodiment, a maximum ratio of the volumetric reaction mixture recycle flow rate to the volumetric reaction system reaction mixture discharge rate (or reaction system reaction mixture discharge rate) can be at least 8, 10, 2, 14, or 16. In an embodiment, a minimum ratio of the volumetric reaction mixture recycle flow rate to the volumetric reaction system reaction mixture discharge rate (or reaction system reaction mixture discharge rate) can be less than or equal to 60, less than or equal to 50, less than or equal to 40, less than or equal to 36, less than or equal to 32, less than or equal to 30, less than or equal to 28, or less than or equal to 26. In an embodiment, the ratio of the volumetric reaction mixture recycle flow rate to the volumetric reaction system reaction mixture discharge rate (or reaction system reaction mixture discharge rate) can range from any minimum ratio of the volumetric reaction mixture recycle flow rate to the volumetric reaction system reaction mixture discharge rate (or reaction system reaction mixture discharge rate) described herein to any maximum ratio of the volumetric reaction mixture recycle flow rate to the volumetric reaction system reaction mixture discharge rate (or reaction system reaction mixture discharge rate) described herein. In some embodiments, suitable ranges for the ratio of the volumetric reaction mixture recycle flow rate to the volumetric reaction system reaction mixture discharge rate (or reaction system reaction mixture discharge rate) can include, but are not limited to, from 8 to 60, from 12 to 50, from 14 to 40, from 16 to 28, from 20 to 26, or from 16 to 20. Other suitable ranges for the ratio of the volumetric reaction mixture recycle flow rate to the volumetric reaction system reaction mixture discharge rate (or reaction system reaction mixture discharge rate) are readily apparent from the present disclosure.

The reaction process can be carried out under specific process condition(s) and/or process condition range(s). In an embodiment, the reaction process can be carried out so that a ratio of the total heat exchanged surface area of the reaction system to a total reaction mixture volume within the reaction system can be at least 0.75 in$^{-1}$, 1 in$^{-1}$, or 1.25 in$^{-1}$. In an embodiment, the reaction process can be carried out so that a ratio of the total heat exchanged surface area of the reaction system to a total reaction mixture volume within the reaction system is less than or equal to 5 in$^{-1}$, 4 in$^{-1}$, or 3.5 in$^{-1}$. In an embodiment, the ratio of the total heat exchanged surface area of the reaction system to a total reaction mixture volume within the reaction system can range from any minimum ratio of the total heat exchanged surface area of the reaction system to a total reaction mixture volume within the reaction system described herein to any maximum ratio of the total heat exchanged surface area of the reaction system to a total reaction mixture volume within the reaction system described herein. In some embodiments, suitable ranges for the ratio of the total heat exchanged surface area of the reaction system to a total reaction mixture volume within the reaction system can include, but are not limited to, from 0.75 in$^{-1}$ to 5 in$^{-1}$, from 1 in$^{-1}$ to 4 in$^-$, or from 1.25 in$^{-1}$ to about 3.5 in$^{-1}$. Other suitable ranges for the ratio of the total heat exchanged surface area of the reaction system to a total reaction mixture volume within the reaction system are readily apparent from the present disclosure.

The operation of the reaction process can be affected by the selection of the total reaction system heat exchanged surface area and the total reaction mixture volume, as well as the reaction product (e.g., an oligomerization product, trimerization product, tetramerization product, or a trimerization and tetramerization product) discharge rate from the reaction system. In an embodiment, the reaction system can be operated to perform a reaction process in a range defined by: 1) a ratio of the total reaction system heat exchanged surface area to the total reaction mixture volume and 2) the reaction product discharge rate from the reaction system. As described herein the ratio of the total reaction system heat exchanged surface area to the total reaction mixture volume and the reaction product discharge rate from the reaction system can have any minimum and/or maximum values described herein or range from any minimum value described herein to any maximum value described herein. In other embodiments, the ratio of the total reaction system heat exchanged surface area to the total reaction mixture volume and the reaction product discharge rate from the reaction system can be further selected to have values satisfying a lower boundary equation of the ratio of the total reaction system heat exchanged surface area to the total reaction mixture volume≥[0.64*(reaction product discharge rate from the reaction system)]−1.16; alternatively, satisfying a lower boundary equation of the ratio of the total reaction system heat exchanged surface area to the total reaction mixture volume≥[0.64*(reaction product discharge rate from the reaction system)]−1.00; alternatively satisfying a lower boundary equation of the ratio of the total reaction system heat exchanged surface area to the total reaction mixture volume≥[0.64*(reaction product discharge rate from the reaction system)]−0.84; alternatively, satisfying a lower boundary equation of the ratio of the total reaction system heat exchanged surface area to the total reaction mixture volume≥[0.64*(reaction product discharge rate from the reaction system)]−0.68; alternatively, satisfying a lower boundary equation of the ratio of the total reaction system heat exchanged surface area to the total reaction mixture volume≥[0.64*(reaction product discharge rate from the reaction system)]−0.52; or alternatively, satisfying a lower boundary equation of the ratio of the total reaction system heat exchanged surface area to the total reaction mixture volume≥[0.64*(reaction product discharge rate from the reaction system)]−0.36. In other embodiment, the ratio of the total reaction system heat exchanged surface area to the total reaction mixture volume and the reaction product discharge rate from the reaction system can be further selected to have values satisfying an upper boundary equation where the ratio of the total reaction system heat exchanged surface area to the total reaction mixture volume≤[0.64*(reaction product discharge rate from the reaction system)]+0.76; alternatively, satisfying an upper boundary equation of the ratio of the total reaction system heat exchanged surface area to the total reaction mixture volume≤[0.64*(reaction product discharge rate from the reaction system)]+0.60; alternatively, satisfying an upper boundary equation of the ratio of the total reaction system heat exchanged surface area to the total reaction mixture volume≤[0.64*(reaction product discharge rate from the reaction system)]+0.44; alternatively, satisfying an upper boundary equation of the ratio of the total reaction system heat exchanged surface area to the total reaction mixture volume≤[0.64*(reaction product discharge rate from the reaction system)]+0.28; alternatively, satisfying an upper boundary equation of the ratio of the total reaction system heat exchanged surface area to the total reaction mixture volume≤[0.64*(reaction product discharge rate from the reaction system)]+0.12; or alternatively, satisfying an upper boundary equation of the ratio of the total reaction system heat exchanged surface area to the total reaction mixture volume≤[0.64*(reaction product discharge rate from the reaction system)]−0.04. In the lower and upper boundary equations, the ratio of the total reaction system heat exchanged surface area to the total reaction mixture volume has units of in$^{-1}$ and the reaction product discharge rate from the reaction system is in units of lb/hr/gal. In further embodiments, the ratio of the total reaction system heat exchanged surface area to the total reaction mixture volume and the reaction product discharge rate from the reaction system can be further selected to have values between any lower boundary equation described herein and any upper boundary equation described herein.

Figure 8:
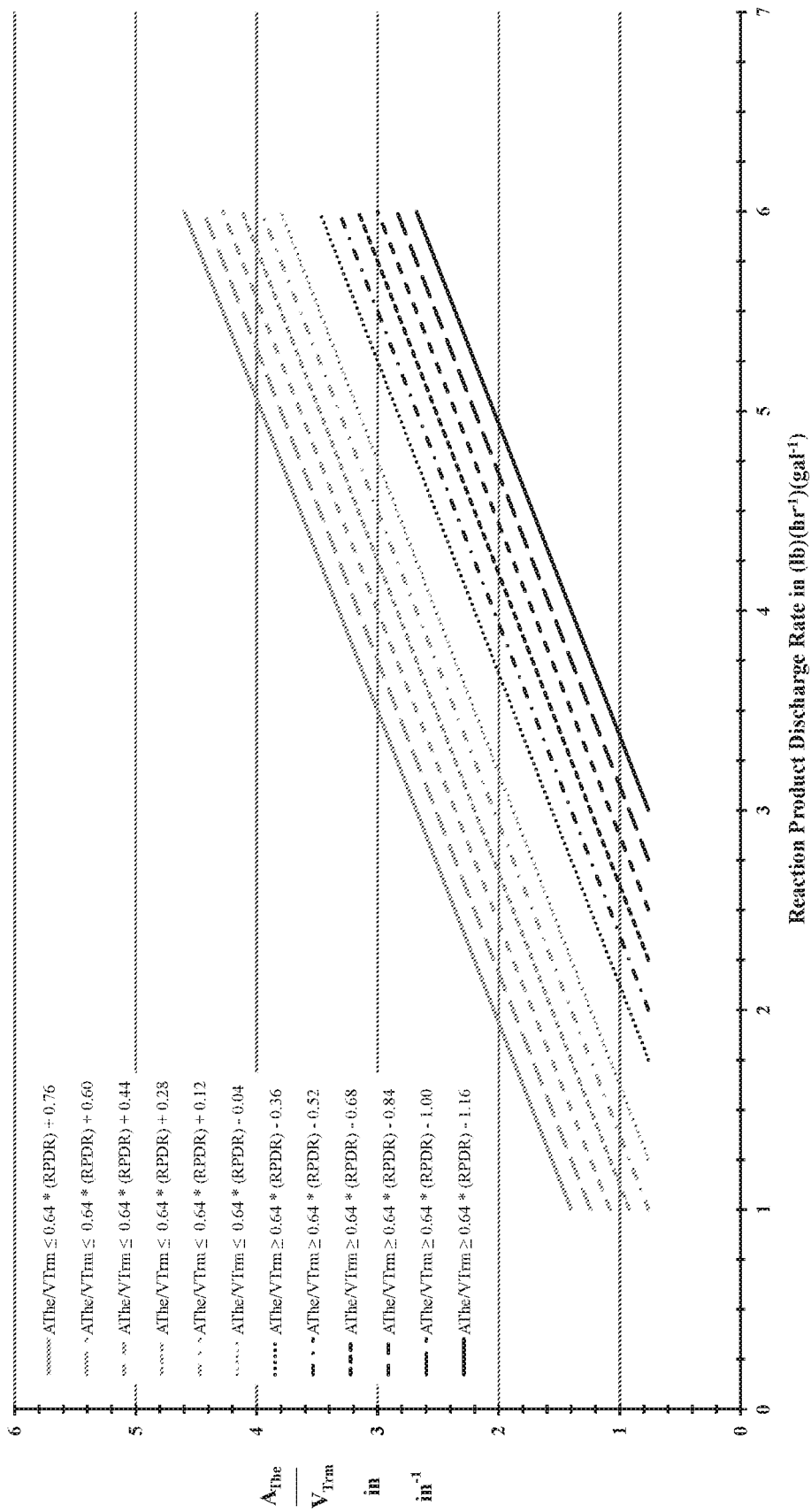
FIG. 8 illustrates a graph depicting operating parameters of a reaction process according to an embodiment.

For clarity, the ratio of the total reaction system heat exchanged surface area to the total reaction mixture volume and the reaction product discharge rate from the reaction system having minimum and/or maximum values as described herein is graphically illustrated in FIG. 8 in terms of a reaction product discharge rate from the reaction system. As shown in FIG. 8, the operation of the reaction process can take place within the selected operating parameters including the total reaction system heat exchanged surface area, the total reaction mixture volume, and the reaction product discharge rate from the reaction system, where the operation of the reaction system occurs within the upper and lower bounds described by the upper boundary equations and the lower boundary equations, respectively. It should be further noted that while the upper and lower boundary equations depicted in FIG. 8 are described in terms of reaction product discharge rate from the reaction system, it should be understood that within the upper and lower boundary equations depicted in FIG. 8 reaction product can be substituted with oligomer product, trimerization product, tetramerization product, or trimerization and tetramerization product according to the type of reaction process that is practiced in the reaction system.

Generally, the reaction systems described herein (comprising the reactors and/or the loops described herein) can be utilized to perform any reaction comprising contacting one or more reactants to form a reaction product. In an embodiment, the reaction systems described herein can be utilized in an olefin oligomerization process comprising contacting an olefin and a catalyst (or a catalyst system) to form an oligomerization product. In some embodiments, the reaction systems described herein and the reactors described herein can be utilized in an olefin trimerization process comprising contacting an olefin and a catalyst (or a catalyst system) to form a trimerization product. In other embodiments, the reaction systems described herein and the reactors described herein can be utilized in an olefin tetramerization process comprising contacting an olefin and a catalyst (or a catalyst system) to form a tetramerization product. In yet other embodiments, the reaction systems described herein and the reactors described herein can be utilized in an olefin trimerization and tetramerization process comprising contacting an olefin and a catalyst (or a catalyst system) to form a trimerization and tetramerization product.

In a further embodiment, the oligomerization, trimerization, tetramerization, or trimerization and tetramerization processes can be performed in the presence of a solvent. In an embodiment, the oligomerization, trimerization, tetramerization, or trimerization and tetramerization processes can comprise contacting hydrogen with the olefin and the catalyst (or catalyst system). In an embodiment the process can further comprise recovering the oligomer, trimer, tetramer, or trimer and tetramer. Generally, the olefin, the catalyst (the catalyst system or components of the catalyst system), reaction system solvent (if utilized), hydrogen (if utilized), and any other materials can be a fed to the reaction system and can be supplied to the reaction system via the one or more feed lines as described herein.

In the context of using the reaction system described herein for an olefin oligomerization process, an olefin trimerization process, an olefin tetramerization process, or an olefin trimerization and tetramerization process, the olefin (or the feed to the reaction system, or present in the reaction mixture) can comprise one or more olefins (e.g., olefin(s), alpha olefin(s), linear alpha olefin(s), or normal alpha olefin (s)). When the process is an olefin oligomerization process, an olefin trimerization process, an olefin tetramerization process, or an olefin trimerization and tetramerization process 1) the reaction occurring in the reaction system is an olefin oligomerization, an olefin trimerization, an olefin tetramerization, or an olefin trimerization and tetramerization (respectively), and 2) the reaction mixture is an olefin oligomerization mixture, an olefin trimerization mixture, an olefin tetramerization mixture, or an olefin trimerization and tetramerization mixture (respectively).

In some embodiments, the olefin can comprise a $C_2$ to $C_{30}$ olefin, a $C_2$ to $C_{16}$ olefin, or a $C_2$ to $C_{10}$ olefin. In some embodiments, the olefin (regardless of carbon number) can comprise alpha olefin(s), linear alpha olefin(s), or normal alpha olefin(s). In an embodiment, the olefin can comprise ethylene. When the olefin comprises, consists essentially of, or consists of, ethylene, 1) the process can be an ethylene oligomerization process, an ethylene trimerization process, an ethylene tetramerization process, or an ethylene trimerization and tetramerization process, 2) the reaction occurring in the reaction process is an ethylene oligomerization, an ethylene trimerization, an ethylene tetramerization, or an ethylene trimerization and tetramerization (respectively), and 3) the reaction mixture is an ethylene oligomerization mixture, an ethylene trimerization mixture, an ethylene tetramerization mixture, or an ethylene trimerization and tetramerization mixture (respectively). When the process is an ethylene oligomerization process, the oligomerization product can comprise olefins, including normal alpha olefins. When the process is an ethylene trimerization process, the trimerization product can comprise hexenes, such as 1-hexene. When the process is an ethylene tetramerization process, the tetramerization product can comprise octenes, such as 1-octene. When the process is an ethylene trimerization and tetramerization process, the trimerization and tetramerization product can comprise hexenes and octenes, such as 1-hexene and 1-octene. In some ethylene oligomerization embodiments, the oligomerization mixture, ethylene trimerization mixture, ethylene tetramerization mixture, or ethylene trimerization and tetramerization mixture can comprise at least 0.1 wt. %, 0.5 wt. %, 1 wt. %, 2.5 wt. %, 5 wt. %, 7.5 wt. %, or 10 wt. % ethylene based upon the oligomerization mixture. In other ethylene oligomerization embodiments, the oligomerization mixture, ethylene trimerization mixture, ethylene tetramerization mixture, or ethylene trimerization and tetramerization mixture can comprise a maximum of 50 wt. %, 40 wt. %, 30 wt. %, 25 wt. %, 20 wt. %, 17.5 wt. %, or 15 wt. % ethylene based upon the oligomerization mixture. In an ethylene oligomerization embodiment, the ethylene in the oligomerization mixture, ethylene trimerization mixture, ethylene tetramerization mixture, or ethylene trimerization and tetramerization mixture can range from any minimum weight percent described herein to any maximum weight percent described herein. Exemplary weight percentages for the ethylene that can be present the oligomerization mixture, ethylene trimerization mixture, ethylene tetramerization mixture, or ethylene trimerization and tetramerization mixture can comprise from 0.1 wt. % to 50 wt. %, 5 wt. % to 40 wt. %, 5 wt. % to 30 wt. %, 10 wt. % to 30 wt. %, 10 wt. % to 25 wt. %, 10 wt. % to 20 wt. %, 10 wt. % to 15 wt. %. Other ranges for the amount of ethylene that can be present in the oligomerization mixture, ethylene trimerization mixture, ethylene tetramerization mixture, or ethylene trimerization and tetramerization mixture are readily apparent from this disclosure.

In one or more embodiments, the use of the reaction system can be specifically described in relation to an ethylene oligomerization process, an ethylene trimerization process, ethylene tetramerization process, or an ethylene trimerization and tetramerization process comprising contacting a) ethylene and b) a catalyst system comprising i) a transition metal compound, ii) a heteroatomic ligand and iii) a metal alkyl compound to form an ethylene oligomerization product, an ethylene trimerization product, an ethylene tetramerization product, or an ethylene trimerization and tetramerization product (respectively). In other embodiments, the use of the reaction system can be specifically described in relation to an ethylene oligomerization process, an ethylene trimerization process, ethylene tetramerization process, or an ethylene trimerization and tetramerization process, comprising contacting a) ethylene and b) a catalyst system comprising i) a transition metal compound complexed to a heteroatomic ligand and ii) a metal alkyl compound to form an ethylene oligomerization product, an ethylene trimerization product, an ethylene tetramerization product, or an ethylene trimerization and tetramerization product (respectively). In some embodiments, an optional halogen containing compound can be a component of the catalyst system or alternatively, a halogen containing compound can be a further component contacted in the reaction system to form an ethylene oligomerization product, an ethylene trimerization product, an ethylene tetramerization product, or an ethylene trimerization and tetramerization product. In other embodiments, a solvent can be a further component contacted in the reaction system to form an ethylene oligomerization product, an ethylene trimerization product, an ethylene tetramerization product, or an ethylene trimerization and tetramerization product. In other embodiments, hydrogen can be a further component contacted in the reaction system to form an ethylene oligomerization product, an ethylene trimerization product, an ethylene tetramerization product, or an ethylene trimerization and tetramerization product. While the use of the reaction system can be described for use in the ethylene oligomerization process, ethylene trimerization process, ethylene tetramerization process, or ethylene trimerization and tetramerization process, one having ordinary skill in the art can realize that the reaction system can be utilized in other processes which can utilize a similar reaction system.

In one or more embodiments, the use of the reaction system can be specifically described in relation to an ethylene oligomerization process, an ethylene trimerization process, ethylene tetramerization process, or an ethylene trimerization and tetramerization process comprising contacting a) ethylene and b) a catalyst system comprising i) a chromium compound, ii) a heteroatomic ligand and iii) a metal alkyl compound to form an ethylene oligomerization product, an ethylene trimerization product, an ethylene tetramerization product, or an ethylene trimerization and tetramerization product (respectively). In other embodiments, the use of the reaction system can be specifically described in relation to an ethylene oligomerization process, an ethylene trimerization process, ethylene tetramerization process, or an ethylene trimerization and tetramerization process, comprising contacting a) ethylene and b) a catalyst system comprising i) a chromium compound complexed to a heteroatomic ligand and ii) a metal alkyl compound to form an ethylene oligomerization product, an ethylene trimerization product, an ethylene tetramerization product, or an ethylene trimerization and tetramerization product (respectively). In some embodiments, an optional halogen containing compound can be a component of the catalyst system or alternatively, a halogen containing compound can be a further component contacted to form an ethylene oligomerization product, an ethylene trimerization product, an ethylene tetramerization product, or an ethylene trimerization and tetramerization product. In other embodiments, a solvent can be a further component contacted in the reaction system to form an ethylene oligomerization product, an ethylene trimerization product, an ethylene tetramerization product, or an ethylene trimerization and tetramerization product. In other embodiments, hydrogen can be a further component contacted in the reaction system to form an ethylene oligomerization product, an ethylene trimerization product, an ethylene tetramerization product, or an ethylene trimerization and tetramerization product. While the use of the reaction system can be described for use in the ethylene oligomerization process, ethylene trimerization process, ethylene tetramerization process, or ethylene trimerization and tetramerization process, one having ordinary skill in the art can realize that reaction system can be utilized in other processes which can utilize a similar reaction system.

In one or more embodiments, the use of the reaction system can be specifically described in relation to an ethylene oligomerization process comprising contacting a) ethylene and b) a catalyst system comprising i) a transition metal compound (e.g., an iron or cobalt compound, among other transition metal compounds disclosed herein), ii) a heteroatomic ligand and iii) a metal alkyl compound to form an ethylene oligomerization product. In other embodiments, the use of the reaction system can be specifically described in relation to an ethylene oligomerization process comprising contacting a) ethylene and b) a catalyst system comprising i) a transition metal compound (e.g., an iron or cobalt compound, among other transition metal compounds disclosed herein) complexed to a heteroatomic ligand and ii) a metal alkyl compound to form an ethylene oligomerization product. In some embodiments, an optional halogen containing compound can be a component of the catalyst system or alternatively, a halogen containing compound can be a further component contacted to form an ethylene oligomerization product. In other embodiments, a solvent can be a further component contacted in the reaction system to form an ethylene oligomerization product. In other embodiments, hydrogen can be a further component contacted in the reaction system to form an ethylene oligomerization product. In particular embodiments, the heteroatomic ligand which can be utilized in the catalyst system comprising i) a transition metal compound (e.g., an iron or cobalt compound, among other transition metal compounds disclosed herein), ii) a heteroatomic ligand and iii) a metal alkyl compound can be a pyridine 2,6-bis-imine compound as described herein. In other particular embodiments, the heteroatomic ligand which can be utilized in the catalyst system comprising i) a transition metal compound (e.g., an iron or cobalt compound, among other transition metal compounds disclosed herein) complexed to a heteroatomic ligand and ii) a metal alkyl compound to form an ethylene oligomerization product can be an α-diimine compound as described herein or a pyridine 2,6-bis-imine compound as described herein; alternatively, an α-diimine compound as described herein; or alternatively, a pyridine 2,6-bis-imine compound as described herein. While the use of the reaction system can be described for use in this ethylene oligomerization process, one having ordinary skill in the art can realize that reaction system can be utilized in other processes which can utilize a similar reaction system.

In the context of using the reaction system described herein for an olefin oligomerization process, an olefin trimerization process, an olefin tetramerization process, or an olefin trimerization and tetramerization process, the process can utilize a solvent (interchangeable with reaction system solvent). As used herein, "solvent" and "reaction system solvent" includes materials which can act as a solvent or a diluent in the process described herein. As such, solvent, diluent, reaction system solvent and reaction system diluent are used interchangeably herein. In an embodiment, the solvent can be a hydrocarbon, a halogenated hydrocarbon, or a combination thereof, for example. Hydrocarbons and halogenated hydrocarbons which can be used as a solvent can include, for example, aliphatic hydrocarbons, aromatic hydrocarbons, petroleum distillates, halogenated aliphatic hydrocarbons, halogenated aromatic hydrocarbons, or combinations thereof. Aliphatic hydrocarbons which can be useful as a solvent include $C_3$ to $C_{20}$ aliphatic hydrocarbons, or $C_4$ to $C_{15}$ aliphatic hydrocarbons, or $C_5$ to $C_{10}$ aliphatic hydrocarbons, for example. The aliphatic hydrocarbons which can be used as a solvent can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), or combinations thereof. Non-limiting examples of suitable cyclic aliphatic hydrocarbon which can be used as a solvent include cyclohexane, and methyl cyclohexane, for example. Aromatic hydrocarbons which can be useful as a solvent include aromatic hydrocarbons, or $C_6$ to $C_{10}$ aromatic hydrocarbons. Non-limiting examples of suitable aromatic hydrocarbons that can be utilized singly or in any combination as a solvent include benzene, toluene, xylene (including ortho-xylene, meta-xylene, para-xylene, or mixtures thereof), ethylbenzene, or combinations thereof. Halogenated aliphatic hydrocarbons which can be useful as a solvent include $C_1$ to $C_{15}$ halogenated aliphatic hydrocarbons, or $C_1$ to $C_{10}$ halogenated aliphatic hydrocarbons, or $C_1$ to $C_5$ halogenated aliphatic hydrocarbons, for example. The halogenated aliphatic hydrocarbons which can be used as a solvent can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof. Halogenated aromatic hydrocarbons which can be useful as a solvent include $C_6$ to $C_{20}$ halogenated aromatic hydrocarbons, or $C_6$ to $C_{10}$ halogenated aromatic hydrocarbons, for example. Non-limiting examples of suitable halogenated aromatic hydrocarbons which can be used as a solvent include chlorobenzene, dichlorobenzene, or combinations thereof, for example.

The choice of reaction system solvent can be made on the basis of convenience in processing. For example, isobutane can be chosen to be compatible with solvents and diluents used in processes using the oligomerization product, trimerization product, tetramerization product, or trimerization and tetramerization product (e.g., using the product for the formation of polymer in a subsequent processing step). In some embodiments, the reaction system solvent can be chosen to be easily separable from the oligomerization product, trimerization product, tetramerization product, or trimerization and tetramerization product. In some embodiments, a component of the oligomerization product, trimerization product, tetramerization product, trimerization and tetramerization product, or reaction process feedstock can be utilized as the reaction system solvent. For example, since 1-hexene can be the oligomerization product of an ethylene trimerization process, 1-hexene can be chosen as the reaction system solvent to decrease the need for separation. In additional or alternative embodiments, a reaction process can be carried out in a solvent which is a product of the olefin oligomerization process. Therefore, the choice of reaction system solvent can be based on the selection of the initial olefin reactant and/or the oligomerization product. For example, if the oligomerization catalyst system is used to trimerize ethylene to 1-hexene, the solvent for the oligomerization reaction can be 1-hexene. If ethylene and hexene are trimerized, the oligomerization reaction solvent can be 1-hexene, and/or a trimerization product. If a reaction product is utilized as the reaction solvent, the amount of reaction product that is the reaction solvent is not included in the calculation for the reaction product produced in the reaction system or the calculation of the reaction product discharge rate.

In the context of using the reaction systems described herein for an ethylene oligomerization, ethylene trimerization process, an ethylene tetramerization process, or an ethylene trimerization and tetramerization process, the reaction mixture and/or the reaction system feed(s) (or alternatively, the ethylene oligomerization mixture and/or the ethylene oligomerization reaction system feed(s), the ethylene trimerization mixture and/or the ethylene trimerization reaction system feeds(s), the ethylene tetramerization mixture and/or the ethylene tetramerization reaction system feeds(s), or the ethylene trimerization and tetramerization mixture and/or the ethylene trimerization and tetramerization reaction system feeds(s)) can further comprise a catalyst system (ethylene oligomerization catalyst system, ethylene trimerization catalyst system, ethylene tetramerization catalyst system, or ethylene trimerization and tetramerization catalyst system), or further comprise one or more components of the catalyst system. The oligomerization catalyst system, the ethylene trimerization catalyst system, ethylene tetramerization catalyst system, or ethylene trimerization and tetramerization catalyst system can comprise, minimally, a transition metal compound, a heteroatomic ligand, and a metal alkyl compound. In an embodiment, the oligomerization catalyst system, the ethylene trimerization catalyst system, ethylene tetramerization catalyst system, or ethylene trimerization and tetramerization catalyst system can comprise, minimally, transition metal compound complexed to a heteroatomic ligand and a metal alkyl compound. In an embodiment, the oligomerization catalyst system, the ethylene trimerization catalyst system, ethylene tetramerization catalyst system, or ethylene trimerization and tetramerization catalyst system can comprise, minimally, a chromium compound, a heteroatomic ligand, and a metal alkyl compound. In an embodiment, the oligomerization catalyst system, the ethylene trimerization catalyst system, ethylene tetramerization catalyst system, or ethylene trimerization and tetramerization catalyst system can comprise, minimally, chromium compound complexed to a heteroatomic ligand and a metal alkyl compound. In another aspect, the oligomerization catalyst system, ethylene trimerization catalyst system, ethylene tetramerization catalyst system, or ethylene trimerization and tetramerization catalyst system can further comprise a halogen containing compound. The transition metal compound, transition metal compound complexed to a heteroatomic ligand, chromium compound, chromium compound complexed to a heteroatomic ligand, heteroatomic ligand, metal alkyl, and optional halogen containing compound are independent elements of the catalyst system. These elements of the catalyst system are independently described herein and the catalyst system can be further described utilizing any combination of the transition metal (or chromium compound) described herein, the heteroatomic ligand described herein, transition metal compound complexed to a heteroatomic ligand (or chromium compound complexed to a heteroatomic ligand) described herein, metal alkyl compound described herein, and optional halogen containing compound described herein.

Generally, the transition metal compound for the catalyst systems described herein can be a group 5, 6, 7, 8, 9, 10, or 11 transition metal compound. In some embodiments, the transition metal compound for the catalyst systems described herein can be a chromium compound, a nickel compound, a cobalt compound, an iron compound, a cobalt compound, a molybdenum compound, or a copper compound. In one or more specific embodiments, the transition metal compound for the catalyst systems described herein can be a chromium compound. In other specific embodiments, the transition metal compound for the catalyst systems described herein can be an iron compound or a cobalt compound; alternatively, an iron compound; or alternatively, a cobalt compound. In other specific embodiments, the transition metal compound can be a nickel compound.

In an aspect and in any embodiment, the transition metal compound for the catalyst systems described can comprise, can consist essentially of, or can be, a transition metal halide, carboxylate, beta-dionate, alkoxide, phenoxide, nitrate, sulfate, phosphate, or chlorate; alternatively a transition metal halide or beta-dionate; alternatively, a transition metal halide; or alternatively, a transition metal beta-dionate. In an embodiment, each carboxylate group of the transition metal compound independently can be a $C_2$ to $C_{24}$ carboxylate group, or a $C_4$ to $C_{19}$ carboxylate group, or a $C_5$ to $C_{12}$ carboxylate group. In some embodiments, each alkoxy group of the transition metal compound independently can be a $C_1$ to $C_{24}$ alkoxy group, or a $C_4$ to $C_{19}$ alkoxy group, or a $C_5$ to $C_{12}$ alkoxy group. In other embodiments, each aryloxy group of the transition metal compound independently can be a $C_6$ to $C_{24}$ aryloxy group, or a $C_6$ to $C_{19}$ aryloxy group, or a $C_6$ to $C_{12}$ aryloxy group. In yet other embodiments, each beta-dionate group of the transition metal compound independently can be a $C_5$ to $C_{24}$ beta-dionate group, or a $C_5$ to $C_{19}$ beta-dionate group, or a $C_5$ to $C_{12}$ beta-dionate group.

The chromium compound (of the catalyst systems described herein) can have a chromium oxidation state of from 0 to 6, or from 2 to 3 (i.e., a chromium(II) compound or a chromium(III) compound). The iron compound (of the catalyst systems described herein) can have an iron oxidation state of 2 or 3 (i.e., an iron(II) compound or an iron(III) compound); or alternatively, 3. The cobalt compound (of the catalyst systems described herein) can have a cobalt oxidation state of 2 or 3 (i.e., a cobalt(II) compound or a cobalt(III) compound); alternatively, 2; or alternatively, 3. The nickel compound (of the catalyst systems described herein) can have a nickel oxidation state of 0, 1, or 2 (i.e., a nickel(0) compound, a nickel(I) compound, or a nickel(II) compound); alternatively, 0; alternatively, 1; or alternatively, 2.

For example, chromium(II) compounds which can be used as the transition metal compound for the catalyst system described herein can comprise chromium(II) nitrate, chromium(II) sulfate, chromium(II) fluoride, chromium(II) chloride, chromium(II) bromide, or chromium(II) iodide. Also by way of example, the chromium(III) compounds which can be used as the transition metal compound for the catalyst systems described herein can comprise chromium (III) nitrate, chromium(III) sulfate, chromium(III) fluoride, chromium(III) chloride, chromium(III) bromide, or chromium(III) iodide. In yet an additional aspect of this disclosure and in any embodiment, the transition metal compound for the catalyst system can comprise a chromium(II) alkoxide, a chromium(II) carboxylate, a chromium(II) beta-dionate, a chromium(III) alkoxide, a chromium(III) carboxylate, or a chromium(III) beta-dionate. In an embodiment, each carboxylate group of the chromium compound independently can be a $C_2$ to $C_{24}$ carboxylate group, or a $C_4$ to $C_{19}$ carboxylate group, or a $C_5$ to $C_{12}$ carboxylate group. In some embodiments, each alkoxy group of the chromium compound independently can be a $C_1$ to $C_{24}$ alkoxy group, or a $C_4$ to $C_{19}$ alkoxy group, or a $C_5$ to $C_{12}$ alkoxy group. In other embodiments, each aryloxy group of the chromium compound independently can be a $C_6$ to $C_{24}$ aryloxy group, or a $C_6$ to $C_{19}$ aryloxy group, or a $C_6$ to $C_{12}$ aryloxy group. In yet other embodiments, each beta-dionate group of the chromium compound independently can be a $C_5$ to $C_{24}$ beta-dionate group, or a $C_5$ to $C_{19}$ beta-dionate group, or a $C_5$ to $C_{12}$ beta-dionate group. Chromium carboxylates are particularly useful transition metal compounds for some catalyst systems described herein. Thus, in one aspect, the catalyst systems described herein can use a chromium carboxylate composition in which the carboxylate is a $C_2$ to $C_{24}$ monocarboxylate, or a $C_4$ to $C_{19}$ monocarboxylate, or a $C_5$ to $C_{12}$ monocarboxylate.

In an embodiment, each carboxylate group of the chromium, iron, or cobalt carboxylate independently can be an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; alternatively, a pentanoate, a hexanoate, a heptanoate, a octanoate, a nonanoate, a decanoate, a undecanoate, or a dodecanoate. In some embodiments, each carboxylate group of the chromium carboxylate independently can be acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate).

In an aspect and in any embodiment, the transition metal compound for the catalyst system systems described herein can comprise, can consist essentially of, or can be, a chromium(II) carboxylate or a chromium(III) carboxylate. Exemplary chromium(II) carboxylates can comprise, can consist essentially of, or can be, chromium(II) acetate, chromium(II) propionate, chromium(II) butyrate, chromium (II) isobutyrate, chromium(II) neopentanoate, chromium(II) oxalate, chromium(II) octanoate, chromium(II) 2-ethylhexanoate, chromium(II) laurate, or chromium(II) stearate; alternatively, chromium(II) acetate, chromium(II) propionate, chromium(II) butyrate, chromium(II) isobutyrate, chromium(II) neopentanoate, chromium(II) octanoate, chromium(II) 2-ethylhexanoate, chromium(II) laurate, or chromium(II) stearate. In an aspect and in any embodiment, the transition metal compound utilized in the catalyst system can comprise, can consist essentially of, or can be, chromium(III) acetate, chromium(III) propionate, chromium(III) butyrate, chromium(III) isobutyrate, chromium(III) neopentanoate, chromium(III) oxalate, chromium(III) octanoate, chromium(III) 2-ethylhexanoate, chromium(III) 2,2,6,6,-tetramethylheptanedionate, chromium(III) naphthenate, chromium(III) laurate, or chromium(III) stearate; or alternatively, chromium(III) 2-ethylhexanoate.

In an aspect and in any embodiment, the iron compound for the catalyst systems described herein comprising i) an iron compound, ii) a heteroatomic ligand and iii) a metal alkyl compound or comprising i) an iron compound complexed to a heteroatomic ligand and ii) a metal alkyl compound can comprise, can consist essentially of, or can be, iron(II) chloride, iron(III) chloride, iron(II) fluoride, iron (III) fluoride, iron (II) bromide, iron(III) bromide, iron(II) iodide, iron(III) iodide, iron(II) acetate, iron (III) acetate, iron(II) acetylacetonate, or iron(III) acetylacetonate; alternatively, iron(II) chloride or iron(III) chloride; alternatively, iron(II) chloride; or alternatively, iron(III) chloride. In an aspect and in any embodiment, the cobalt compound for the catalyst systems described herein comprising i) a cobalt compound, ii) a heteroatomic ligand and iii) a metal alkyl compound or comprising i) a cobalt compound complexed to a heteroatomic ligand and ii) a metal alkyl compound can comprise, can consist essentially of, or can be, cobalt(II) chloride, cobalt(III) chloride, cobalt(II) fluoride, cobalt(III) fluoride, cobalt (II) bromide, cobalt(III) bromide, cobalt(II) iodide, cobalt(III) iodide, cobalt(II) acetate, cobalt (III) acetate, cobalt(II) acetylacetonate, cobalt(II) benzoylacetonate, or cobalt(III) acetylacetonate; alternatively, cobalt(II) chloride; or alternatively, cobalt(III) chloride.

In an embodiment, the heteroatomic ligand (whether it is a separate component of the catalyst system or is a ligand complexed to the transition metal or chromium compound of the catalyst system) can comprise, can consist essentially of, or can be, an amine, amide, or imide compound. In one or more embodiments, the heteroatomic ligand (whether it is a separate component of the catalyst system or is a ligand complexed to the transition metal or chromium compound of the catalyst system) can comprise, can consist essentially of, or can be, a pyrrole compound, a diphosphinoaminyl compound, a $N^2$-phosphinylamidine compound, a $N^2$-phosphinylformadine compound, a phosphinyl guanidine compound or any combination thereof. In some embodiments, the heteroatomic ligand (whether it is a separate component of the catalyst system or is a ligand complexed to the transition metal or chromium compound of the catalyst system) can comprise, can consist essentially of, or can be, a pyrrole compound; alternatively, a diphosphinoaminyl compound; alternatively, a $N^2$-phosphinylamidine compound; alternatively, a $N^2$-phosphinylformadine compound; or alternatively, a phosphinyl guanidine compound.

In an embodiment, the amine compound can be a $C_2$ to $C_{30}$ amine; alternatively, a $C_2$ to $C_{20}$ amine; alternatively, $C_2$ to $C_{15}$ amine; or alternatively, a $C_2$ to $C_{10}$ amine. In an embodiment, the amide compound can be a $C_3$ to $C_{30}$ amide; alternatively, a $C_3$ to $C_{20}$ amide; alternatively, $C_3$ to $C_{15}$ amide; or alternatively, a $C_3$ to $C_{10}$ amide. In an embodiment, the imide compound can be a $C_4$ to $C_{30}$ imide; alternatively, a $C_4$ to $C_{20}$ imide; alternatively, $C_4$ to $C_{15}$ imide; or alternatively, a $C_4$ to $C_{10}$ imide.

In an aspect, the pyrrole compound (also called the "pyrrole") which can be utilized in the catalyst systems described herein can comprise any pyrrole compound that can form a transition metal pyrrolide complex (e.g., chromium pyrrolide complex). As used in this disclosure, the term "pyrrole compound" refers to pyrrole ($C_5H_5N$), derivatives of pyrrole (e.g., indole), substituted pyrroles, as well as metal pyrrolide compounds. A pyrrole compound is defined as a compound comprising a 5-membered, nitrogen-containing heterocycle, such as, for example, pyrrole, derivatives of pyrrole, and mixtures thereof. Broadly, the pyrrole compound can be pyrrole or any heteroleptic or homoleptic metal complex or salt containing a pyrrolide radical or ligand. Generally, the pyrrole compound can be a $C_4$ to $C_{30}$ pyrrole; alternatively, a $C_4$ to $C_{20}$ pyrrole; alternatively, $C_4$ to $C_{15}$ pyrrole; or alternatively, a $C_4$ to $C_{10}$ pyrrole.

In an aspect, the pyrrole compound which can be utilized in the catalyst systems described herein can have Formula P1 or Formula I1. In an embodiment, the pyrrole compound which can be utilized in the catalyst systems described herein can have Formula P1; or alternatively Formula I1.

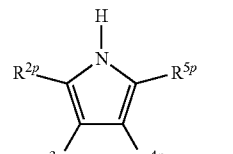

P1

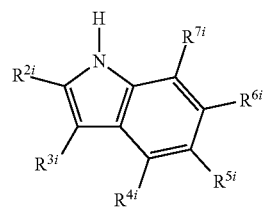

I1

In an aspect, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 independently can be a hydrogen, a $C_1$ to $C_{18}$ organyl group, or a $C_3$ to $C_{60}$ silyl group; alternatively, hydrogen, a $C_1$ to $C_{15}$ organyl group, or a $C_3$ to $C_{45}$ silyl group; alternatively, hydrogen, a $C_1$ to $C_{10}$ organyl group, or a $C_3$ to $C_{30}$ silyl group; alternatively, hydrogen, a $C_1$ to $C_5$ organyl group, or a $C_3$ to $C_{15}$ silyl group; alternatively, hydrogen or a $C_1$ to $C_{18}$ organyl group; alternatively, hydrogen or a $C_1$ to $C_{15}$ organyl group; alternatively, hydrogen or a $C_1$ to $C_{10}$ organyl group; or alternatively, hydrogen or a $C_1$ to $C_5$ organyl group. In an embodiment, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 independently can be a hydrogen, a $C_1$ to $C_{18}$ hydrocarbyl group, or a $C_3$ to $C_{60}$ silyl group; alternatively, hydrogen, a $C_1$ to $C_{15}$ hydrocarbyl group, or a $C_3$ to $C_{45}$ silyl group; alternatively, hydrogen, a $C_1$ to $C_{10}$ hydrocarbyl group, or a $C_3$ to $C_{35}$ silyl group; alternatively, hydrogen, a $C_1$ to $C_5$ hydrocarbyl group, or a $C_3$ to $C_{15}$ silyl group; alternatively, hydrogen or a $C_1$ to $C_{18}$ hydrocarbyl group; alternatively, hydrogen or a $C_1$ to $C_{15}$ hydrocarbyl group; alternatively, hydrogen or a $C_1$ to $C_{10}$ hydrocarbyl group; or alternatively, hydrogen or a $C_1$ to $C_5$ hydrocarbyl group.

In an embodiment, the pyrrole compound which can be utilized in the catalyst systems described herein can comprise, can consist essentially of, or can be, individually or in any combination, pyrrole, 2,5-dimethylpyrrole, 2-methyl-5-ethylpyrrole, 2-methyl-5-propylpyrrole, 2,5-diethylpyrrole, 3,4-dimethylpyrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,5-dibenzylpyrrole, 2,4-dimethyl-3-ethylpyrrole, 2,3,5-triethylpyrrole, 2,3,5-tri-n-butylpyrrrole, 2,3,5-tri-n-pentylpyrrrole, 2,3,5-tri-n-hexylpyrrrole, 2,3,5-tri-n-heptylpyrrrole, 2,3,5-tri-n-octylpyrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neo-pentylpyrrole, 2-ethyl-4-neopentylpyrrole, 3,4-diisopropylpyrrole, 3,4-di-sec-butylpyrrole, 3,4-diisobutylpyrrole, 3,4-di-t-butylpyrrole, 3,4-di-neo-pentylpyrrole, tetrahydroindole, dipyrrolylmethane, indole, 3,4-dichloropyrrole, 2,3,4,5-tetrachloropyrrole, pyrrole-2-carboxylic acid, 2-acetylpyrrole, pyrrole-2-carboxaldehyde, 3-acetyl-2,4-dimethylpyrrole, ethyl-2,4-dimethyl-5-(ethoxycarbonyl)-3-pyrrole-propionate, or ethyl-3,5-dimethyl-2-pyrrolecarboxylate. In some embodiments, pyrrole compounds that can be used in the catalyst system comprise, but are not limited to pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-propionate, ethyl-3,5-dimethyl-2-pyrrolecarboxylate, 3,4-dichloropyrrole, 2,3,4,5-tetrachloropyrrole, 2-acetylpyrrole, pyrazole, pyrrolidine, indole, and dipyrrolylmethane, and mixtures thereof. In other embodiments, the pyrrole compound which can be utilized in the catalyst systems described herein can comprise, can consist essentially of, or can be, individually or in any combination, pyrrole, 2,5-dimethylpyrrole, 2-methyl-5-ethylpyrrole, 2-methyl-5-propylpyrrole, or 2,5-diethylpyrrole; alternatively, pyrrole; alternatively, 2,5-dimethylpyrrole; alternatively, 2-methyl-5-ethylpyrrole; alternatively, 2-methyl-5-propylpyrrole; or alternatively, 2,5-diethylpyrrole.

In an embodiment, the pyrrole compound which can be utilized in the catalyst systems described herein can comprise a metal pyrrolide, such as an alkyl metal pyrrolide. In some embodiments, the pyrrole compound which can be utilized in the catalyst systems described herein can comprise, individually or in any combination, a dialkylaluminum pyrrolide of any pyrrole provided herein. Alkyl groups have been described herein (e.g., as alkyl group for the metal alkyl) and these alkyl groups can be utilized to further describe the alkyl metal pyrrolide and/or the dialkylaluminum pyrrolide which can be utilized as the pyrrole compound which can be utilized in the catalyst systems described herein. In other embodiments, the pyrrole compound which can be utilized in the catalyst systems described herein can comprise, individually or in any combination, diethylaluminum 2,5-dimethylpyrrolide, ethylaluminum di(2,5-dimethylpyrrolide), or aluminum tri(2,5-dimethylpyrrolide).

In an embodiment, the heteroatomic ligand (whether it is a separate component of the catalyst system or is a ligand complexed to the transition metal compound of the catalyst system) can be a diphosphino aminyl compound. A diphosphino aminyl compound is a compound having a moiety characterized by having a P—N—P (phosphorus-nitrogen-phosphorus) linkage. The moiety having the P—N—P linkage can hereafter be referred to a PNP moiety or as a diphosphino aminyl moiety. The heteroatomic ligand (whether it is a separate component of the catalyst system or is a ligand complexed to the transition metal compound of the catalyst system) comprising the diphosphino aminyl moiety can be referred to as a PNP ligand, a diphosphino aminyl ligand, or a diphosphino aminyl compound.

In an embodiment, the heteroatomic ligand (whether it is a separate component of the catalyst system or is a ligand complexed to the transition metal compound of the catalyst system) can comprise a diphosphino aminyl moiety having Structure PNP1:

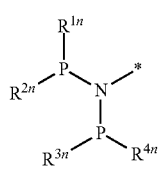

Structure PNP1 wherein $R^{1n}$, $R^{2n}$, $R^{3n}$, and $R^{4n}$ can be any group described herein and the undesignated aminyl nitrogen valence (*) represents the remainder of the heteroatomic ligand. In an embodiment, $R^{1n}$, $R^{2n}$, $R^{3n}$, and $R^{4n}$ can each be different. In some embodiments, $R^{1n}$, $R^{2n}$, $R^{3n}$, and $R^{4n}$ can each be the same. In other embodiments, $R^{1n}$ and $R^{2n}$ can be the same and $R^{3n}$ and $R^{4n}$ can be the same but different from $R^{1n}$ and $R^{2n}$. In yet other embodiments, $R^{1n}$ and $R^{3n}$ can be the same and $R^{2n}$ and $R^{4n}$ can be the same but different from $R^{1n}$ and $R^{3n}$.

In an embodiment, $R^{1n}$, $R^{2n}$, $R^{3n}$, and $R^{4n}$ independently can be an organyl group; alternatively, an organyl group comprising inert functional groups; or alternatively, a hydrocarbyl group. In an embodiment, the organyl group which can be utilized as $R^{1n}$, $R^{2n}$, $R^{3n}$, and $R^{4n}$ can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, the organyl group comprising inert functional groups which can be utilized as $R^{1n}$, $R^{2n}$, $R^{3n}$, and $R^{4n}$ can be a $C_1$ to $C_{30}$ organyl group comprising inert functional groups; alternatively, a $C_1$ to $C_{20}$ organyl group comprising inert functional groups; alternatively, a $C_1$ to $C_{15}$ organyl group comprising inert functional groups; alternatively, a $C_1$ to $C_{10}$ organyl group comprising inert functional groups; or alternatively, a $C_1$ to $C_5$ organyl group comprising inert functional groups. In an embodiment, the hydrocarbyl group which can be utilized as $R^{1n}$, $R^{2n}$, $R^{3n}$, and $R^{4n}$ can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In further embodiments, two or more of $R^{1n}$, $R^{2n}$, $R^{3n}$, and $R^{4n}$ can be joined to form a ring or a ring system.

In an embodiment, $R^{1n}$, $R^{2n}$, $R^{3n}$, and/or $R^{4n}$ of the diphosphino aminyl moiety independently can be a $C_1$ to $C_{30}$ alkyl group; alternatively, a $C_1$ to $C_{20}$ alkyl group; alternatively, a $C_1$ to $C_{15}$ alkyl group; alternatively, a $C_1$ to $C_{10}$ alkyl group; or alternatively, a $C_1$ to $C_5$ alkyl group. In still yet other embodiments, $R^{1n}$, $R^{2n}$, $R^{3n}$, and/or $R^{4n}$ of the diphosphino aminyl moiety independently can be a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group. In still yet other embodiments, $R^{1n}$, $R^{2n}$, $R^{3n}$, and/or $R^{4n}$ of the diphosphino aminyl moiety independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; alternatively, a phenyl group or a $C_6$ to $C_{10}$ substituted phenyl group; or alternatively, a phenyl group. In further embodiments, $R^{1n}$ and $R^{2n}$, and/or $R^{3n}$ and $R^{4n}$ of the diphosphino aminyl moiety complexes can be joined to form a ring (regardless of particular type of group—organyl, organyl consisting of inert functional groups, hydrocarbyl, or any species within) containing a phosphorus atom of the diphosphino aminyl moiety. General substituent groups are provided herein and these general substituent groups can be utilized to further describe the substituted phenyl groups which can be utilized as $R^{1n}$ and $R^{2n}$, and/or $R^{3n}$ and $R^{4n}$ for the diphosphino aminyl moiety.

In an embodiment, the heteroatomic ligand (whether it is a separate component of the catalyst system or is a ligand complexed to the transition metal compound of the catalyst system) can be compound having a $N^2$-phosphinyl formamidine group. Generally, a formamidine group is a group having the general structure

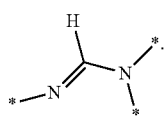

Within the formamidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl formamidine group has the general structure

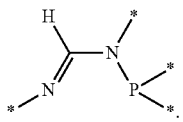

Within the $N^2$-phosphinyl formamidine group the $N^1$ and $N^2$ nitrogen atoms and $N^1$ and $N^2$ groups have the same meaning as described for the formamidine group. Consequently, an $N^2$-phosphinyl formamidine group has the phosphinyl group attached to the $N^2$ nitrogen atom.

In an embodiment, the heteroatomic ligand (whether it is a separate component of the catalyst system or is a ligand complexed to the transition metal compound of the catalyst system) can be an $N^2$-phosphinyl formamidine compound having Structure NPF1. In some embodiments, the transition metal compound complexed to an $N^2$-phosphinylformamidine compound can have Structure NPFMC1. In an embodiment, the transition metal compound complexed to an $N^2$-phosphinylformamidine compound can be a chromium compound complexed to an $N^2$-phosphinylformamidine compound having Structure NPFCr1.

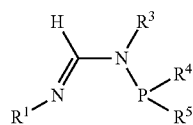

Structure NPF1

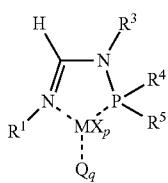

Structure NPFMC1

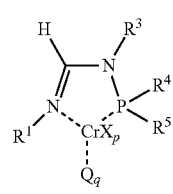

Structure NPFCr1

$R^1$, $R^3$, $R^4$, and $R^5$ within the $N^2$-phosphinyl formamidine compound having Structure NPF1, $N^2$-phosphinyl formamidine transition metal complex having Structure NPFMC1, and the $N^2$-phosphinyl formamidine chromium complex having Structure NPFCr1 are independently described herein and can be utilized without limitation to further describe the $N^2$-phosphinyl formamidine compound having Structure NPF1, the $N^2$-phosphinyl formamidine transition metal complex having Structure NPFMC1, and the $N^2$-phosphinyl formamidine chromium complex having Structure NPFCr1. $MX_p$ represents the transition metal compound of the $N^2$-phosphinyl formamidine transition metal complex having Structure NPFMC1. $CrX_p$ represents the chromium compound of the $N^2$-phosphinyl formamidine chromium complex having Structure NPFCr1. Q represents an optional neutral ligand within the $N^2$-phosphinyl formamidine transition metal complex having Structure NPFMC1 and the $N^2$-phosphinyl formamidine chromium complex having Structure NPFCr1, while q represents the number of optional neutral ligands present. $MX_p$, $CrX_p$, Q, and q are independently described herein and can be utilized without limitation to further describe the $N^2$-phosphinyl formamidine transition metal complex having Structure NPFMC1 and the $N^2$-phosphinyl formamidine chromium complex having Structure NPFCr1. Additionally, $MX_p$, $CrX_p$, Q, and q can be combined with the independently described $R^1$, $R^3$, $R^4$, and $R^5$ to further describe the $N^2$-phosphinyl formamidine transition metal complex having Structure NPFMC1 and the $N^2$-phosphinyl formamidine chromium complex having Structure NPFCr1.

In an embodiment, the heteroatomic ligand (whether it is a separate component of the catalyst system or is a ligand complexed to the transition metal compound of the catalyst system) can be compound having a $N^2$-phosphinyl amidine group. Generally, an amidine group is a group having the general structure

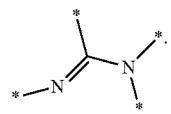

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl amidine group has the general structure

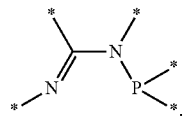

Within the $N^2$-phosphinyl amidine group the $N^1$ and $N^2$ nitrogen atoms and $N^1$ and $N^2$ groups have the same meaning as described for the amidine group. Consequently, an $N^2$-phosphinyl amidine group has the phosphinyl group attached to the $N^2$ nitrogen atom. Within the amidine group and $N^2$-phosphinyl amidine group the carbon atom between the two nitrogen atoms is the central carbon atom and any substituent attached to it is referred to as the central carbon group. For the purpose of this disclosure and claims, a compound having a pyridine group with a 2-amine group (or its analogues—e.g., a pyrimidine ring, an imidazole ring, a compound having 2-aminopyridine group, and the like) or having a 2-phosphinylamine group is not considered to constitute an amidine group or $N^2$-phosphinyl amidine group, respectively.

In an embodiment, the heteroatomic ligand (whether it is a separate component of the catalyst system or is a ligand complexed to the transition metal compound of the catalyst system) can be an $N^2$-phosphinyl amidine compound having Structure NPA1. In some embodiments, the transition metal compound complexed to an $N^2$-phosphinylamidine compound can have Structure NPAMC1. In an embodiment, the transition metal compound complexed to an $N^2$-phosphinylamidine compound can be a chromium compound complexed to an $N^2$-phosphinylamidine compound having Structure NPACr1.

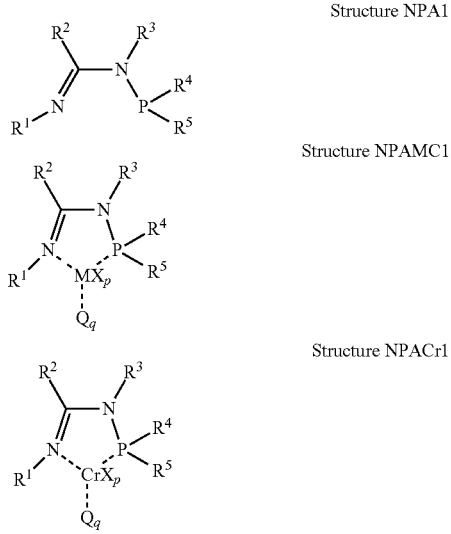

Structure NPA1

Structure NPAMC1

Structure NPACr1

$R^1$, $R^2$, $R^3$, $R^4$, and $R^5$ within the $N^2$-phosphinyl amidine compound having Structure NPA1, $N^2$-phosphinyl amidine transition metal complex having Structure NPAMC1, and the $N^2$-phosphinyl amidine chromium complex having Structure NPACr1 are independently described herein and can be utilized without limitation to further describe the $N^2$-phosphinyl amidine compound having Structure NPA1, the $N^2$-phosphinyl amidine transition metal complex having Structure NPAMC1, and the $N^2$-phosphinyl amidine chromium complex having Structure NPACr1. $MX_p$ represents the transition metal compound of the $N^2$-phosphinyl amidine transition metal complex having Structure NPAMC1. $CrX_p$ represents the chromium compound of the $N^2$-phosphinyl amidine chromium complex having Structure NPACr1. Q represents an optional neutral ligand of the $N^2$-phosphinyl amidine transition metal complex having Structure NPAMC1 and the $N^2$-phosphinyl amidine chromium complex having Structure NPACr1, while q represents the number of optional neutral ligands present. $MX_p$, $CrX_p$, Q, and q are independently described herein and can be utilized without limitation to further describe the $N^2$-phosphinyl amidine transition metal complex having Structure NPAMC1 and the $N^2$-phosphinyl amidine chromium complex having Structure NPACr1. Additionally, $MX_p$, $CrX_p$, Q, and q can be combined with the independently described $R^1$, $R^2$, $R^3$, $R^4$, and $R^5$ to further describe the $N^2$-phosphinyl amidine transition metal complex having Structure NPAMC1 and the $N^2$-phosphinyl amidine chromium complex having Structure NPACr1.

In an embodiment, the heteroatomic ligand (whether it is a separate component of the catalyst system or is a ligand complexed to the transition metal compound of the catalyst system) can be compound having a $N^2$-phosphinyl guanidine group. Generally, a guanidine group, is a group having the general structure

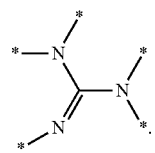

Within the guanidine core, the nitrogen participating in a double bond with the central carbon atom is referred to as the $N^1$ nitrogen and the two nitrogen atoms participating in a single bond with the central carbon atom are referred to as the $N^2$ nitrogen and the $N^3$ nitrogen. Similarly, the groups attached to the $N^1$, $N^2$ and $N^3$ nitrogen atoms are referred to as the $N^1$ group, $N^2$ group, and $N^3$ group respectively. An $N^2$-phosphinyl guanidine group, such as those found in a ligand of the $N^2$-phosphinyl guanidine complexes described herein, has the general structure

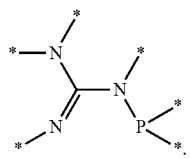

Within an $N^2$-phosphinyl guanidine group, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that a guanidine core or an $N^2$-phosphinyl guanidine group can be a portion of a larger group (or compound) which does not contain guanidine in it name. For example, while the compound 7-dimethylphosphinylimidazo[1,2-a] imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an $N^2$-phosphinyl guanidine group) since it contains the defined general structure of the guanidine core (or the $N^2$-phosphinyl guanidine group).

In an embodiment, the $N^2$-phosphinyl guanidine compound can have Structure Gu1, Gu2, Gu3, Gu4, or Gu5: alternatively, Structure Gu1; alternatively, Structure Gu2; alternatively, Structure Gu3; alternatively, Gu4; or alternatively, Gu5. In an embodiment, the $N^2$-phosphinyl guanidine transition metal complex can have Structure GuMC1, GuMC2, GuMC3, GuMC4, or GuMC5: alternatively, Structure GuMC1; alternatively, Structure GuMC2; alternatively, Structure GuMC3; alternatively, GuMC4; or alternatively, GuMC5. In an embodiment, the $N^2$-phosphinyl guanidine chromium complex can have Structure GuCr1, GuCr2, GuCr3, GuCr4, or GuCr5: alternatively, Structure GuCr1; alternatively, Structure GuCr2; alternatively, Structure GuCr3; alternatively, GuCr4; or alternatively, GuCr5.

Structure Gu1
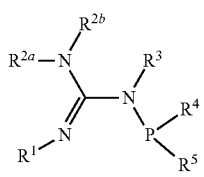

Structure Gu2
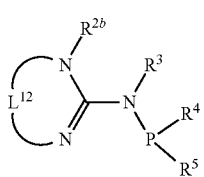

Structure Gu3
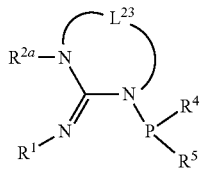

Structure Gu4
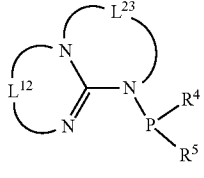

Structure Gu5
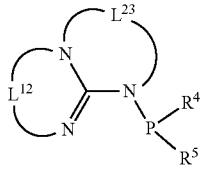

Structure GuMC1
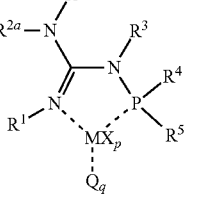

Structure GuMC2
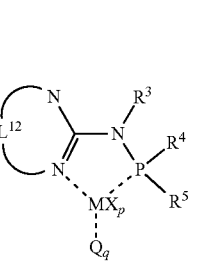

Structure GuMC3
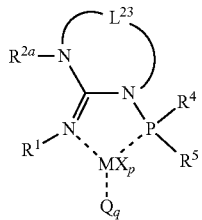

Structure GuMC4
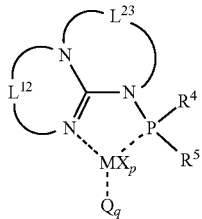

Structure GuMC5
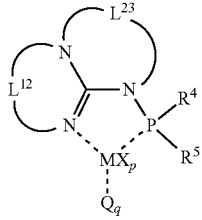

Structure GuCr1
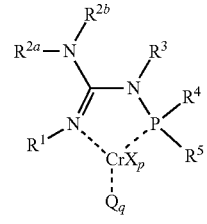

Structure GuCr2
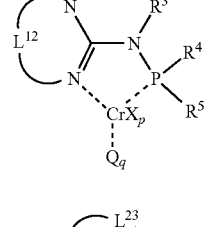

Structure GuCr3
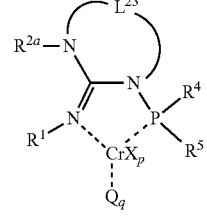

Structure GuCr4
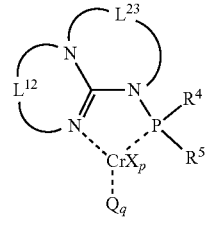

Structure GuCr5

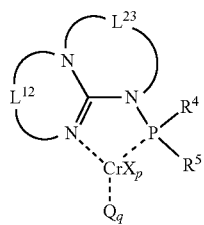

$R^1$, $R^{2a}$, $R^{2b}$, $R^3$, $R^4$, $R^5$, $L^{12}$, and $L^{22}$, within the appropriate i) $N^2$-phosphinyl guanidine compound Structures Gu1, Gu2, Gu3, Gu4, and/or Gu5, ii) $N^2$-phosphinyl guanidine transition metal complex Structures GuMC1, GuMC2, GuMC3, GuMC4, and/or GuMC5, and/or iii) $N^2$-phosphinyl guanidine chromium complex Structures GuCr1, GuCr2, GuCr3, GuCr4, and/or GuCr5 are independently described herein and can be utilized without limitation to further describe the appropriate i) $N^2$-phosphinyl guanidine compound Structures Gu1, Gu2, Gu3, Gu4, and/or Gu5, ii) $N^2$-phosphinyl guanidine transition metal complex Structures GuMC1, GuMC2, GuMC3, GuMC4, and/or GuMC5, and/or iii) $N^2$-phosphinyl guanidine chromium complex Structures GuCr1, GuCr2, GuCr3, GuCr4, and/or GuCr5. $MX_p$ within the $N^2$-phosphinyl guanidine transition metal complexes having $N^2$-phosphinyl guanidine transition metal complex Structures GuMC1, GuMC2, GuMC3, GuMC4, and GuMC5 represents the transition metal compound of the $N^2$-phosphinyl guanidine transition metal complexes. $CrX_p$ within the $N^2$-phosphinyl guanidine chromium complex Structures GuCr1, GuCr2, GuCr3, GuCr4, and/or GuCr5 represents the chromium compound of the $N^2$-phosphinyl guanidine chromium complexes. Q represents an optional neutral ligand of i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5, while q represents the number of optional neutral ligands present. $MX_p$, $CrX_p$, Q, and q are independently described herein and can be utilized without limitation to further describe i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5. Additionally, $MX_p$, $CrX_p$, Q, and q can be combined with the independently described $R^1$, $R^{2a}$, $R^{2b}$, $R^3$, $R^4$, and $R^5$ to further describe i) the $N^2$-phosphinyl guanidine transition metal complex Structures GuMC1, GuMC2, GuMC3, GuMC4, and GuMC5, and iii) the $N^2$-phosphinyl guanidine chromium complex Structures GuCr1, GuCr2, GuCr3, GuCr4, and/or GuCr5.

$R^1$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$ group can be an organyl group; alternatively, an organyl group consisting essentially of inert functional groups; or alternatively, a hydrocarbyl group. $R^2$ for the $N^2$-phosphinyl amidine compounds, the $N^2$-phosphinyl amidine transition metal complexes, and the $N^2$-phosphinyl amidine chromium complexes can be an organyl group; alternatively, an organyl group consisting essentially of inert functional groups; or alternatively, a hydrocarbyl group. $R^{2a}$ and/or $R^{2b}$ for the $N^2$-phosphinyl guanidine compounds, the $N^2$-phosphinyl guanidine transition metal complexes, and/or the $N^2$-phosphinyl guanidine chromium complexes, which have an $R^{2a}$ and/or $R^{2b}$ group independently can be hydrogen or an organyl group; alternatively, hydrogen or an organyl group consisting essentially of inert functional groups; alternatively, hydrogen or a hydrocarbyl group; alternatively, an organyl group; alternatively, an organyl group consisting essentially of inert functional groups; alternatively, a hydrocarbyl group; or alternatively hydrogen. $R^3$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^3$ group can be hydrogen or an organyl group; alternatively, hydrogen or an organyl group consisting essentially of inert functional groups; alternatively, hydrogen or a hydrocarbyl group; alternatively, an organyl group; alternatively, an organyl group consisting essentially of inert functional groups; alternatively, a hydrocarbyl group; or alternatively hydrogen. $R^4$ and/or $R^5$ of the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes independently can be an organyl group; alternatively, an organyl group consisting essentially of inert functional groups; or alternatively, a hydrocarbyl group.

In an embodiment, the organyl groups, which can be utilized as any one or more of the $R^1$, $R^2$, $R^{2a}$, $R^{2b}$, $R^3$, $R^4$ and/or $R^5$ for any $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, the organyl group consisting essentially of inert functional groups, which can be utilized as any one or more of the $R^1$, $R^2$, $R^{2a}$, $R^{2b}$, $R^3$, $R^4$ and/or $R^5$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, the hydrocarbyl groups, which can be utilized as any one or more of the $R^1$, $R^2$, $R^{2a}$, $R^{2b}$, $R^3$, $R^4$ and/or $R^5$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group.

In an embodiment, each $R^1$, $R^2$, $R^{2a}$, $R^{2b}$, $R^3$, $R^4$ and/or $R^5$, for any $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, independently can be a $C_1$ to $C_{30}$ alkyl group; alternatively, a $C_1$ to $C_{20}$ alkyl group; alternatively, a $C_1$ to $C_{15}$ alkyl group; or alternatively, a $C_1$ to $C_{10}$ alkyl group; or alternatively, a $C_1$ to $C_5$ alkyl group. In some embodiments, each $R^1$, $R^2$, $R^{2a}$, $R^{2b}$, $R^3$, $R^4$ and/or $R^5$ group for any $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, independently can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group. In other embodiments, each $R^1$, $R^2$, $R^{2a}$, $R^{2b}$, $R^3$, $R^4$ and/or $R^5$, group for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have and utilize an $R^1$, $R^2$, $R^{2a}$, $R^{2b}$, $R^3$, $R^4$ and/or $R^5$ group, independently can be a phenyl group or a $C_6$ to $C_{30}$ substituted phenyl group; alternatively, a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. General substituent groups are provided herein and these general substituent groups can be utilized to further describe the substituted phenyl groups which can be utilized as $R^1$, $R^2$, $R^{2a}$, $R^{2b}$, $R^3$, $R^4$ and/or $R^5$ for the $N^2$-phosphinyl formamidine compounds, the $N^2$-phosphinyl formamidine transition metal complexes, the $N^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes.

In an aspect, $R^1$ and $R^{2a}$ of the $N^2$-phosphinyl guanidine compounds, the $N^2$-phosphinyl guanidine transition metal complexes, and/or the $N^2$-phosphinyl guanidine chromium complexes can be joined to form a group, $L^{12}$, wherein $L^{12}$, the $N^1$ nitrogen atom, and the $N^3$ nitrogen atom can form a ring or a ring system. In another aspect, $R^3$ and $R^{2b}$ of the $N^2$-phosphinyl guanidine compounds, the $N^2$-phosphinyl guanidine transition metal complexes, and/or the $N^2$-phosphinyl guanidine chromium complexes can be joined to form a group, $L^{23}$, wherein $L^{23}$, the $N^2$ nitrogen atom, and the $N^3$ nitrogen atom can form a ring or a ring system. In an embodiment, $L^{12}$ and/or $L^{23}$ for the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group independently can be an organylene group; alternatively, an organylene group consisting of inert functional groups; or alternatively, a hydrocarbylene group. The organylene group which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group independently can be a $C_2$ to $C_{20}$ organylene group; alternatively, a $C_2$ to $C_{15}$ organylene group; alternatively, a $C_2$ to $C_{10}$ organylene group; or alternatively, a $C_2$ to $C_5$ organylene group. The organylene group consisting of inert functional groups which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group can be a $C_2$ to $C_{20}$ organylene group consisting of inert functional groups; alternatively, a $C_2$ to $C_{15}$ organylene group consisting of inert functional groups; alternatively, a $C_2$ to $C_{10}$ organylene group consisting of inert functional groups; or alternatively, a $C_2$ to $C_5$ organylene group consisting of inert functional groups. The hydrocarbylene group which can be utilized as $L^{12}$ and/or $L^{23}$ of the $N^2$-phosphinyl guanidine compounds, the $N^2$-phosphinyl guanidine transition metal complexes, and/or the $N^2$-phosphinyl guanidine chromium complexes which have an $L^{12}$ group and/or an $L^{23}$ group can be a $C_2$ to $C_{20}$ hydrocarbylene group; alternatively, a $C_2$ to $C_{15}$ hydrocarbylene group; alternatively, a $C_2$ to $C_{10}$ hydrocarbylene group; or alternatively, a $C_2$ to $C_5$ hydrocarbylene group.

In an embodiment, $L^{12}$ and/or $L^{23}$ can be an eth-1,2-ylene group (—$CH_2CH_2$—), an ethen-1,2-ylene group (—CH═CH—), a prop-1,3-ylene group (—$CH_2CH_2CH_2$—), a 1-methylethen-1,2-ylene group (—C($CH_3$)═CH—), a but-1,3-ylene group (—$CH_2CH_2CH(CH_3)$—), a 3-methylbut-1,3-ylene group (—$CH_2CH_2C(CH_3)_2$—), or a phen-1,2-ylene group. In some non-limiting embodiments, $L^{12}$ and/or $L^{23}$ be an eth-1,2-ylene group (—$CH_2CH_2$—), a prop-1,3-ylene group (—$CH_2CH_2CH_2$—), a 1-methylethen-1,2-ylene group (—C($CH_3$)═CH—), a but-1,3-ylene group (—$CH_2CH_2CH(CH_3)$—), or a 3-methylbut-1,3-ylene group (—$CH_2CH_2C(CH_3)_2$—); alternatively, an eth-1,2-ylene group (—$CH_2CH_2$—), an ethen-1,2-ylene group (—CH═CH—), a prop-1,3-ylene group (—CH$_2$CH$_2$CH$_2$—), or a phen-1,2-ylene group; alternatively, an eth-1,2-ylene group (—CH$_2$CH$_2$—) or a prop-1,3-ylene group (—CH$_2$CH$_2$CH$_2$—); alternatively, an ethen-1,2-ylene group (—CH═CH—) or a phen-1,2-ylene group. In other embodiments, L$^{12}$ and/or L$^{23}$ can be an eth-1,2-ylene group (—CH$_2$CH$_2$—); alternatively, an ethen-1,2-ylene group (—CH═CH—); alternatively, a prop-1,3-ylene group (—CH$_2$CH$_2$CH$_2$—); alternatively, a 1-methylethen-1,2-ylene group (—C(CH$_3$)═CH—); alternatively, a but-,3-lene group (—CH$_2$CH$_2$CH(CH$_3$)—); alternatively, a 3-methyl-but-1,3-ylene group (—CH$_2$CH$_2$C(CH$_3$)$_2$—); or alternatively, a phen-1,2-ylene group. In some embodiments, L$^{12}$ or L$^{23}$ can be a —CH═CH—CH═group. In an embodiment, L$^{12}$ can have a structure that can comprise at least one substituent located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex; alternatively, can comprise only one substituent located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex; or alternatively, can comprise two substituents located on the carbon atom attached to the N$^1$ nitrogen atom of the N$^2$-phosphinyl guanidine compound, N$^2$-phosphinyl guanidine transition metal complex, or N$^2$-phosphinyl guanidine chromium complex. In another embodiment, L$^{12}$ can have a structure that can consist of one substituent located on the carbon atom attached to N$^1$ nitrogen atom of the N$^2$-phosphinyl guanidine compound, N$^2$-phosphinyl guanidine transition metal complex, or N$^2$-phosphinyl guanidine chromium complex; or alternatively, can consist of two substituents located on the carbon atom attached to N$^1$ nitrogen atom of the N$^2$-phosphinyl guanidine compound, N$^2$-phosphinyl guanidine transition metal complex, or N$^2$-phosphinyl guanidine chromium complex.

In an embodiment, R$^{2a}$ and R$^{2b}$ of the N$^2$-phosphinyl guanidine compounds, the N$^2$-phosphinyl guanidine transition metal complexes, and/or the N$^2$-phosphinyl guanidine chromium complexes can be joined to form a group, L$^{22}$, wherein R$^{2a}$, R$^{2b}$, and the N$^3$ nitrogen (or L$^{22}$ and the N$^3$ nitrogen) forms a ring or ring system. In an embodiment, L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be an organylene group; alternatively, an organylene group consisting of inert functional groups; or alternatively, a hydrocarbylene group. The organylene group which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_3$ to C$_{20}$ organylene group; alternatively, a C$_3$ to C$_{15}$ organylene group; or alternatively, a C$_3$ to C$_{10}$ organylene group. The organylene group consisting of inert functional groups which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_3$ to C$_{20}$ organylene group consisting of inert functional groups; alternatively, a C$_3$ to C$_{15}$ organylene group consisting of inert functional groups; or alternatively, a C$_3$ to C$_{10}$ organylene group consisting of inert functional groups. The hydrocarbylene group which can be utilized as L$^{22}$ of the N$^2$-phosphinyl guanidine compounds, the N$^2$-phosphinyl guanidine transition metal complexes, and/or the N$^2$-phosphinyl guanidine chromium complexes having an L$^{22}$ group can be a C$_4$ to C$_{20}$ hydrocarbylene group; alternatively, a C$_4$ to C$_{15}$ hydrocarbylene group; or alternatively, a C$_4$ to C$_{10}$ hydrocarbylene group.

In an embodiment, L$^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

In an embodiments, R$^4$ and R$^5$ of the N$^2$-phosphinyl formamidine compounds, the N$^2$-phosphinyl formamidine transition metal complexes, the N$^2$-phosphinyl formamidine chromium complexes, the N$^2$-phosphinyl amidine compounds, the N$^2$-phosphinyl amidine transition metal complexes, the N$^2$-phosphinyl amidine chromium complexes, the N$^2$-phosphinyl guanidine compounds, the N$^2$-phosphinyl guanidine transition metal complexes, and/or the N$^2$-phosphinyl guanidine chromium complexes can be joined to form a ring (regardless of particular type of group—organyl, organyl consisting of inert functional groups, hydrocarbyl, or any species within) containing the phosphorus atom of the N$^2$-phosphinyl formamidine metal complex, the N$^2$-phosphinyl amidine metal complex, and/or the N$^2$-phosphinyl guanidine metal complex. General substituent groups are provided herein and these general substituent groups can be utilized to further describe the substituted phenyl groups which can be utilized as R$^4$ and/or R$^5$ for the N$^2$-phosphinyl formamidine compounds, the N$^2$-phosphinyl formamidine transition metal complexes, the N$^2$-phosphinyl formamidine chromium complexes, the N$^2$-phosphinyl amidine compounds, the N$^2$-phosphinyl amidine transition metal complexes, the N$^2$-phosphinyl amidine chromium complexes, the N$^2$-phosphinyl guanidine compounds, the N$^2$-phosphinyl guanidine transition metal complexes, and/or the N$^2$-phosphinyl guanidine chromium complexes.

Generally, the R$^1$, R$^2$, R$^{2a}$, R$^{2b}$, R$^3$, R$^4$ and/or R$^5$ groups, for any N$^2$-phosphinyl formamidine compounds, the N$^2$-phosphinyl formamidine transition metal complexes, the N$^2$-phosphinyl formamidine chromium complexes, the N$^2$-phosphinyl amidine compounds, the N$^2$-phosphinyl amidine transition metal complexes, the N$^2$-phosphinyl amidine chromium complexes, the N$^2$-phosphinyl guanidine compounds, the N$^2$-phosphinyl guanidine transition metal complexes, and/or the N$^2$-phosphinyl guanidine chromium complexes which have an R$^1$, R$^2$, R$^{2a}$, R$^{2b}$, R$^3$, R$^4$ and/or R$^5$ group, can be independently selected from any group described herein (e.g., any general or specific organyl group, organyl group consisting essentially of inert functional groups, hydrocarbyl group, alkyl group, aromatic group, phenyl group, or substituted phenyl group). In some embodiments, the R$^3$ group, for some of the N$^2$-phosphinyl formamidine compounds, the N$^2$-phosphinyl formamidine transition metal complexes, the N$^2$-phosphinyl formamidine chromium complexes, the N$^2$-phosphinyl amidine compounds, the N$^2$-phosphinyl amidine transition metal complexes, the N$^2$-phosphinyl amidine chromium complexes, the N$^2$-phosphinyl guanidine compounds, the N$^2$-phosphinyl guanidine transition metal complexes, and/or the N$^2$-phosphinyl guanidine chromium complexes described herein can be hydrogen while the R$^1$, R$^2$, R$^{2a}$, R$^{2b}$, R$^4$ and R$^5$, for any N$^2$-phosphinyl formamidine compounds, the N$^2$-phosphinyl formamidine transition metal complexes, the N$^2$-phosphinyl formamidine chromium complexes, the $N^2$-phosphinyl amidine compounds, the $N^2$-phosphinyl amidine transition metal complexes, the $N^2$-phosphinyl amidine chromium complexes, the $N^2$-phosphinyl guanidine compounds, the $N^2$-phosphinyl guanidine transition metal complexes, and/or the $N^2$-phosphinyl guanidine chromium complexes which have an $R^1$, $R^2$, $R^{2a}$, $R^{2b}$, $R^4$ and/or $R^5$ group, can be independently selected from any group described herein (e.g., any general or specific organyl group, organyl group consisting essentially of inert functional groups, hydrocarbyl group, alkyl group, aromatic group, phenyl group, or substituted phenyl group).

In an embodiment, the hereoatomic ligand (whether it is a separate component of the catalyst system or is a ligand complexed to the transition metal compound of the catalyst system) of the catalyst system comprising i) a transition metal compound (e.g., an iron or cobalt compound, among other transition metal compounds disclosed herein), ii) a heteroatomic ligand and iii) a metal alkyl compound or the catalyst system comprising i) a transition metal compound (e.g., an iron or cobalt compound, among other transition metal compounds disclosed herein) complexed to a heteroatomic ligand and ii) a metal alkyl compound can be a pyridine 2,6-bis-imine compound. Generally a pyridine 2,6-bis-imine compound is a compound containing a pyridine 2,6-bis-imine group. Generally, a pyridine 2,6-bis-imine compound group is a group having the structure

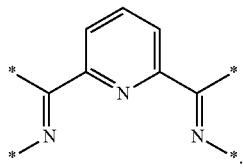

In an embodiment, the heteroatomic ligand of the catalyst system i) an iron or cobalt compound complexed to a heteroatomic ligand and ii) a metal alkyl compound can be an α-diimine compound. Generally, an α-diimine compound is a compound containing an α-diimine group. Generally, an α-diimine group is a group having the structure

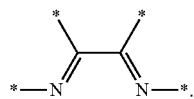

Various aspects and embodiments described herein refer to substituents or non-hydrogen substituents (or alternatively, substituent group). Each substituent or non-hydrogen substituent can be a halide, a hydrocarbyl group, or a hydrocarboxy group; alternatively, a halide or a hydrocarbyl group; alternatively, a halide or a hydrocarboxy group; alternatively, a hydrocarbyl group or a hydrocarboxy group; alternatively, a halide; alternatively, a hydrocarbyl group; or alternatively, a hydrocarboxy group. Each substituent or non-hydrogen substituent of any aspect or embodiment calling for a substituent independently can be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In other embodiments, each substituent or non-hydrogen substituent of any aspect or embodiment calling for a substituent independently can be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group.

In an embodiment, each halide substituent of any aspect or embodiment calling for a substituent or non-hydrogen substituent independently can be a fluoride, chloride, bromide, or iodide; alternatively, a fluoride or chloride. In some embodiments, each halide substituent of any aspect or embodiment calling for a substituent of non-hydrogen substituent independently can be a fluoride; alternatively, a chloride; alternatively, a bromide; or alternatively, an iodide.

In an embodiment, each hydrocarbyl substituent of any aspect or embodiment calling for a substituent or non-hydrogen substituent independently can be an alkyl group, an aryl group, or an aralkyl group; alternatively, an alkyl group; alternatively, an aryl group; or alternatively, an aralkyl group. In an embodiment, each alkyl substituent of any aspect or embodiment calling for a substituent or non-hydrogen substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, each aryl substituent of any aspect or embodiment calling for a substituent or non-hydrogen substituent independently can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an embodiment, each aralkyl substituent of any aspect or embodiment calling for a substituent or non-hydrogen substituent independently can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, each hydrocarboxy substituent of any aspect or embodiment calling for a substituent or non-hydrogen substituent independently can be an alkoxy group, an aryloxy group, or an aralkoxy group; alternatively, an alkoxy group; alternatively, an aryloxy group, or an aralkoxy group. In an embodiment, each alkoxy substituent of any aspect or embodiment calling for a substituent or non-hydrogen substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, each aryloxy substituent of any aspect or embodiment calling for a substituent or non-hydrogen substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an embodiment, each aralkoxy substituent of any aspect or embodiment calling for a substituent or non-hydrogen substituent independently can be benzoxy group.

Generally, the neutral ligand, Q, of the $N^2$-phosphinyl formamidine transition metal complexes, the $N^2$-phosphinyl formamidine chromium complexes, the $N^2$-phosphinyl amidine transition metal complexes, the $N^2$-phosphinyl amidine chromium complexes, the $N^2$-phosphinyl guanidine transition metal complexes, and/or the $N^2$-phosphinyl guanidine chromium complexes, if present, independently can be any neutral ligand that forms an isolatable compound with the $N^2$-phosphinyl formamidine transition metal complex, the $N^2$-phosphinyl formamidine chromium complex, the $N^2$-phosphinyl amidine transition metal complex, the $N^2$-phosphinyl amidine chromium complex, the $N^2$-phosphinyl guanidine transition metal complex, and/or the $N^2$-phosphinyl guanidine chromium complex. In an aspect, each neutral ligand independently can be a nitrile or an ether. In an embodiment, the neutral ligand can be a nitrile; or alternatively, an ether. The number of neutral ligands, q, of the $N^2$-phosphinyl formamidine transition metal complexes, the $N^2$-phosphinyl formamidine chromium complexes, the $N^2$-phosphinyl amidine transition metal complexes, the $N^2$-phosphinyl amidine chromium complexes, the $N^2$-phosphinyl guanidine transition metal complexes, and/or the $N^2$-phosphinyl guanidine chromium complexes can be any number that forms an isolatable compound with the $N^2$-phosphinyl formamidine transition metal complex, the $N^2$-phosphinyl formamidine chromium complex, the $N^2$-phosphinyl amidine transition metal complex, the $N^2$-phosphinyl amidine chromium complex, the $N^2$-phosphinyl guanidine transition metal complex, and/or the $N^2$-phosphinyl guanidine chromium complex. In an aspect, the number of neutral ligands can be from 0 to 6; alternatively, 0 to 3; alternatively, 0; alternatively, 1; alternatively, 2; alternatively, 3; or alternatively, 4.

Generally, each neutral nitrile ligand independently can be a $C_2$ to $C_{20}$ nitrile; or alternatively, a $C_2$ to $C_{10}$ nitrile. In an embodiment, each neutral nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some embodiments, each neutral nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an embodiment, each neutral nitrile ligand independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each neutral ether ligand independently can be a $C_2$ to $C_{40}$ ether; alternatively, a $C_2$ to $C_{30}$ ether; or alternatively, a $C_2$ to $C_{20}$ ether. In an embodiment, each neutral ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some embodiments, each neutral ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other embodiments, each neutral ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some embodiments, each neutral ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, isobenzofuran; alternatively, dibenzofuran; alternatively, diphenyl ether; or alternatively, a ditolyl ether.

The metal alkyl compound which can be utilized in any catalyst system described herein can be any heteroleptic or homoleptic metal alkyl compound. In an embodiment, the metal alkyl can comprise, can consist essentially of, or can consist of, a non-halide metal alkyl, a metal alkyl halide, or any combination thereof; alternatively, a non-halide metal alkyl; or alternatively, a metal alkyl halide.

In an embodiment, the metal of the metal alkyl compound can comprise, can consist essentially of, or can consist of, a group 1, 2, 11, 12, 13, or 14 metal; or alternatively, a group 13 or 14 metal; or alternatively, a group 13 metal. In some embodiments, the metal of the metal alkyl compound (non-halide metal alkyl or metal alkyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some embodiments, the metal alkyl compound (non-halide metal alkyl or metal alkyl halide) can comprise, can consist essentially of, or can consist of, a lithium alkyl compound, a sodium alkyl compound, a magnesium alkyl compound, a boron alkyl compound, a zinc alkyl compound, or an alkylaluminum compound. In some embodiments, the metal alkyl (non-halide metal alkyl or metal alkyl halide) can comprise, can consist essentially of, or can consist of, an alkylaluminum compound.

In an embodiment, the alkylaluminum compound can be a trialkylaluminum, an alkylaluminum halide, an alkylaluminum alkoxide, an aluminoxane, or any combination thereof. In some embodiments, the alkylaluminum compound can be a trialkylaluminum, an alkylaluminum halide, an aluminoxane, or any combination thereof; a trialkylaluminum, an alkylaluminum halide, or any combination thereof; or alternatively, a trialkylaluminum, an aluminoxane, or any combination thereof. In other embodiments, the alkylaluminum compound can be a trialkylaluminum; alternatively, an alkylaluminum halide; alternatively, an alkylaluminum alkoxide; or alternatively, an aluminoxane.

In a non-limiting embodiment, the aluminoxane can have a repeating unit characterized by the Formula I:

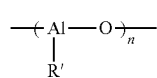

Formula I wherein R' is a linear or branched alkyl group. Alkyl groups for metal alkyl compounds are independently described herein and can be utilized without limitation to further describe the aluminoxanes having Formula I. Generally, n of Formula I can be greater than 1; or alternatively, greater than 2. In an embodiment, n can range from 2 to 15; or alternatively, range from 3 to 10.

In an aspect, each halide of any metal alkyl halide disclosed herein independently can be fluoride, chloride, bromide, or iodide; alternatively, chloride, bromide, or iodide. In an embodiment, each halide of any metal alkyl halide disclosed herein can be fluoride; alternatively, chloride; alternatively, bromide; or alternatively, iodide.

In an aspect, each alkyl group of any metal alkyl compound disclosed herein (non-halide metal alkyl or metal alkyl halide) independently can be a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) of any metal alkyl compound disclosed herein (non-halide metal alkyl or metal alkyl halide) independently can be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, alkyl group independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any metal alkyl alkoxide disclosed herein independently can be a $C_1$ to $C_{20}$ alkoxy group; alternatively, a $C_1$ to $C_{10}$ alkoxy group; or alternatively, a $C_1$ to $C_6$ alkoxy group. In an embodiment, each alkoxide group of any metal alkyl alkoxide disclosed herein independently can be a methoxy group, an ethoxy group, a propoxy group, a butoxy group, a pentoxy group, a hexoxy group, a heptoxy group, or an octoxy group; alternatively, a methoxy group, a ethoxy group, a butoxy group, a hexoxy group, or an octoxy group. In some embodiments, each alkoxide group of any metal alkyl alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting embodiment, the metal alkyl compound can be, comprise, or consist essentially of, methyl lithium, n-butyl lithium, sec-butyl lithium, tert-butyl lithium, diethyl magnesium, di-n-butylmagnesium, ethylmagnesium chloride, n-butylmagnesium chloride, or diethyl zinc.

In a non-limiting embodiment, the trialkylaluminum compound can comprise, can consist essentially of, or can be, trimethylaluminum, triethylaluminum, tripropylaluminum, tributylaluminum, trihexylaluminum, trioctylaluminum, or mixtures thereof. In some non-limiting embodiments, the trialkylaluminum compound can comprise, can consist essentially of, or can be, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting embodiments, the trialkylaluminum compound can comprise, can consist essentially of, or can be, trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting embodiment, the alkylaluminum halide can comprise, can consist essentially of, or can be, diethylaluminum chloride, diethylaluminum bromide, ethylaluminum dichloride, ethylaluminum sesquichloride, and mixtures thereof. In some non-limiting embodiments, the alkylaluminum halide can comprise, can consist essentially of, or can be, diethylaluminum chloride, ethylaluminum dichloride, ethylaluminum sesquichloride, and mixtures thereof. In other non-limiting embodiments, the alkylaluminum halide can comprise, can consist essentially of, or can be, diethylaluminum chloride; alternatively, diethylaluminum bromide; alternatively, ethylaluminum dichloride; or alternatively, ethylaluminum sesquichloride.

In a non-limiting embodiment, the aluminoxane can comprise, can consist essentially of, or can be, methylaluminoxane (MAO), ethylaluminoxane, modified methylaluminoxane (MMAO), n-propylaluminoxane, iso-propylaluminoxane, n-butylaluminoxane, sec-butylaluminoxane, iso-butylaluminoxane, t-butylaluminoxane, 1-pentyl-aluminoxane, 2-entylaluminoxane, 3-pentyl-aluminoxane, iso-pentyl-aluminoxane, neopentylaluminoxane, or mixtures thereof. In some non-limiting embodiments, the aluminoxane can comprise, can consist essentially of, or can be, methylaluminoxane (MAO), modified methylaluminoxane (MMAO), isobutyl aluminoxane, t-butyl aluminoxane, or mixtures thereof. In other non-limiting embodiments, the aluminoxane can comprise, can consist essentially of, or can be, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentyl-aluminoxane.

In an embodiment, the halogen containing compound can comprise a chloride containing compound, a bromide containing compound, an iodide containing compound, or any combination thereof. In an embodiment, the halogen containing compound, regardless of whether it is a chloride, bromide, or iodide containing compound, can comprise a metal halide, alkyl metal halide, or an organic halide; alternatively, a metal halide; alternatively, an alkyl metal halide; or alternatively, an organic halide. In additional or alternative embodiments, the halogen containing compound can comprise a group 3 metal halide, a group 4 metal halide, a group 5 metal halide, a group 13 metal halide, a group 14 metal halide, a group 15 metal halide, or any combination thereof. By way of example, the halogen containing compound can comprise scandium chloride, yttrium chloride, lanthanum chloride, titanium tetrachloride, zirconium tetrachloride, hafnium tetrachloride, boron trichloride, aluminum chloride, gallium chloride, silicon tetrachloride, trimethyl chlorosilane, germanium tetrachloride, tin tetrachloride, phosphorus trichloride, antimony trichloride, antimony pentachloride, bismuth trichloride, boron tribromide, aluminum tribromide, silicon tetrachloride, silicon tetrabromide, aluminum fluoride, molybdenum pentachloride, tungsten hexachloride, trityl hexachloroantimonate, or any combination thereof.

In additional or alternative embodiments, the halogen containing compound can comprise a dialkylaluminum halide, an alkylaluminum dihalide, or an alkylaluminum sesquihalide, or any combination thereof. Moreover and in this aspect, the halogen containing compound can comprise diethylaluminum chloride, ethylaluminum sesquichloride, ethylaluminum dichloride, tributyltin chloride, dibutyltin dichloride, or any combination thereof; alternatively, diethylaluminum chloride, ethylaluminum sesquichloride, ethylaluminum dichloride or any combination thereof. In additional or alternative embodiments, the halogen containing compound can comprise a $C_1$ to $C_{15}$ organic halide; alternatively, a $C_1$ to $C_{10}$ organic halide; alternatively, a $C_1$ to $C_8$ organic halide. By way of example, according to this aspect, the halogen containing compound can comprise carbon tetrachloride, carbon tetrabromide, chloroform, bromoform, dichloromethane, dibromoethane, diiodomethane, chloromethane, bromomethane, iodomethane, dichloroethane, tetrachloroethane, trichloroacetone, hexachloroacetone, hexachlorocyclohexane, 1,3,5-trichlorobenzene, hexachlorobenzene, trityl chloride, benzyl chloride, benzyl bromide, benzyl iodide, chlorobenzene, bromobenzene, iodobenzene, hexafluorobenzene, or any combination thereof.

In an aspect, the catalyst system to which the present invention can be applied can be selected from a catalyst system comprising a) a transition metal compound, a pyrrole compound, a metal alkyl compound, and optionally, a halide containing compound, b) a transition metal compound, a diphosphinoaminyl compound, and a metal alkyl compound, c) a transition metal compound complexed to a diphosphinoaminyl compound, and a metal alkyl compound, d) a transition metal compound, an $N^2$-phosphinylamidine compound, and a metal alkyl compound, e) a transition metal compound complexed to an $N^2$-phosphinylamidine compound, and a metal alkyl compound, f) a transition metal compound, an $N^2$-phosphinylformamidine compound, and a metal alkyl compound, g) a transition metal compound complexed to an $N^2$-phosphinylformamidine compound, and a metal alkyl compound, h) a transition metal compound, an $N^2$-phosphinyl guanidine compound, and a metal alkyl compound, i) a transition metal compound complexed to an $N^2$-phosphinyl guanidine compound, and a metal alkyl compound, and j) combinations thereof. In another aspect, the catalyst system to which the present invention can be applied can be selected from a catalyst system comprising a) a chromium compound, a pyrrole compound, a metal alkyl compound, and optionally, a halide containing compound, b) a chromium compound, a diphosphinoaminyl compound, and a metal alkyl compound, c) a chromium compound complexed to a diphosphinoaminyl compound, and a metal alkyl compound, d) a chromium compound, an $N^2$-phosphinylamidine compound, and a metal alkyl compound, e) a chromium compound complexed to an $N^2$-phosphinylamidine compound, and a metal alkyl compound, f) a chromium compound, an $N^2$-phosphinylformamidine compound, and a metal alkyl compound, g) a chromium compound complexed to an $N^2$-phosphinylformamidine compound, and a metal alkyl compound, h) a chromium compound, an $N^2$-phosphinyl guanidine compound, and a metal alkyl compound, i) a chromium compound complexed to an $N^2$-phosphinyl guanidine compound, and a metal alkyl compound, and j) combinations thereof.

In an embodiment, the catalyst system can comprise a i) transition metal compound, ii) an amine, amide, or imide compound, iii) a metal alkyl compound, and iv) optionally, a halide containing compound. In an embodiment, the catalyst system can comprise i) a chromium compound, ii) an amine, amide, or imide compound, iii) a metal alkyl compound, and iv) optionally, a halide containing compound. In some embodiments, the catalyst system can comprise a i) chromium compound, ii) a pyrrole compound, iii) a metal alkyl compound, and iv) optionally, a halide containing compound. For purposes of the disclosure herein, the catalyst system using a pyrrole compound can be referred to as a chromium-pyrrole catalyst system. The chromium-pyrrole catalyst system can be an ethylene trimerization catalyst system where the specified oligomerization product (or trimerization product) typically comprises at least 70 wt. % hexenes. In some chromium-pyrrole catalyst system embodiments, the chromium compound can comprise, or consist essentially of, a chromium carboxylate and the alkylaluminum compound can comprise, or consist essentially of, a trialkylaluminum compound, a dialkylaluminum halide, an alkylaluminum dihalide, an alkylaluminum sesquihalide, or any combination thereof. In some chromium-pyrrole catalyst system embodiments, the optional halide containing compound can be an organo halide compound, a metal halide compound (e.g., an inorganic metal halide compound or an alkyl metal halide compound), or a combination thereof. In a chromium-pyrrole catalyst system embodiment, the catalyst system can comprise chromium (III) 2-ethylhexanoate, 2,5-dimethyl pyrrole, triethylaluminum, and diethylaluminum chloride. Additional information regarding the use of chromium-pyrrole catalyst systems for oligomerizing (or trimerizing) ethylene (including specific examples) can be found in, but not limited to, U.S. Pat. Nos. 5,198,563, 5,288,823, EP 608447A1, U.S. Pat. Nos. 5,331,104, 5,340,785, 5,360,879, 5,376,612, 5,382,738, 5,399,539, 5,438,027, 5,470,926, 5,543,375, 5,523,507, 5,563,312, EP 706983A1, U.S. Pat. Nos. 5,689,028, 5,750,816, 5,763,723, 5,814,575, 5,856,257, 5,856,612, 5,859,303, 5,910,619, 6,133,495, 6,380,451, 6,455,648, 7,157,612, 7,384,886, 7,476,775, 7,718,838, 7,820,581, 7,910,670, 8,049,052, 8,329,608, 8,344,198, 8,471,085, US 2010/0036185, US 2010/0113257, US 2010/0113851, US 2010/0113852, US 2013/0150605, US 2010/0331503, or US 2013/0150642.

In an embodiment, the catalyst system can comprise i) a transition metal compound, ii) a diphosphinoaminyl compound, and iii) a metal alkyl compound; or alternatively, i) a transition metal compound complexed to a diphosphinoaminyl compound, and ii) a metal alkyl compound. In another embodiment, the catalyst system can comprise i) a chromium compound, ii) a diphosphinoaminyl compound, and iii) a metal alkyl compound; or alternatively, i) a chromium compound complexed to a diphosphinoaminyl compound, and ii) a metal alkyl compound. For purposes of the disclosure herein, these chromium based catalyst systems can be generically referred to as chromium-PNP catalyst systems. Depending upon the diphosphinoaminyl compound, the chromium-PNP catalyst systems can be an ethylene tetramerization catalyst system where the specified oligomer comprises at least 70 wt. % octenes or a trimerization and tetramerization catalyst system where the specified oligomer comprises at least 70 wt. % hexenes and octenes. In some chromium-PNP catalyst system embodiments, the chromium compound of the catalyst system or the chromium compound of the chromium compound complexed to a diphosphinoaminyl compound, can comprise, or consist essentially of, a chromium halide, carboxylate, 3-diketonate, hydrocarboxide, nitrate, sulfate, phosphate, or chlorate; alternatively, a chromium halide, carboxylate, or 3-diketonate; alternatively, a chromium halide; alternatively, a chromium carboxylate; or alternatively, chromium 3-diketonate. In some chromium-PNP catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an aluminoxane, or combinations thereof; or alternatively, comprises an aluminoxane. Additional information regarding the use of chromium-PNP catalyst systems for oligomerizing ethylene (including specific examples) can be found in, but not limited to, U.S. Pat. Nos. 7,285,607, 7,297,832, 7,323,524, 7,378,537, 7,511,183, 7,525,009, 7,829,749, 7,906,681, 7,964,763, 7,994,363, 8,076,523, 8,134,038, 8,252,956, 8,252,955, 8,268,941, 8,334,420, 8,367,786, 8,461,406, US 2009/0306442, US 2011/0257350, US 2011/0282016, US 2012/0041241, US 2012/0088933, US 2012/0101321, US 2012/0142989, US 2012/0199467, US 2012/0271087, US 2012/0316303, and WO 2013/013300.

In another embodiment, the catalyst system can comprise i) a transition metal compound, ii) an $N^2$-phosphinylamidine compound, and iii) a metal alkyl compound; or alternatively, i) a transition metal compound complexed to an $N^2$-phosphinylamidine compound, and ii) a metal alkyl compound. In another embodiment, the catalyst system can comprise i) a chromium compound, ii) an $N^2$-phosphinylamidine compound, and iii) a metal alkyl compound. In another embodiment, the catalyst system can comprise i) a chromium compound complexed to an $N^2$-phosphinylamidine compound, and ii) a metal alkyl compound. For purposes of the disclosure herein, these chromium based catalyst systems can be generically referred to as chromium-$N^2$-phosphinylamidine catalyst systems. Depending upon the $N^2$-phosphinylamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylamidine catalyst system embodiments, the chromium compound of the catalyst system or the chromium compound of the chromium compound complexed to a $N^2$-phosphinylamidine compound, can comprise, or consist essentially of, a chromium halide, carboxylate, 3-diketonate, hydrocarboxide, nitrate, or chlorate; alternatively, a chromium halide, carboxylate, hydrocarboxide, or 3-diketonate; alternatively, a chromium halide; alternatively, a chromium carboxylate; alternatively, a chromium hydrocarboxide; or alternatively, chromium 3-diketonate. In some chromium-$N^2$-phosphinylamidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an aluminoxane. Additional information regarding the use of chromium-$N^2$-phosphinylamidine catalyst systems for oligomerizing ethylene (including specific examples) can be found in, but not limited to, U.S. Pat. No. 8,680,003.

In another embodiment, the catalyst system can comprise i) a transition metal compound, ii) an $N^2$-phosphinylformamidine compound, and iii) a metal alkyl compound; or alternatively, i) a transition metal compound complexed to an $N^2$-phosphinylformamidine compound, and ii) a metal alkyl compound. In another embodiment, the catalyst system can comprise i) a chromium compound, ii) an $N^2$-phosphinylformamidine compound, and iii) a metal alkyl compound. In another embodiment, the catalyst system can comprise i) a chromium compound complexed to an $N^2$-phosphinylformamidine compound and ii) a metal alkyl compound. For purposes of the disclosure herein, these chromium based catalyst systems can be generically referred to as chromium compound-$N^2$-phosphinylformamidine catalyst systems. Depending upon the $N^2$-phosphinylformamidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylforamidine catalyst system embodiments, the chromium compound of the catalyst system or the chromium compound of the chromium compound complexed to a $N^2$-phosphinylforamidine compound, can comprise, or consist essentially of, a chromium halide, carboxylate, 3-diketonate, hydrocarboxide, nitrate, or chlorate; alternatively, a chromium halide, carboxylate, hydrocarboxide, or 3-diketonate; alternatively, a chromium halide; alternatively, a chromium carboxylate; alternatively, a chromium hydrocarboxide; or alternatively, chromium 3-diketonate. In some chromium-$N^2$-phosphinylforamidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an aluminoxane. Additional information regarding the use of the chromium compound-$N^2$-phosphinylformamidine catalyst systems for oligomerizing ethylene (including specific examples) can be found in, but not necessarily limited to, PCT patent application PCT/US13/75936.

In yet another embodiment, the catalyst system can comprise i) a transition metal compound, ii) an $N^2$-phosphinylguanidine compound, and iii) a metal alkyl compound; or alternatively, i) a transition metal compound complexed to an $N^2$-phosphinylguanidine compound, and ii) a metal alkyl compound. In yet another embodiment, the catalyst system can comprise i) a chromium compound, ii) an $N^2$-phosphinylguanidine compound, and iii) a metal alkyl compound. In still another embodiment, the catalyst system can comprise i) a chromium compound complexed to an $N^2$-phosphinylguanidine compound, and ii) a metal alkyl compound. For purposes of the disclosure herein, these chromium based catalyst systems can be generically referred to as chromium compound-$N^2$-phosphinylguanidine catalyst systems. Depending upon the $N^2$-phosphinyl guanidine compound, these catalyst systems can be an ethylene trimerization catalyst system where the specified oligomer comprises at least 70 wt. % hexenes or a trimerization and tetramerization catalyst system where the specified oligomer comprises at least 70 wt. % hexenes and octenes. In some chromium-$N^2$-phosphinylguanidine catalyst system embodiments, the chromium compound of the catalyst system or the chromium compound of the chromium compound complexed to a $N^2$-phosphinylguanidine compound, can comprise, can consist essentially of, or can be, a chromium halide, carboxylate, 3-diketonate, hydrocarboxide, nitrate, or chlorate; alternatively, a chromium halide, carboxylate, hydrocarboxide, or 3-diketonate; alternatively, a chromium halide; alternatively, a chromium carboxylate; alternatively, a chromium hydrocarboxide; or alternatively, chromium 3-diketonate. In some chromium-$N^2$-phosphinylguanidine catalyst system embodiments, the alkylaluminum compound can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an aluminoxane. Additional information regarding the use of chromium compound-$N^2$-phosphinylguanidine catalyst systems for oligomerizing ethylene (including specific examples) can be found in, but not necessarily limited to, US 2013/0331629.

In an embodiment, the catalyst system can comprise, or consist essentially of, an organometallic compound comprising a trialkylaluminum compound; or alternatively, the catalyst system comprises an organometallic compound consisting essentially of, a trialkylaluminum compound. These catalyst systems represent a broad range ethylene oligomerization catalyst system where the oligomerization product distribution can be described equation $K=X_{q+1}/X_q$ wherein $X_{q+1}$ is the number of moles of oligomerization product produced having q+1 monomer units and $X_q$ is the number of moles of oligomerization product produced having q monomer units. K is often referred to as the Schulz-Flory chain growth factor. In some embodiments, the trialkylaluminum compound can be a $C_3$ to $C_{20}$, a $C_3$ to $C_{20}$, a $C_6$ to $C_{20}$, or $C_6$ to $C_{15}$ compound. In other embodiments, the trialkylaluminum compound can be triethylaluminum, tri-n-butylaluminum, or any combination of triethylaluminum and tri-n-butylaluminum; or alternatively, triethylaluminum. In an embodiment, the oligomerization of ethylene using the trialkylaluminum based catalyst systems can be performed in a $C_4$ to $C_{40}$ hydrocarbon solvent. The trialkylaluminum based catalyst systems for oligomerizing ethylene can be operated at any pressure (or any ethylene partial pressure) disclosed herein (e.g., 500 psig to 5,000 psig, 1,000 psig to 5,000 psig, 2,000 psig to 5,000 psig, among other pressure or ethylene partial pressures disclosed herein). In an embodiment, the oligomerization of ethylene using the trialkylaluminum based catalyst systems can be performed at any temperature disclosed herein; or alternatively at a temperature ranging from 170° C. to 240° C., 180° C. to 230° C., or 185° C. to 225° C. Additional information regarding these trialkylaluminum based catalyst systems for oligomerizing ethylene (including specific examples) can be found in, but not necessarily limited to, U.S. Pat. Nos. 3,441,631, 3,444,263, 3,444,264, 3,477,813, 3,478,124, 3,482,200, 3,502,741, 3,510,539, 3,531,253, 3,562,348, 3,641,191, 3,702,345, 4,022,839, 5,345,022, 5,510,556, and GB 1,186,609.

In an embodiment, the catalyst system can comprise a nickel compound and a bidentate organophosphine having at least one tertiary organophosphorus group; or alternatively, a complex of a nickel compound and a bidentate organophosphine having at least one tertiary organophosphorus group. In a further embodiment, these catalyst systems can further comprise an active hydride compound. The catalyst systems using the nickel compound and a bidentate organophosphine can be referred to as a nickel-phosphine catalyst system. The nickel-phosphine catalyst systems represent a broad range ethylene oligomerization catalyst system where the oligomerization product distribution can be described equation $K=X_{q+1}/X_q$ wherein $X_{q+1}$ is the number of moles of oligomer product produced having q+1 monomer units and $X_q$ is the number of moles of oligomerization product produced having q monomer units. K is often referred to as the Schulz-Flory chain growth factor. In some embodiments, the nickel compound can be a nickel(II) salt such as nickel (II) halides, carbonates, ferrocyanide, nitrate, chlorate, sulfate, carboxylate (which can be any carboxylate anion as described herein), sulfonate, citrate, and beta-dionate (which can be any beta-dionate anion described herein) and can include these nickel(II) salts which further contain water of hydration. In other embodiments, the nickel compound can be a nickel compound comprising a $C_2$ to $C_{20}$ olefinically unsaturated compound. In some embodiments the nickel compound comprising a $C_2$ to $C_{20}$ olefinically unsaturated compound can be a nickel(0) compound having a $C_2$ to $C_{20}$ olefinically unsaturated compound or a nickel(II) compound comprising a $C_2$ to $C_{20}$ $\pi$-allyl anion; alternatively, a nickel (0) compound having a $C_2$ to $C_{20}$ olefinically unsaturated compound; or alternatively a nickel(II) compound comprising a $C_2$ to $C_{20}$ $\pi$-allyl anion. In an embodiment, the bidentate organophosphine can be a $C_8$ to $C_{30}$ or $C_{10}$ to $C_{20}$ organophosphine having a tertiary organophosphorus group and a functional group on the carbon attached to, separated by one carbon atom from, or separated by two carbon atoms from, the phosphorus atom of the organophosphorus group. In an embodiment, the functional group can be a carboxylic acid group, a carboxylate group, a N,N-dihydrocarbylcarboxamide group, a hydroxy group, or an hydrocarboxy group. In an embodiment, the active hydride compound can be boron hydride compound (e.g., sodium, potassium, or lithium borohydride, among other boron hydride compounds). In some embodiments, an ethylene oligomerization using the nickel-phosphine catalyst system can be performed using an aliphatic diol or an aliphatic diol/monoalcohol mixture as a reaction solvent. Additional information regarding these nickel based catalyst systems for oligomerizing ethylene (including specific examples) can be found in, but not necessarily limited to, U.S. Pat. Nos. 3,636,091, 3,644,563, 3,647,915, 3,676,523, 3,737,475, 3,686,159, 3,686,351, 3,825,615, 4,020,121, 4,229,607, 4,260,844, 4,284,837, 4,377,499, 4,472,522, 4,472,525, 4,503,279, 4,503,280, 4,528,416, 5,557,027, 6,825,148, CA 985,294, EP 177,999,

*Chem. Eng. Proc.,* 1979, January, pp. 73-76, *Organometallics,* 1983, 2, pp. 594-597, and *Angew. Chem. Int. Ed.* 2013, 52, pp. 12492-12496.

In another embodiment, the catalyst system can comprise i) a zirconium halide, hydrocarbyloxide, or carboxylate, and ii) a metal alkyl compound; or alternatively i) a zirconium halide, hydrocarbyloxide, or carboxylate, ii) a Lewis base, and iii) a metal alkyl compound. These catalyst systems represent a broad range ethylene oligomerization catalyst system where the oligomerization product distribution can be described equation $K=X_{q+1}/X_q$ wherein $X_{q+1}$ is the number of moles of oligomerization product produced having q+1 monomer units and $X_q$ is the number of moles of oligomerization product produced having q monomer units. K is often referred to as the Schulz-Flory chain growth factor. In an embodiment, the zirconium halide can have the formula $ZrX_4$ where each X independently can be chloride, bromide or iodide; alternatively, chloride; or alternatively bromide. In an embodiment, the zirconium carboxylate can have the formula $ZrY_4$ where Y can be a $C_1$ to $C_{10}$ or $C_1$ to $C_5$ carboxylate. In some embodiment, the zirconium halide/zirconium carboxylate can be combined in a single zirconium compound having the formula $ZrX_cY_{4-c}$ wherein each X independently can be any halide disclosed herein, each Y independently can be any carboxylate disclosed herein, and c can be 1, 2, or 3. In an embodiment, the zirconium hydrocarbyloxide can be a $C_1$ to $C_{20}$, a $C_1$ to $C_{10}$, a $C_1$ to $C_{10}$, or a $C_1$ to $C_4$ hydrocarbyloxide; alternatively, a $C_6$ to $C_{20}$ or a $C_6$ to $C_{10}$ aryloxide; or alternatively, a $C_1$ to $C_{20}$, a $C_1$ to $C_{10}$, a $C_1$ to $C_{10}$, or a $C_1$ to $C_4$ alkoxide. In some embodiment, the zirconium halide/zirconium hydrocarbyloxide can be combined in a single zirconium compound having the formula $ZrX_cZ_{4-c}$ wherein each X independently can be any halide disclosed herein, each Z independently can be any hydrocarbyloxide disclosed herein, and c can be 1, 2, or 3. In an embodiment, the Lewis base can be a $C_3$ to $C_{30}$ ester, a $C_3$ to $C_{30}$ ketone, $C_2$ to $C_{30}$ ether, a $C_2$ to $C_{20}$ dihydrocarbylsulfide, a $C_2$ to $C_{20}$ dihydrocarbyldisulfides, a $C_4$ to $C_{20}$ thiophene or tetrahydrothiophene, thiourea, a $C_3$ to $C_{30}$ trihydrocarbylphosphine, a $C_1$ to $C_{10}$ monohydrocarbylamine, a $C_2$ to $C_{20}$ dihydrocarbylamine, a $C_3$ to $C_{30}$ trihydrocarbylamine, a $C_3$ to $C_{30}$ nitrile, a $C_4$ to $C_{30}$ carboxylic acid anhydride, $C_2$ to $C_{30}$ carboxylic acid halide, $C_2$ to $C_{30}$ amide, a $C_2$ to $C_{30}$ aldehyde, or any combination thereof; a $C_3$ to $C_{30}$ ester, a $C_3$ to $C_{30}$ ketone, $C_2$ to $C_{30}$ ether, a $C_3$ to $C_{30}$ nitrile, a $C_4$ to $C_{30}$ carboxylic acid anhydride, $C_2$ to $C_{30}$ carboxylic acid halide, $C_2$ to $C_{30}$ amide, a $C_2$ to $C_{30}$ aldehyde, or any combination thereof; or alternatively, a $C_2$ to $C_{20}$ dihydrocarbylsulfide, a $C_2$ to $C_{20}$ dihydrocarbyldisulfides, a $C_4$ to $C_{20}$ thiophene or tetrahydrothiophene, thiourea, a $C_3$ to $C_{30}$ trihydrocarbylphosphine, a $C_1$ to $C_{10}$ monohydrocarbylamine, a $C_2$ to $C_{20}$ dihydrocarbylamine, a $C_3$ to $C_{30}$ trihydrocarbylamine, or any combination thereof. In some embodiments, the metal alkyl compound can comprise, can consist essentially of, or can be, any metal alkyl compound disclosed herein where the alkyl group can be any alkyl group disclosed herein for the metal alkyl compound; alternatively, can comprise, can consist essentially of, or can be, a dialkylzinc compound where each alkyl group independently can be a $C_1$ to $C_{20}$, a $C_1$ to $C_{10}$, or a $C_1$ to $C_4$ alkyl group; alternatively, can comprise, can consist essentially of, or can be, any alkylaluminum compound disclosed herein; or alternatively, can be or comprise an alkylaluminum compound having the formula $AlR_nX_{3-n}$ where R can be any alkyl group for a metal alkyl compound disclosed herein, X can be any halide for a metal alkyl halide disclosed herein, and n can be 1, 1.5, 2, or 3. In some embodiments, these zirconium base catalyst system can produce an ethylene oligomerization product having a K value ranging from 0.4 to 0.9; alternatively, from 0.4 to 0.8; alternatively, from 0.5 to 0.8; alternatively, from 0.5 to 0.7; alternatively, from 0.55 to 0.7. Additional information regarding these zirconium based catalyst systems for oligomerizing ethylene (including specific examples) can be found in, but not necessarily limited to, U.S. Pat. Nos. 4,361,714, 4,377,720, 4,396,788, 4,409,414, 4,410,750, 4,434,312, 4,434,313, 4,442,309, 4,486,615, 4,783,573, 4,855,525, 4,886,933, 4,966,874, 5,260,500, 6,576,721, US 2003/0153798, U.S. Pat. Nos. 7,169,961, 7,291,685, 7,566,679, US 2009/0216057, US 2009/0306312, US 2010/0191029, US 2010/0292423, US 2011/0046429, US 2011/0054130, U.S. Pat. No. 7,897,826, US 2011/0054233, US 2012/0184692, U.S. Pat. No. 8,269,055, EP 320,571 A2, EP 444,505 A2, EP 1,749,807 A1, EP 1,752,434 A1, EP 1,780,189, EP 2,258,674 A1, WO 91/02707, *Sekiyu Gakkaishi,* Vol. 37, No. 4, 1994, pp. 337-346, *Sekiyu Gakkaishi,* Vol. 42, No. 4, 1999, pp. 235-245, *Sekiyu Gakkaishi,* Vol. 43, No. 5, 2000, pp. 328-338, *Sekiyu Gakkaishi,* Vol. 44, No. 1, 2001, pp. 25-35, and *Sekiyu Gakkaishi,* Vol. 44, No. 2, 2001, pp. 109-119.

In an embodiment, the catalyst system can comprise a transition metal compound, a pyridine 2,6-bis-imine compound, and a metal alkyl compound; or alternatively, a transition metal complex comprising a transition metal compound complexed to a pyridine 2,6-bisimine compound and a metal alkyl compound. In another embodiment, the catalyst system can comprise an iron or cobalt compound, a pyridine 2,6-bis-imine compound, and a metal alkyl compound; or alternatively, an iron or cobalt complex comprising an iron or cobalt compound complexed to pyridine 2,6-bis-imine compound and a metal alkyl compound. In still another embodiment, the catalyst system can comprise an iron halide, a pyridine 2,6-bis-imine compound, and a metal alkyl compound; or alternatively an iron halide complexed to pyridine 2,6-bis-imine compound and a metal alkyl compound. These catalyst systems can be generically referred to as iron or cobalt-pyridine 2,6-bis-imine catalyst systems. The iron or cobalt-pyridine 2,6-bis-imine catalyst systems can be utilized in ethylene oligomerization wherein they represent a broad range ethylene oligomerization catalyst system where the oligomerization product distribution can be described equation $K=X_{q+1}/X_q$ wherein $X_{q+1}$ is the number of moles of oligomerization product produced having q+1 monomer units and $X_q$ is the number of moles of oligomerization product produced having q monomer units. K is often referred to as the Schulz-Flory chain growth factor. In some iron or cobalt-pyridine 2,6-bis-imine catalyst systems embodiments can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. In some embodiments, the iron or cobalt-pyridine 2,6-bis-imine catalyst system can produce an ethylene oligomerization product having a K value ranging from 0.4 to 0.9; alternatively, from 0.4 to 0.8; alternatively, from 0.5 to 0.8; alternatively, from 0.5 to 0.7; alternatively, from 0.55 to 0.7. Additional information regarding the iron or cobalt-pyridine 2,6-bis-imine catalyst system and the use of iron or colbalt-α-diimine catalyst systems for oligomerizing ethylene (including specific examples) can be found in, but not necessarily limited to, U.S. Pat. Nos. 5,955,555, 6,103,946, 6,291,733, 6,489,497, 6,451,939, 6,455,660, 6,458,739, 6,472,341, 6,545,108, 6,559,091, 6,657,026, 6,683,187, 6,710,006, 6,911,505, 6,911,506, 7,001,964, 7,045,632, 7,049,442, 7,056,997, 7,223,893, 7,456,284, 7,683,149, 7,902,415, 7,994,376, US 2013/0172651, and EP 1229020A1.

In an embodiment, the catalyst system can comprise a transition metal complex comprising a transition metal compound complexed to an α-diimine compound and a metal alkyl compound. In another embodiment, the catalyst system can comprise an iron or cobalt compound complexed to an α-diimine compound and a metal alkyl compound. These catalyst systems can be generically referred to as iron or colbalt-α-diimine catalyst systems. The iron or colbalt-α-diimine catalyst systems can be utilized in ethylene oligomerization wherein they represent a broad range ethylene oligomerization catalyst system where the oligomerization product distribution can be described equation $K=X_{q+1}/X_q$ wherein $X_{q+1}$ is the number of moles of oligomerization product produced having q+1 monomer units and $X_q$ is the number of moles of oligomerization product produced having q monomer units. K is often referred to as the Schulz-Flory chain growth factor. In some iron or colbalt-α-diimine catalyst systems embodiments, the iron or cobalt compound complexed to α-diimine compound, can comprise, can consist essentially of, or can be, an iron halide (e.g., iron(III) chloride) complexed to an α-diimine compound (e.g., an α-diimine compound having an α-diimine group; or alternatively, an iron halide (e.g., iron(III) chloride) complexed to an α-diimine compound where the α-diimine compound comprises a α-diimine group, a first imine nitrogen group comprising a substituted phenyl group and a second imine group comprising a metal complexing group and a linking group linking the metal complexing group to second imine group nitrogen atom. In some iron or colbalt-α-diimine catalyst systems embodiments can comprise, or consist essentially of, a trialkylaluminum compound, an alkylaluminum halide (e.g., a dialkylaluminum halide, an alkylaluminum dihalide, and/or an alkylaluminum sesquihalide), an alkylaluminum alkoxide, an aluminoxane, or combinations thereof; or alternatively, comprises an alumoxane. In some embodiments, the iron or colbalt-α-diimine catalyst system can produce an ethylene oligomerization product having a K value ranging from 0.4 to 0.9; alternatively, from 0.4 to 0.8; alternatively, from 0.5 to 0.8; alternatively, from 0.5 to 0.7; alternatively, from 0.55 to 0.7. Additional information regarding the iron or colbalt-α-diimine catalyst system and the use of iron or colbalt-α-diimine catalyst systems for oligomerizing ethylene (including specific examples) can be found in, but not necessarily limited to, U.S. Pat. Nos. 7,129,304, 7,268,096, 7,271,121, 7,727,926, 7,728,160, 7,728,161, and 7,977,269.

Combinations of more than one catalyst systems described herein can be employed, if desired. Moreover, the processes disclosed herein are not limited solely to the catalyst systems provided hereinabove.

In embodiments, the catalyst system can be prepared by contacting the catalyst system with hydrogen. Alternatively, in other olefin oligomerization process, an olefin trimerization process, olefin tetramerization process, or olefin trimerization and tetramerization process embodiments, (e.g., ethylene oligomerization process, an ethylene trimerization process, ethylene tetramerization process, or an ethylene trimerization and tetramerization process embodiments), hydrogen can be added to the oligomerization reactor to accelerate the reaction and/or increase catalyst system activity. If desired, hydrogen also can be added to suppress polymer production. When hydrogen is utilized, the hydrogen partial pressure at which the ethylene oligomerization product, ethylene trimerization product, ethylene tetramerization product, or ethylene trimerization and tetramerization product can be formed can range from 2 psi to 100 psi; alternatively, 5 psi to 75 psi; alternatively, 10 psi to 50 psi.

Relating the reaction to oligomerization processes, trimerization processes, tetramerization processes, or trimerization and tetramerization processes described herein, the oligomerization, trimerization, tetramerization, or trimerization and tetramerization reaction zone can operate at any pressure that can facilitate the oligomerization, trimerization, tetramerization, or trimerization and tetramerization of an olefin. In an embodiment, the pressure at which the oligomerization processes, trimerization processes, tetramerization processes, or trimerization and tetramerization processes reactor can operate can be any pressure that produces the desired oligomerization product, trimerization product, tetramerization product, or trimerization and tetramerization product. In some embodiments, the ethylene oligomerization product, ethylene trimerization product, ethylene tetramerization product, or ethylene trimerization and tetramerization product can be formed at a pressure greater than or equal to 0 psig; alternatively, greater than or equal to 50 psig; alternatively, greater than or equal to 100 psig; alternatively, greater than or equal to 150 psig. In other embodiments, the ethylene oligomerization product, ethylene trimerization product, ethylene tetramerization product, or ethylene trimerization and tetramerization product can be formed at a pressure ranging from 0 psig to 2,500 psig; alternatively, 0 psig to 1,600 psig; alternatively, 0 psig to 1,500 psig; alternatively, 50 psig to 2,500 psig; alternatively, 100 psig to 2,500 psig; alternatively, 150 psig to 2,000 psig; alternatively, 300 psig to 900 psig. In embodiments wherein the monomer reactant is a gas (e.g., ethylene), the oligomerization product, trimerization product, tetramerization product, or trimerization and tetramerization product can be formed under a monomer gas pressure. When the oligomerization mixture, trimerization mixture, tetramerization mixture, or trimerization and tetramerization mixture produces an ethylene oligomerization product, ethylene trimerization product, ethylene tetramerization product, or ethylene trimerization and tetramerization product, the pressure can be the ethylene pressure or ethylene partial pressure. In some embodiments, the ethylene pressure (or ethylene partial pressure) at which the ethylene oligomerization product, ethylene trimerization product, ethylene tetramerization product, or ethylene trimerization and tetramerization product can be formed can be greater than or equal to 0 psig; alternatively, greater than or equal to 50 psig; alternatively, greater than or equal to 100 psig; alternatively, greater than or equal to 150 psig. In other embodiments, the ethylene pressure at which the ethylene oligomerization product, ethylene trimerization product, ethylene tetramerization product, or ethylene trimerization and tetramerization product can be formed can range from 0 psig to 2,500 psig; alternatively, 50 psig to 2,500 psig; alternatively, 100 psig to 2,500 psig; alternatively, 150 psig to 2,000 psig. In other embodiments, the ethylene pressure at which the ethylene oligomerization product, ethylene trimerization product, ethylene tetramerization product, or ethylene trimerization and tetramerization product can be formed can range from 500 psig to 5,000 psig, 1,000 psig to 5,000 psig, 2,000 psig to 5,000 psig, 3,000 psig to 5,000 psig, 500 psig to 4,000 psig, 1,000 psig to 4,000 psig, or 1000 psig to 3,500 psig.

In an embodiment, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be at least 0° C.; alternatively, at least 10° C.; alternatively, at least 20° C.; alternatively, at least 30° C.; alternatively, at least 40° C.; alternatively, at least 50° C.; alternatively, at least 60° C.; alternatively, at least 70° C.; alternatively, at least 80° C.; alternatively, at least 90° C.; alternatively, at least 100° C.; alternatively, at least 110° C.; alternatively, at least 120° C.; alternatively, at least 130° C.; alternatively, at least 140° C.; alternatively, at least 150° C.; alternatively, at least 160° C.; alternatively, at least 170° C.; alternatively, at least 180° C. In some embodiments, the maximum temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be 180° C.; alternatively, 160° C.; alternatively, 140° C.; alternatively, 120° C.; alternatively, 100° C.; alternatively, 90° C.; alternatively, 80° C. In some embodiments, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can range from any minimum temperature described herein to any maximum reaction temperature described herein as long as the maximum temperature is greater than the minimum temperature. In a non-limiting example, the temperature at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can range from 0° C. to 180° C.; alternatively, range from 10° C. to 160° C.; alternatively, range from 20° C. to 140° C.; alternatively, range from 30° C. to 120° C.; alternatively, range from 40° C. to 100° C.; alternatively, range from 50° C. to 100° C.; alternatively, range from 60° C. to 140° C. Other temperature ranges at which the olefin oligomerization product, olefin trimerization product, olefin tetramerization product, or olefin trimerization and tetramerization product (or alternatively, ethylene oligomerization product, ethylene trimerization product, ethylene tetramerization product, or ethylene trimerization and tetramerization product) can be formed can be understood by those skilled in the art with the aid of this disclosure.

The reaction time can comprise any time that can produce the desired quantity of olefin oligomerization product, olefin trimerization product, olefin tetramerization product, or olefin trimerization and tetramerization product (or alternatively, ethylene oligomerization product, ethylene oligomerization product, ethylene trimerization product, ethylene tetramerization product, or ethylene trimerization and tetramerization product) can be formed; alternatively, any time that can provide a desired catalyst system productivity; alternatively, any time that can provide a desired conversion of olefin (or alternatively, ethylene). For example, the olefin monomer (or alternatively, ethylene monomer) conversion can be at least 30 wt. % percent; alternatively, at least 35 wt. % percent; alternatively, at least 40 wt. % percent; alternatively, at least 45 wt. % percent.

In an embodiment, the ethylene trimerization product can comprise at least 70 wt. % hexene; alternatively, at least 75 wt. % hexene; alternatively, at least 80 wt. % hexene; alternatively, at least 85 wt. % hexene; or alternatively, at least 90 wt. % hexene based upon the weight of the oligomerization product. In some embodiments, the ethylene trimerization product can comprise from 70 wt. % to 99.8 wt. % hexene; alternatively, from 75 wt. % to 99.7 wt. % hexene; or alternatively, from 80 wt. % to 99.6 wt. % hexene based upon the weight of the ethylene trimerization product. In an embodiment, the ethylene tetramerization product can comprise at least 70 wt. % octene; alternatively, at least 75 wt. % octene; alternatively, at least 80 wt. % octene; alternatively, at least 85 wt. % octene; or alternatively, at least 90 wt. % octene based upon the weight of the ethylene tetramerization product. In some embodiments, the ethylene tetramerization product can comprise from 70 wt. % to 99.8 wt. % octene; alternatively, from 75 wt. % to 99.7 wt. % octene; or alternatively, from 80 wt. % to 99.6 wt. % octene based upon the weight of the ethylene tetramerization product. In other embodiments, the ethylene trimerization and tetramerization product can comprise at least 70 wt. % hexene and octene; alternatively, at least 75 wt. % hexene and octene; alternatively, at least 80 wt. % hexene and octene; alternatively, at least 85 wt. % hexene and octene; or alternatively, at least 90 wt. % hexene and octene based upon the weight of the ethylene trimerization and tetramerization product. In other embodiments, the ethylene trimerization and tetramerization product can comprise from 70 wt. % to 99.8 wt. % hexene and octene; alternatively, from 75 wt. % to 99.7 wt. % hexene and octene; or alternatively, from 80 wt. % to 99.6 wt. % hexene and octene based upon the weight of the ethylene trimerization and tetramerization product.

In ethylene oligomerization, ethylene trimerization, or ethylene trimerization and tetramerization embodiments, the ethylene trimer can comprise at least 85 wt. % 1-hexene; alternatively, at least 87.5 wt. % 1-hexene; alternatively, at least 90 wt. % 1-hexene; alternatively, at least 92.5 wt. % 1-hexene; alternatively, at least 95 wt. % 1-hexene; alternatively, at least 97 wt. % 1-hexene; or alternatively, at least 98 wt. % 1-hexene by weight of the ethylene trimer, or from 85 wt. % to 99.9 wt. % 1-hexene; alternatively, from 87.5 wt. % to 99.9 wt. % 1-hexene; alternatively, from 90 wt. % to 99.9 wt. % 1-hexene; alternatively, from 92.5 wt. % to 99.9 wt. % 1-hexene; alternatively, from 95 wt. % to 99.9 wt. % 1-hexene; alternatively, from 97 wt. % to 99.9 wt. % 1-hexene; or alternatively, from 98 wt. % to 99.9 wt. % 1-hexene by weight of the ethylene trimer.

In ethylene oligomerization, ethylene tetramerization, or ethylene trimerization and tetramerization embodiments, the ethylene tetramer can comprise at least 85 wt. % 1-octene; alternatively, at least 87.5 wt. % 1-octene; alternatively, at least 90 wt. % 1-octene; alternatively, at least 92.5 wt. % 1-octene; alternatively, at least 95 wt. % 1-octene; alternatively, at least 97 wt. % 1-octene; or alternatively at least 98 wt. % 1-octene by weight of the ethylene tetramer or from 85 wt. % to 99.9 wt. % 1-octene; alternatively, from 87.5 wt. % to 99.9 wt. % 1-octene; alternatively, from 90 wt. % to 99.9 wt. % 1-octene; alternatively, from 92.5 wt. % to 99.9 wt. % 1-octene; alternatively, from 95 wt. % to 99.9 wt. % 1-octene; alternatively, from 97 wt. % to 99.9 wt. % 1-octene; or alternatively, from 98 wt. % to 99.9 wt. % 1-octene by weight of the ethylene tetramer.

Figure 9:
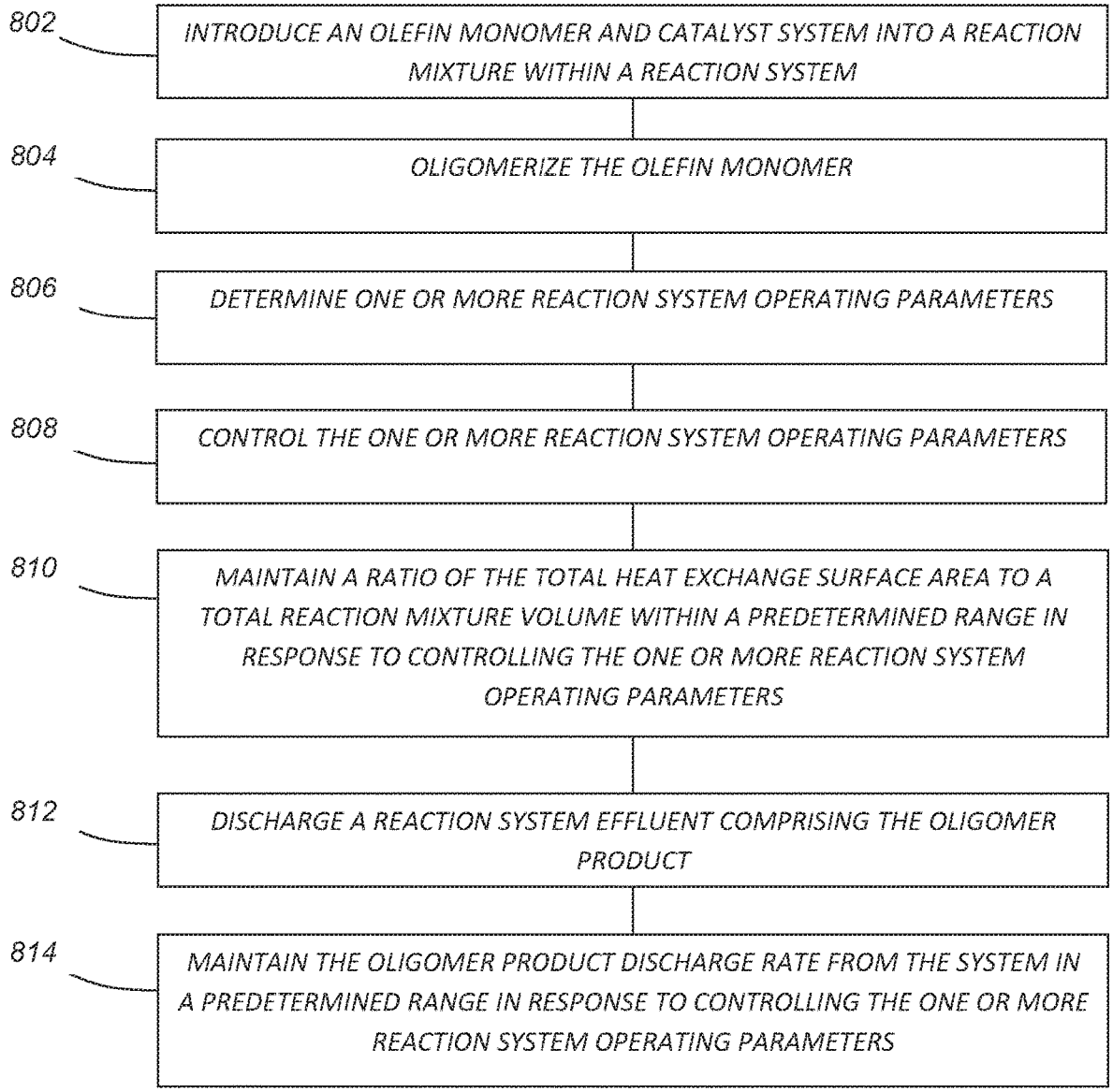
FIG. 9 illustrates a flow chart of an embodiment of a process for controlling the operating conditions within a reaction system.

FIG. 9 illustrates a flow chart of an embodiment of a process 800 for controlling the operating conditions within the reaction system. The process 800 can be carried out within a reactor, reactor system, reaction system, and/or reaction process, including any of the reactors, reactor system, reaction system, and/or reaction process configurations described herein. An olefin monomer can be periodically or continuously introduced, and a catalyst system or catalyst system components can also be periodically or continuously introduced into a reaction mixture within the reaction system in step 802. In some embodiments, a solvent can be, optionally, periodically or continuously introduced into the reaction mixture alone and/or with the introduction of any of the other reaction mixture components introduced into the reaction system. As described in more detail herein, the reaction system comprises a heat exchanged portion and a non-heat exchanged portion. The heat exchanged portion comprises a heat exchanged reaction mixture volume and a total heat exchanged surface area. The olefin monomer can be oligomerized, trimerized, tetramerized, or trimerized and tetramerized within the reaction mixture to form an oligomerization product, trimerization product, tetramerization product, or trimerization and tetramerization product in step 804. Within the reaction system, the oligomerization product, trimerization product, tetramerization product, or trimerization and tetramerization product can form a part of the reaction mixture comprising the olefin reactant, the catalyst, the oligomerization product (or trimerization product, tetramerization product, or trimerization and tetramerization product), and optionally, a diluent or solvent.

In step 806, one or more operating parameters can be determined within the oligomerization, trimerization, tetramerization, or trimerization and tetramerization reactor, reactor system, and/or reaction system using, for example, one or more sensors, gauges, meters, or the like. Various conditions within the oligomerization, trimerization, tetramerization, or trimerization and tetramerization reactor, reactor system, and/or reaction system can be measured or determined including, but not limited to, the inlet volumetric flowrate of one or more inlet streams, the outlet volumetric flowrate of one or more outlet or effluent streams, a temperature in the heat exchanged portion(s), a temperature in the non-heat exchanged portion(s), a temperature of a heat exchange medium within one or more heat exchanged portions, an oligomerization product, trimerization product, tetramerization product, or trimerization and tetramerization product concentration in the reaction mixture (e.g., at the outlet), one or more fluid flow characteristics of the reaction mixture in the heat exchanged portion(s), a flow rate of the reaction mixture in the heat exchanged portion, an operating parameter of an agitation device, a volumetric recycle rate of the reaction mixture in the reactor system and/or reaction system, one or more bulk fluid properties (e.g., the thermal conductivity, density, viscosity, specific heat, etc.) and any combination thereof. Additional variables that can affect the operation of the oligomerization, trimerization, tetramerization, or trimerization and tetramerization reactor, reactor system, and/or reaction system can be measured or determined such as a heat exchanged surface area, a non-heat exchanged surface area, a catalyst reactivity, reaction mixture properties and concentrations, a total reaction mixture volume, a total heat exchanged reaction mixture volume, a non-heat exchanged reaction mixture volume, and/or any combination thereof. The conditions can be directly or indirectly measured. For an indirect measurement of a condition, one or more measurements can be obtained, and a desired condition can be determined using the measurements in correlations, calculations, and the like to determine the desired condition. In addition, measurements of the fluid properties at the inlet and/or exit of the oligomerization, trimerization, tetramerization, or trimerization and tetramerization reactor, reactor system, and/or reaction system, with or without any direct internal measurements, can be used to determine one or more conditions within the oligomerization, trimerization, tetramerization, or trimerization and tetramerization reactor, reactor system, and/or reaction system.

In step 808, the one or more reaction system operating parameters can be controlled during the oligomerization reaction. Control of the operating parameters can include direct control over one of the parameters and/or indirect control through the manipulation of one or more inputs to the reaction system that affect the parameter or parameters being controlled.

In step 810, a ratio of the total heat exchanged surface area to a total reaction mixture volume within the reactor, reactor system and/or reaction system can be within a range from 0.75 in$^{-1}$ to 5 in$^{-1}$ in response to controlling the one or more reactor, reactor system, and/or reaction system operating parameters. In an embodiment, the one or more reactor, reactor system, and/or reaction system operating parameters can include an inlet volumetric flowrate and a volumetric flowrate of the reaction system effluent. The ratio of the total heat exchanged surface area to the total reaction mixture volume within the reactor, reactor system, and/or reaction system can then be maintained within the desired range by controlling the inlet volumetric flowrate and the volumetric flowrate of the reactor, reactor system, and/or reaction system effluent. For example, when the reaction system is not completely filled with a reaction mixture, the total reaction mixture volume can be less than the total volume of the reaction system. By controlling the total reaction mixture volume within the reaction system, the ratio of the total heat exchanged surface area to a total reaction mixture volume within the reaction system can be controlled.

In an embodiment, the one or more reactor, reactor system, and/or reaction system operating parameters can include the heat exchanged surface area. During operation, one or more heat exchange surface areas can be selectively used, activated, and/or deactivated. For example, a heat exchange jacket, an internal heat exchange coil, one or more heat exchange surfaces in a heat exchanger in a loop, and the like can be used to provide heat exchange with the reaction mixture. During operation, the total heat exchanged surface area can be varied by selectively performing heat exchange in one or more of the heat exchange devices. For example, ceasing the use of a heat exchange surface in the internal heat exchange coil (e.g., by ceasing the heat exchange medium flow to the internal heat exchange coil, etc.) would reduce the total heat exchanged surface area. The ratio of the total heat exchanged surface area to the total reaction mixture volume within the reaction system can then be maintained within the desired range by controlling the total heat exchanged surface area performing an active heat exchange.

Other conditions within the reactor, reactor system, and/or reaction system can also be controlled to maintain the desired operating conditions. In step 812, the reaction system effluent can be periodically or continuously discharged from the system. The reaction system effluent can comprise the oligomerization product, trimerization product, tetramerization product, or trimerization and tetramerization product. The one or more operating parameters can be controlled to maintain the oligomerization product, trimerization product, tetramerization product, or trimerization and tetramerization product discharge rate from the reaction system between 1.0 (lb)(hr$^{-1}$)(gal$^{-1}$) and 6.0 (lb)(hr$^{-1}$)(gal$^{-1}$) in response to controlling the one or more reaction system operating parameters in step 814. In an embodiment, the one or more reaction system operating parameters can comprise an oligomerization product, trimerization product, tetramerization product, or trimerization and tetramerization product concentration in the reaction mixture, the inlet volumetric flowrate and the volumetric flowrate of the reaction system effluent, and/or the monomer conversion within the reaction system, where the oligomerization product, trimerization product, tetramerization product, or trimerization and tetramerization product discharge rate can be maintained in the desired range in response to controlling the oligomerization product, trimerization product, tetramerization product, or trimerization and tetramerization product concentration.

In an embodiment, the average temperature of the reaction mixture within the non-heat exchanged portion of the reaction system can be maintained within a threshold amount of the average temperature of the reaction mixture within the heat exchanged portion of the reaction system. The average temperature of the reaction mixture within the non-heat exchanged portion the reaction system can be measured as well as the average temperature of the reaction mixture within the heat exchanged portion of the reaction system. The average temperatures can then be controlled by controlling the average temperature of a heat exchange medium in the heat exchanged portions. By adjusting the average temperature of the heat exchange medium (e.g., by adjusting the temperature and/or flowrate of the heat exchange medium through the heat exchanged portion(s)), the average temperatures within the heat exchanged portion of the reaction system and the non-heat exchanged portion of the reaction system can be controlled to within the threshold amount. In an embodiment, the threshold temperature difference between the average temperature of the reaction mixture within the non-heat exchanged portion(s) of the reaction system and the average temperature of the reaction mixture within the heat exchanged portion of the reactor system can be maintained within 0.61%, within 0.53%, within 0.46%, within 0.38%, within 0.31%, within 0.27%, within 0.24%, or within 0.21%, where the percentage values refer to a comparison of the temperatures on an absolute temperature scale (i.e., K or ° R).

In an embodiment, the average temperature of the heat exchanged medium can be maintained within a threshold amount of the average temperature of the reaction mixture within the heat exchanged portion of the reaction system. As noted above, the average temperatures can then be controlled by controlling the average temperature of a heat exchange medium in the heat exchanged portions of the reaction system. By adjusting the average temperature of the heat exchange medium (e.g., by adjusting the temperature and/or flowrate of the heat exchange medium through the heat exchanged portion(s) of the reaction system), the average temperatures can be controlled to within the threshold amount. In an embodiment, the threshold temperature difference between the average temperature of the heat exchanged medium and the average temperature of the reaction mixture within the heat exchanged portion of the reactor system can be maintained within 9.3%, within 7.6%, within 6.1%, within 5.3%, or within 4.6% of the average temperature of the reaction mixture in the heat exchanged section(s) of the reaction system. The percentage values refer to a comparison of the temperatures on an absolute temperature scale (i.e., K or ° R).

In an embodiment, operating parameter(s) can include the flow characteristics of the reaction mixture within the heat exchanged portion(s) of the reaction system. The operating parameters can be controlled to maintain a turbulent flow of the reaction mixture through the heat exchanged portion of the reaction system. For example, an input to a mixing or stirring device can be controlled, the pumping and flow characteristics of the reaction mixture can be controlled, the input/output rates from the reaction system can be controlled, or the like in order to maintain a turbulent flow of the reaction mixture through the heat exchanged portion(s) of the reaction system. In an embodiment, the Reynolds number of the reaction mixture within the heat exchanged portion(s) of the reaction system can be maintained between $2 \times 10^5$ to $1 \times 10^6$, or any other Reynolds number or Reynolds number range disclosed herein, based on controlling the one or more reaction system operating parameters.

When the reaction system comprises a recycle loop, the one or more operating parameters can include the relative volumetric flowrates of the input(s), effluent output(s), and/or the flow through the recycle loop(s). Various control equipment such as control valves, pump rates, and the like can be used to control the relative volumetric flowrates of the process streams. In an embodiment, the relative volumetric flowrates can be controlled to maintain a ratio of a volumetric reaction mixture recycle flow rate of the portion of the reaction mixture recycled within the recycle loop and/or the reaction system to the volumetric discharge rate of the recycle loop and/or the reaction system effluent between 8 and 60, or any other ratio or range of ratios of the volumetric reaction mixture recycle flow rate of the portion of the reaction mixture recycled within the recycle loop and/or the reaction system to the volumetric discharge rate of the recycle loop and/or the reaction system effluent disclosed herein.

Figure 10:
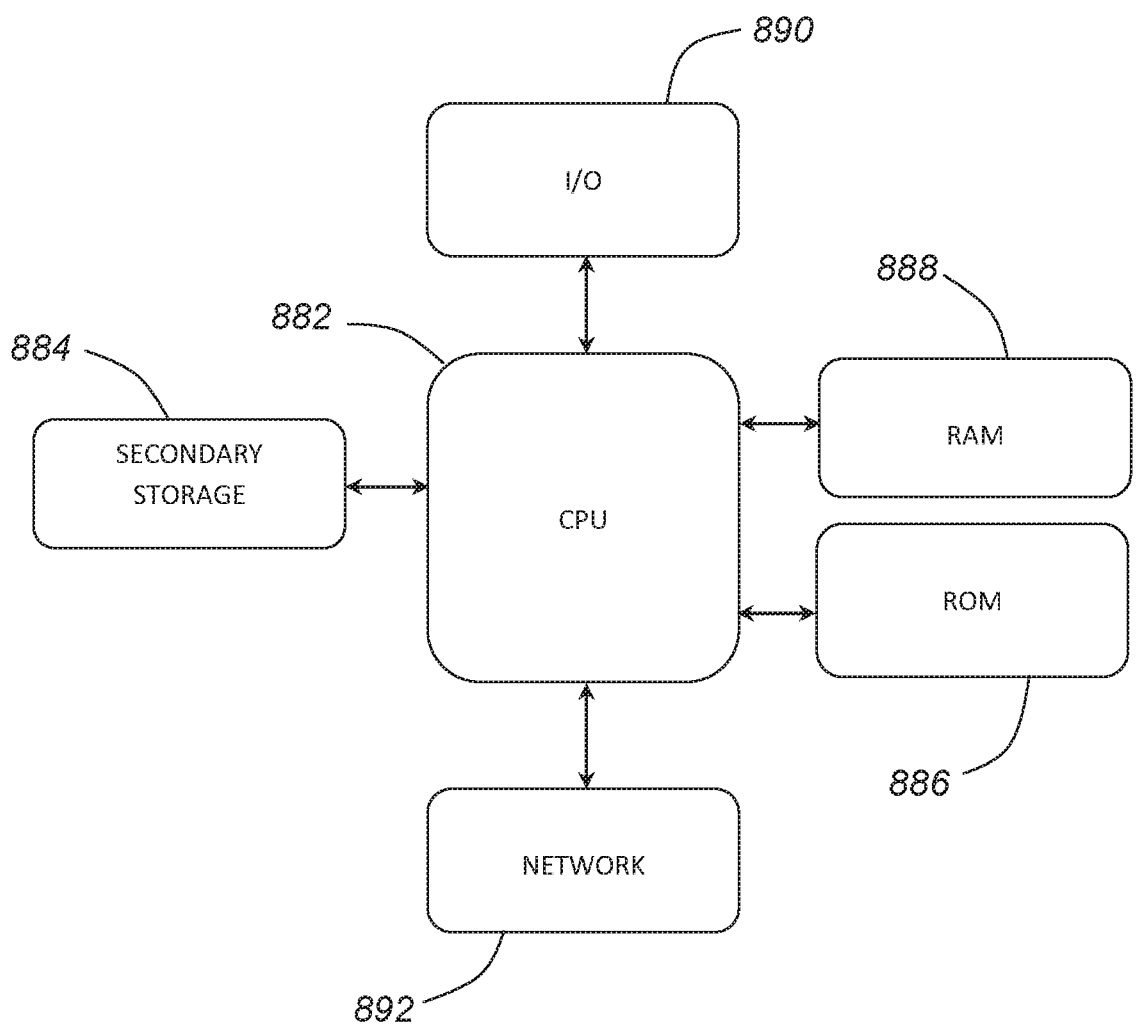
FIG. 10 illustrates an embodiment of a computer system.

In some embodiments, the oligomerization process, trimerization process, tetramerization process, termerization and tetramerization process can be controlled using an automated control system. The control system can operate using one or more processors and receive and/or relay signals to and from sensors, detectors, control equipment (e.g., valves, pumps, etc.) during use. FIG. 10 illustrates a computer system 880 suitable for implementing one or more embodiments of the reaction system and/or control system disclosed herein. In an embodiment, the computer system 880 can be used to store and/or execute one or more control programs used with the oligomerization, trimerization, tetramerization, or trimerization and tetramerization reactor, reactor system, and/or reaction system and/or the oligomerization, trimerization, tetramerization, or trimerization and tetramerization reactor, reactor system, or reaction system control module. The computer system 880 includes a processor 882 (which can be referred to as a central processor unit or CPU) that is in communication with memory devices including secondary storage 884, read only memory (ROM) 886, random access memory (RAM) 888, input/output (I/O) devices 890, and network connectivity devices 892. The processor 882 can be implemented as one or more CPU chips.

It is understood that by programming and/or loading executable instructions onto the computer system 880, at least one of the CPU 882, the RAM 888, and the ROM 886 are changed, transforming the computer system 880 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change can be preferred to be implemented in software, because re-spinning a hardware implementation can be more expensive than re-spinning a software design. Generally, a design that is stable that will be produced in large volume can be preferred to be implemented in hardware, for example in an application specific integrated circuit (ASIC), because for large production runs the hardware implementation can be less expensive than the software implementation. Often a design can be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions can be viewed as a particular machine or apparatus.

The secondary storage 884 can be comprised of one or more disk drives or tape drives and can be used for non-volatile storage of data and as an over-flow data storage device if RAM 888 is not large enough to hold all working data. Secondary storage 884 can be used to store programs which are loaded into RAM 888 when such programs are selected for execution. The ROM 886 can be used to store instructions and perhaps data which can be read during program execution. ROM 886 can be a non-volatile memory device which typically has a small memory capacity relative to the larger memory capacity of secondary storage 884. The RAM 888 can be used to store volatile data and perhaps to store instructions. Access to both ROM 886 and RAM 888 can be typically faster than to secondary storage 884. The secondary storage 884, the RAM 888, and/or the ROM 886 can be referred to in some contexts as computer readable storage media and/or non-transitory computer readable media.

I/O devices 890 can include printers, video monitors, liquid crystal displays (LCDs), touch screen displays, keyboards, keypads, switches, dials, mice, track balls, voice recognizers, card readers, paper tape readers, or other well-known input devices.

The network connectivity devices 892 can take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 892 can enable the processor 882 to communicate with the Internet or one or more intranets. With such a network connection, it is contemplated that the processor 882 might receive information from the network, or might output information to the network in the course of performing the above-described method steps. Such information, which can be represented as a sequence of instructions to be executed using processor 882, can be received from and outputted to the network, for example, in the form of a computer data signal embodied in a carrier wave.

Such information, which can include data or instructions to be executed using processor 882 for example, can be received from and outputted to the network, for example, in the form of a computer data baseband signal or signal embodied in a carrier wave. The baseband signal or signal embodied in the carrier wave, or other types of signals currently used or hereafter developed, can be generated according to several methods well known to one skilled in the art. The baseband signal and/or signal embodied in the carrier wave can be referred to in some contexts as a transitory signal.

The processor 882 can execute instructions, codes, computer programs, scripts which it accesses from hard disk, floppy disk, optical disk (these various disk based systems can all be considered secondary storage 884), ROM 886, RAM 888, or the network connectivity devices 892. While only one processor 882 is shown, multiple processors can be present. Thus, while instructions can be discussed as executed by a processor, the instructions can be executed simultaneously, serially, or otherwise executed by one or multiple processors. Instructions, codes, computer programs, scripts, and/or data that can be accessed from the secondary storage 884, for example, hard drives, floppy disks, optical disks, and/or other device, the ROM 886, and/or the RAM 888 can be referred to in some contexts as non-transitory instructions and/or non-transitory information.

In an embodiment, the computer system 880 can comprise two or more computers in communication with each other that collaborate to perform a task. For example, but not by way of limitation, an application can be partitioned in such a way as to permit concurrent and/or parallel processing of the instructions of the application. Alternatively, the data processed by the application can be partitioned in such a way as to permit concurrent and/or parallel processing of different portions of a data set by the two or more computers. In an embodiment, virtualization software can be employed by the computer system 880 to provide the functionality of a number of servers that is not directly bound to the number of computers in the computer system 880. For example, virtualization software can provide twenty virtual servers on four physical computers. In an embodiment, the functionality disclosed above can be provided by executing the application and/or applications in a cloud computing environment. Cloud computing can comprise providing computing services via a network connection using dynamically scalable computing resources. Cloud computing can be supported, at least in part, by virtualization software. A cloud computing environment can be established by an enterprise and/or can be hired on an as-needed basis from a third party provider. Some cloud computing environments can comprise cloud computing resources owned and operated by the enterprise as well as cloud computing resources hired and/or leased from a third party provider.

In an embodiment, some or all of the functionality disclosed above can be provided as a computer program product. The computer program product can comprise one or more computer readable storage medium having computer usable program code embodied therein to implement the functionality disclosed above. The computer program product can comprise data structures, executable instructions, and other computer usable program code. The computer program product can be embodied in removable computer storage media and/or non-removable computer storage media. The removable computer readable storage medium can comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product can be suitable for loading, by the computer system 880, at least portions of the contents of the computer program product to the secondary storage 884, to the ROM 886, to the RAM 888, and/or to other non-volatile memory and volatile memory of the computer system 880. The processor 882 can process the executable instructions and/or data structures in part by directly accessing the computer program product, for example by reading from a CD-ROM disk inserted into a disk drive peripheral of the computer system 880. Alternatively, the processor 882 can process the executable instructions and/or data structures by remotely accessing the computer program product, for example by downloading the executable instructions and/or data structures from a remote server through the network connectivity devices 892. The computer program product can comprise instructions that promote the loading and/or copying of data, data structures, files, and/or executable instructions to the secondary storage 884, to the ROM 886, to the RAM 888, and/or to other non-volatile memory and volatile memory of the computer system 880.

In some contexts, the secondary storage 884, the ROM 886, and the RAM 888 can be referred to as a non-transitory computer readable medium or a computer readable storage media. A dynamic RAM embodiment of the RAM 888, likewise, can be referred to as a non-transitory computer readable medium in that while the dynamic RAM receives electrical power and is operated in accordance with its design, for example during a period of time during which the computer system 880 is turned on and operational, the dynamic RAM stores information that is written to it. Similarly, the processor 882 can comprise an internal RAM, an internal ROM, a cache memory, and/or other internal non-transitory storage blocks, sections, or components that can be referred to in some contexts as non-transitory computer readable media or computer readable storage media.

Having described the various systems and methods, embodiments of the systems and methods can include, but are not limited to:

In a first embodiment, a process comprises periodically or continuously introducing an olefin monomer and periodically or continuously introducing a catalyst system or catalyst system components into a reaction mixture within a reaction system; oligomerizing the olefin monomer within the reaction mixture to form an oligomer product; and periodically or continuously discharging a reaction system effluent comprising the oligomer product from the reaction system, wherein the reaction system comprises: a total reaction mixture volume within the reaction system; and a heat exchanged portion of the reaction system comprising a heat exchanged reaction mixture volume and a total heat exchanged surface area providing indirect thermal contact between the reaction mixture and a heat exchange medium; wherein a ratio of the total heat exchanged surface area to the total reaction mixture volume within the reaction system is in a range from 0.75 in$^{-1}$ to 5 in$^{-1}$; and wherein an oligomer product discharge rate from the reaction system is between 1.0 (lb)(hr$^{-1}$)(gal$^{-1}$) to 6.0 (lb)(hr$^{-1}$)(gal$^{-1}$).

A second embodiment can include the process of the first embodiment, further comprising: periodically or continuously introducing a reaction solvent into the reaction mixture within the reaction system.

A third embodiment can include the process of the first or second embodiment, wherein the reaction system further comprises: one or more reaction system inlets configured to periodically or continuously introduce: a) the olefin monomer, b) the catalyst system or catalyst system components, c) the optional reaction system solvent, or d) any combination thereof into the reaction mixture within the reaction system; and one or more reaction system outlets configured to periodically or continuously discharge the reaction system effluent comprising the oligomer product from the reaction system.

In a fourth embodiment, a reaction system comprises: one or more reaction system inlets configured to periodically or continuously introduce an olefin monomer, a catalyst system or catalyst system components, or any combination thereof to a reaction mixture within the reaction system; one or more reaction system reaction mixture outlets configured to periodically or continuously discharge a reaction system effluent comprising an oligomer product from the reaction system; a total reaction mixture volume within the reaction system; a heat exchanged portion of the reaction system comprising a heat exchanged reaction mixture volume, and a total heat exchanged surface area providing indirect thermal contact between the reaction mixture and a heat exchange medium; wherein a ratio of the total heat exchanged surface area to the total reaction mixture volume within the reaction system is in a range from 0.75 in$^{-1}$ to 5 in$^{-1}$, and wherein an oligomer product discharge rate from the reaction system is between 1.0 (lb)(hr$^-$)(gal$^{-1}$) to 6.0 (lb)(hr$^{-1}$)(gal$^{-1}$).

A fifth embodiment can include the reaction system of the fourth embodiment, wherein the one or more reaction system inlets are further configured to periodically or continuously introduce a reaction solvent to a reaction mixture within the reaction system.

A sixth embodiment can include the process or reaction system of any of the first to fifth embodiments, wherein a ratio of the heat exchanged reaction mixture volume to the total reaction mixture volume within the reaction system is in a range from 0.70 to 1.0.

A seventh embodiment can include the process or reaction system of any of the first to sixth embodiments, wherein the reaction system further comprises a non-heat exchanged portion of the reaction system comprising a non-heat exchanged reaction mixture volume and a total non-heat exchanged surface area that does not providing heat exchange between the reaction mixture and the heat exchange medium.

An eighth embodiment can include the process or reaction system of the seventh embodiment, wherein an average temperature of the reaction mixture within the non-heat exchanged portion the reaction system is within 0.61% of an average temperature of the reaction mixture within the heat exchanged portion of the reaction system.

A ninth embodiment can include the process or reaction system of the seventh or eighth embodiment, wherein an average temperature of the heat exchange medium is within 9.3% of the average temperature of the reaction mixture within the heat exchanged portion of the reaction system.

In a tenth embodiment, a process comprises periodically or continuously introducing an olefin monomer and periodically or continuously introducing a catalyst system into a reaction mixture within a reaction system, wherein the reaction system comprises a heat exchanged portion and a non-heat exchanged portion, and wherein the heat exchanged portion comprises a heat exchanged reaction mixture volume and a total heat exchanged surface area providing indirect thermal contact between the reaction mixture and a heat exchange medium; oligomerizing the olefin monomer within the reaction mixture to form an oligomer product; and determining one or more reaction system operating parameters during the oligomerizing; controlling the one or more reaction system operating parameters during the oligomerizing; maintaining a ratio of the total heat exchanged surface area to a total reaction mixture volume within the reaction system in a range from 0.75 in$^{-1}$ to 5 in$^{-1}$ in response to controlling the one or more reaction system operating parameters; periodically or continuously discharging a reaction system effluent comprising the oligomer product from the reaction system; and maintaining an oligomer product discharge rate from the reaction system between 1.0 (lb)(hr$^{-1}$)(gal$^{-1}$) and 6.0 (lb)(hr$^{-1}$)(gal$^{-1}$) in response to controlling the one or more reaction system operating parameters.

In an eleventh embodiment, a process comprises periodically or continuously introducing an olefin monomer and periodically or continuously introducing a catalyst system or catalyst system components into a reaction mixture within a reaction system, wherein the reaction system comprises: a total reaction mixture volume within the reaction system; and a heat exchanged portion of the reaction system comprising a heat exchanged reaction mixture volume and a total heat exchanged surface area providing indirect thermal contact between the reaction mixture and a heat exchange medium; oligomerizing the olefin monomer within the reaction mixture to form an oligomer product; determining one or more reaction system operating parameters during the oligomerizing; controlling the one or more reaction system operating parameters during the oligomerizing; maintaining a ratio of the heat exchanged reaction mixture volume to the total reaction mixture volume within the reaction system is in a range from 0.7 to 1 in response to controlling the one or more reaction system operating parameters; maintaining a Reynolds number of the reaction mixture passing through the heat exchanged portion of the reaction system at greater than 2×10$^5$ in response to controlling the one or more reaction system operating parameters; and periodically or continuously discharging a reaction system effluent comprising the oligomer product from the reaction system.

In a twelfth embodiment, a process comprises periodically or continuously introducing an olefin monomer and periodically or continuously introducing a catalyst system or catalyst system components into a reaction mixture within a reaction system, wherein the reaction system comprises: a total reaction mixture volume within the reaction system; and a heat exchanged portion of the reaction system comprising a heat exchanged reaction mixture volume and a total heat exchanged surface area providing indirect thermal contact between the reaction mixture and a heat exchange medium; oligomerizing the olefin monomer within the reaction mixture to form an oligomer product; determining one or more reaction system operating parameters during the oligomerizing; controlling the one or more reaction system operating parameters during the oligomerizing; maintaining a ratio of the total heat exchanged surface area to a total reaction mixture volume within the reaction system in a range from 0.75 in$^{-1}$ to 5 in$^{-1}$ in response to controlling the one or more reaction system operating parameters; and periodically or continuously discharging a reaction system effluent comprising the oligomer product from the reaction system.

A thirteenth embodiment can include the process of any of the tenth to twelfth embodiments, wherein the one or more reaction system operating parameters comprise an inlet volumetric flowrate and a volumetric flowrate of the reaction system effluent, and wherein maintaining the ratio of the total heat exchanged surface area to the total reaction mixture volume within the reaction system is in response to controlling the inlet volumetric flowrate and the volumetric flowrate of the reaction system effluent.

A fourteenth embodiment can include the process of any of the tenth to thirteenth embodiments, wherein the one or more reaction system operating parameters comprise an oligomer product concentration in the reaction mixture, and wherein maintaining the oligomer product discharge rate is in response to controlling the oligomer product concentration.

A fifteenth embodiment can include the process of any of the eleventh to sixteenth embodiments, further comprising: maintaining an average temperature of the reaction mixture within the non-heat exchanged portion the reaction system within 2% of an average temperature of the reaction mixture within the heat exchanged portion of the reaction system based on controlling the one or more reaction system operating parameters.

A sixteenth embodiment can include the process of the fifteenth embodiment, wherein the one or more reaction system operating parameters comprise the average temperature of the reaction mixture within the non-heat exchanged portion the reaction system, the average temperature of the reaction mixture within the heat exchanged portion of the reaction system, and an average temperature of a heat exchange medium, and wherein controlling the one or more reaction system operating parameters comprises controlling at least the average temperature of the heat exchange medium.

A seventeenth embodiment can include the process of the fifteenth or sixteenth embodiment, further comprising maintaining the average temperature of the heat exchange medium within 30% of the average temperature of the reaction mixture within the heat exchanged portion of the reaction system.

An eighteenth embodiment can include the process of any of the tenth to seventeenth embodiments, further comprising: maintaining a Reynolds number of the reaction mixture within the heat exchanged portion of the reaction system between 2×10$^5$ to 1×10$^6$ based on controlling the one or more reaction system operating parameters.

A nineteenth embodiment can include the process of the eighteenth embodiment, wherein the one or more reaction system operating parameters comprise a flow rate of the reaction mixture in the heat exchanged portion, an operating parameter of an agitation device, or any combination thereof.

A twentieth embodiment can include the process or reaction system of any of the first to fifth embodiments, wherein a ratio of the total reaction system heat exchanged surface area to the total reaction mixture volume within the reaction system is in a range from a minimum value described by the equation [0.64*(oligomer product discharge rate from the reaction system)−1.16 to a maximum value described by the equation [0.64*(oligomer product discharge rate from the reaction system)]+0.76.

A twenty first embodiment can include the process or reaction system of any of the first to twentieth embodiments, wherein the reaction system comprises a reactor selected from the group consisting of a continuous stirred tank reactor (CSTR), a plug flow reactor, or any combinations thereof.

A twenty second embodiment can include the process or reaction system of the twenty first embodiment, wherein the reaction system comprises a continuous stirred tank reactor, and wherein the heat exchange medium is in indirect contact with the reaction mixture within a jacket around at least a portion of the outer wall of the continuous stirred tank reactor, within internal heat exchange coils, or any combination thereof.

A twenty third embodiment can include the process or reaction system of the twenty first embodiment, wherein the heat exchange medium has indirect contact with the reaction mixture through a wall of at least a portion of the reactor.

A twenty fourth embodiment can include the process or reaction system of any of the first to twenty third embodiments, wherein the reaction mixture passes through the heat exchanged portion of the reaction system in a turbulent flow regime.

A twenty fifth embodiment can include the process or reaction system of the twenty fourth embodiment, wherein the reaction system comprises a continuous stirred tank reactor (CSTR) and the turbulent flow regime is maintained in the continuous stirred tank reactor (CSTR) using a mechanical stirrer, baffles, gas sparging, or any combination thereof.

A twenty sixth embodiment can include the process or reaction system of the twenty fourth embodiment, wherein the reaction system comprises one or more plug flow reactors, and wherein the reaction mixture passes through the heat exchanged portion of the plug flow reactors with a Reynolds number of greater than $2\times10^5$.

A twenty seventh embodiment can include the process or reaction system of the twenty fourth embodiment, wherein the reaction system comprises one or more plug flow reactor, and wherein the reaction mixture passes through the heat exchanged portion of the plug flow reactors with a Reynolds number from $2\times10^5$ to $1\times10^6$.

A twenty eighth embodiment can include the process or reaction system of any of the twenty first to twenty seventh embodiments, wherein the reaction system comprises a reaction mixture path, and wherein the reaction mixture is recycled through the reactor.

A twenty ninth embodiment can include the process or reaction system of the twenty eighth embodiment, wherein the reaction mixture path includes a pump.

A thirtieth embodiment can include the process or reaction system of the twenty eight or twenty ninth embodiment, wherein a ratio of a volumetric reaction mixture recycle flow rate to a volumetric discharge rate of the reaction system effluent is between 8 and 60.

A thirty first embodiment can include the process or reaction system of any of the first to thirtieth embodiments, wherein the olefin monomer consists essentially of ethylene.

A thirty second embodiment can include the process or reaction system of the thirty first embodiment, wherein the catalyst system comprises chromium, a heteroatomic ligand, and a metal alkyl compound.

A thirty third embodiment can include the process or reaction system of the thirty second embodiment, wherein the heteroatomic ligand is selected from pyrrole compounds, diphosphinoaminyl compounds, $N^2$-phosphinylamidine compounds, $N^2$-phosphinylformamidine compounds, phosphinyl guanidine compounds, and combinations thereof.

A thirty fourth embodiment can include the process or reaction system of the thirty first embodiment, wherein the reaction mixture comprises a catalyst system, and wherein the catalyst system is selected from a group consisting of: a) a chromium compound, a pyrrole compound, a metal alkyl compound; b) a chromium compound, a diphosphinoaminyl compound, and a metal alkyl compound; c) a chromium complex of a diphosphinoaminyl compound, and a metal alkyl compound; d) a chromium compound, an $N^2$-phosphinylamidine compound, and a metal alkyl compound; e) a chromium complex of an $N^2$-phosphinylamidine compound, and a metal alkyl compound; f) a chromium compound, an $N^2$-phosphinylformamidine compound, and a metal alkyl compound; g) a chromium complex of an $N^2$-phosphinylformamidine compound, and a metal alkyl compound; h) a chromium compound, an $N^2$-phosphinyl guanidine compound, and a metal alkyl compound; i) a chromium complex of an $N^2$-phosphinyl guanidine compound, and a metal alkyl compound; and j) any combination thereof.

A thirty fifth embodiment can include the process or reaction system of the thirty first embodiment, wherein the reaction mixture comprises the catalyst system, and wherein the catalyst system comprises a chromium compound, a pyrrole compound, a metal alkyl compound, and a halide compound.

A thirty sixth embodiment can include the process or reaction system of the thirty fourth embodiment, wherein the metal alkyl compound is selected from alkylaluminum compounds, aluminoxanes, and combinations thereof.

A thirty seventh embodiment can include the process or reaction system of any of the thirty second to thirty sixth embodiments, wherein the oligomer product comprises hexenes, octenes, or any combination thereof.

A thirty eighth embodiment can include the process or reaction system of the thirty first embodiment, wherein the catalyst system comprises a trialkylaluminum compound.

A thirty ninth embodiment can include the process or reaction system of the thirty eighth embodiment, wherein the catalyst system consists essentially of triethylaluminum, tri-n-butylaluminum, or any combination of triethylaluminum and tri-n-butylaluminum.

A fortieth embodiment can include the process or reaction system of the thirty first embodiment, wherein the reaction mixture comprises the catalyst system, and wherein the catalyst system comprises a) a nickel salt and an organophosphorus compound or b) a nickel complex of an organophosphorus compound.

A forty first embodiment can include the process or reaction system of the thirty first embodiment, wherein the reaction mixture comprises the catalyst system, and wherein the catalyst system comprises, a) a zirconium halide, and an metal compound, or b) a zirconium halide, alkoxide, or carboxylate, a Lewis base, and an alkylaluminum compound.

A forty second embodiment can include the process or reaction system of the thirty first embodiment, wherein the reaction mixture comprises the catalyst system, and wherein the catalyst system comprises: a) a transition metal complex comprising a transition metal compound complexed to a ligand comprising an α-diimine group and a metal alkyl compound, b) a transition metal complex comprising a transition metal compound complexed to a ligand comprising a pyridine bisimine group and a metal alkyl compound, c) a transition metal compound, a ligand comprising a pyridine bisimine group, and a metal alkyl compound, or d) any combination thereof.

A forty third embodiment can include the process or reaction system of the forty second embodiment, wherein the transition metal of the transition metal compound or the transition metal compound of the transition metal complex is Fe or Co.

A forty fourth embodiment can include the process or reaction system of the forty second embodiment, wherein the transition metal compound or the transition metal compound of the transition metal complex is a Fe(II) or Fe(III) halide or a Co(II) or Co(III) halide.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

The invention illustratively disclosed herein suitably can be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Therefore, the present invention is well adapted to attain the ends and advantages mentioned as well as those that are inherent therein. This concludes the detailed description. The particular embodiments disclosed above are illustrative only, as the invention can be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above can be altered or modified and all such variations are considered within the scope and spirit of the invention. Accordingly, the protection sought herein is as set forth in the claims below.

I claim:

1. A process comprising:
   periodically or continuously introducing an olefin monomer and periodically or continuously introducing a catalyst system or catalyst system components into a reaction mixture within a reaction system;
   oligomerizing the olefin monomer within the reaction mixture to form an oligomer product; and
   periodically or continuously discharging a reaction system effluent comprising the oligomer product from the reaction system;
   wherein the reaction system comprises: a total reaction mixture volume within the reaction system; and a heat exchanged portion of the reaction system comprising a heat exchanged reaction mixture volume and a total heat exchanged surface area providing indirect thermal contact between the reaction mixture and a heat exchange medium;
   wherein the process is operated at an oligomer product discharge rate from the reaction system between 1.5 $(lb)(hr^{-1})(gal^{-1})$ to 6.0 $(lb)(hr^{-1})(gal^{-1})$; and
   wherein the process is operated at a ratio of the total heat exchanged surface area to the total reaction mixture volume within the reaction system in a range from 0.75 $in^{-1}$ to 5 $in^{-1}$.

2. The process of claim 1, wherein the reaction system further comprises a non-heat exchanged portion of the reaction system comprising a non-heat exchanged reaction mixture volume and a total non-heat exchanged surface area that does not provide heat exchange between the reaction mixture and the heat exchange medium, and wherein an average temperature of the heat exchange medium is within 6.1% of an average temperature of the reaction mixture within the heat exchanged portion of the reaction system.

3. The process of claim 1, wherein the reaction system further comprises a non-heat exchanged portion of the reaction system comprising a non-heat exchanged reaction mixture volume and a total non-heat exchanged surface area that does not provide heat exchange between the reaction mixture and the heat exchange medium, and wherein an average temperature of the reaction mixture within the non-heat exchanged portion the reaction system is within 0.61% of an average temperature of the reaction mixture within the heat exchanged portion of the reaction system.

4. The process of claim 1, wherein a ratio of the heat exchanged reaction mixture volume to the total reaction mixture volume within the reaction system is in a range from 0.70 to 1.0.

5. The process of claim 1, further comprising: periodically or continuously introducing a reaction solvent into the reaction mixture within the reaction system.

6. The process of claim 1, wherein the reaction system comprises a reactor selected from the group consisting of a continuous stirred tank reactor, a plug flow reactor, and any combination thereof.

7. The process of claim 6, wherein the reaction system comprises
   a) a continuous stirred tank reactor wherein the heat exchange medium is in indirect contact with the reaction mixture within a jacket around at least a portion of an outer wall of the continuous stirred tank reactor, within internal heat exchange coils, or any combination thereof;
   b) one or more plug flow reactors wherein the heat exchange medium is in indirect contact with the reaction mixture through a wall of at least a portion of the one or more one plug flow reactors; or
   c) comprises a reaction mixture path comprising the reactor and wherein a portion of the reaction mixture is recycled through the reactor and a ratio of a volumetric reaction mixture recycle flow rate to a volumetric discharge rate of the reaction system effluent is between 8 and 60.

8. The process of claim 1, wherein the olefin monomer consists essentially of ethylene and the catalyst system comprises
   a) a chromium compound, a heteroatomic ligand, and a metal alkyl compound,
   b) an organometallic compound consisting essentially of a trialkylaluminum compound,
   c) a nickel compound and a bidentate organophosphine having at least one tertiary organophosphorus group or a complex of a nickel compound and a bidentate organophosphine having at least one tertiary organophosphorus group,
   d) a zirconium halide, hydrocarbyloxide, or carboxylate, and a metal alkyl compound,
   e) a zirconium halide, alkoxide, or carboxylate, a Lewis base, and a metal alkyl compound,
   f) a transition metal complex comprising a transition metal compound complexed to an α-diimine compound and a metal alkyl compound,
   g) a transition metal complex comprising a transition metal compound complexed to a pyridine 2,6-bisimine compound and a metal alkyl compound, or
   h) a transition metal compound, a pyridine 2,6-bisimine compound, and a metal alkyl compound.

9. The process of claim 1, wherein the reaction system further comprises a non-heat exchanged portion of the reaction system comprising a non-heat exchanged reaction mixture volume and a total non-heat exchanged surface area that does not provide heat exchange between the reaction mixture and the heat exchange medium;
   wherein the oligomer product discharge rate from the reaction system is between 1.5 $(lb)(hr^{-1})(gal^{-1})$ to 5.0 $(lb)(hr^{-1})(gal^{-1})$ and the ratio of the total heat exchanged surface area to the total reaction mixture volume within the reaction system is in a range from 1.25 $in^{-1}$ to 3.5 $in^{-1}$;
   wherein an average temperature of the heat exchange medium is within 5.3% of an average temperature of the reaction mixture within the heat exchanged portion of the reaction system;
   wherein an average temperature of the reaction mixture within the non-heat exchanged portion the reaction system is within 0.61% of an average temperature of the reaction mixture within the heat exchanged portion of the reaction system; and
   wherein a ratio of the heat exchanged reaction mixture volume to the total reaction mixture volume within the reaction system is in a range from 0.70 to 1.0.

10. The process of claim 9, further comprising: periodically or continuously introducing a reaction solvent into the reaction mixture within the reaction system.

11. The process of claim 9, wherein the reaction system comprises a reactor selected from the group consisting of a continuous stirred tank reactor, a plug flow reactor, and any combination thereof.

12. The process of claim 11, wherein the reaction system comprises
   a) a continuous stirred tank reactor wherein the heat exchange medium is in indirect contact with the reaction mixture within a jacket around at least a portion of an outer wall of the continuous stirred tank reactor, within internal heat exchange coils, or any combination thereof;
   b) one or more plug flow reactors wherein the heat exchange medium is in indirect contact with the reaction mixture through a wall of at least a portion of the one or more one plug flow reactors; or
   c) comprises a reaction mixture path comprising the reactor and wherein a portion of the reaction mixture is recycled through the reactor and a ratio of a volumetric reaction mixture recycle flow rate to a volumetric discharge rate of the reaction system effluent is between 8 and 60.

13. The process of claim 12, wherein the olefin monomer consists essentially of ethylene and the catalyst system comprises
   a) a chromium compound, a heteroatomic ligand, and a metal alkyl compound,
   b) an organometallic compound consisting essentially of a trialkylaluminum compound,
   c) a nickel compound and a bidentate organophosphine having at least one tertiary organophosphorus group or a complex of a nickel compound and a bidentate organophosphine having at least one tertiary organophosphorus group,
   d) a zirconium halide, hydrocarbyloxide, or carboxylate, and a metal alkyl compound,
   e) a zirconium halide, alkoxide, or carboxylate, a Lewis base, and a metal alkyl compound,
   f) a transition metal complex comprising a transition metal compound complexed to an α-diimine compound and a metal alkyl compound,
   g) a transition metal complex comprising a transition metal compound complexed to a pyridine 2,6-bisimine compound and a metal alkyl compound, or
   h) a transition metal compound, a pyridine 2,6-bisimine compound, and a metal alkyl compound.

* * * * *